(12) United States Patent
Rougeot et al.

(10) Patent No.: US 7,429,448 B2
(45) Date of Patent: Sep. 30, 2008

(54) THERAPEUTIC USE OF THE SMR1 PROTEIN AND ACTIVE DERIVATIVES THEREOF

(75) Inventors: Catherine Rougeot, Chevreuse (FR); Francois Rougeon, Sevres (FR)

(73) Assignee: Institut Pasteur, Paris (FR)

( * ) Notice: Subject to any disclaimer, the term of this patent is extended or adjusted under 35 U.S.C. 154(b) by 505 days.

(21) Appl. No.: 10/620,462

(22) Filed: Jul. 17, 2003

(65) Prior Publication Data

US 2004/0047805 A1 Mar. 11, 2004

Related U.S. Application Data

(62) Division of application No. 09/367,703, filed as application No. PCT/EP98/00956 on Feb. 19, 1998, now Pat. No. 6,818,405.

(51) Int. Cl.
*C12Q 1/00* (2006.01)
*G01N 33/48* (2006.01)
*G01N 33/50* (2006.01)

(52) U.S. Cl. ............................... 435/4; 435/7.8; 436/63; 436/503; 436/815

(58) Field of Classification Search ........................ None
See application file for complete search history.

(56) References Cited

U.S. PATENT DOCUMENTS

| 5,219,548 A | 6/1993 | Yang et al. |
| 6,589,750 B2 | 7/2003 | Rougeot et al. |

FOREIGN PATENT DOCUMENTS

| EP | 0 240 975 | 10/1987 |
| WO | WO 90/03981 | 4/1990 |
| WO | WO 95/00848 | 1/1995 |

OTHER PUBLICATIONS

Rougeot et al., "Selective processing of submandibular rat 1 protein at dibasic cleavage sites," Eur. J. Biochem., vol. 219, 1994, pp. 765-773.

Purdie et al., "Effects of danazol on mineral homeostasis in normal postmenopausal women: preliminary communication," Journal of Royal Society of Medicine, vol. 80, No. 11, 1987, pp. 681-682.

Rougeot et al., "Targets for SMR1-Pentapeptide Suggest a Link Between the Circulating Peptide and Mineral Transport," Am. J. Physiology, vol. 273, No. 4 PT2, Oct. 1997, pp. R1309-1320.

Singer et al., "Recent evolution of genes encoding the prohormone-like protein SMR1 in the rat submandibular gland," DNA Cell Biology, vol. 14, No. 2, 1995, pp. 137-144.

Courty et al., "Episodic evolution and rapid divergence of members of the rat multigene family encoding the salivary prohormone-like protein SMR1," Molecular Biology and Evolution, vol. 12, No. 6, 1996, pp. 758-766.

Drews R et al., "Proteolytic Maturation of Protein C Upon Engineering the Mouse Mammary Gland to Express Furin," Proceedings of the National Academy of Sciences of USA, vol. 92, No. 23, Nov. 1995, pp. 10462-10466.

Drucker et al., "Regulation of the biological activity of glucagon-like peptide 2 in vivo by dipeptidyl peptidase," Nature Biotechnology, (Abstract), 1997.

U.S. Appl. No. 11/594,105, filed Nov. 08, 2006, Rougeot, et al.
U.S. Appl. No. 10/620,462, filed Jul. 17, 2003, Rougeot, et al.

*Primary Examiner*—Karen A. Canella
(74) *Attorney, Agent, or Firm*—Oblon, Spivak, McClelland, Maier & Neustadt, P.C.

(57) ABSTRACT

The present invention pertains to the use of a peptide molecule consisting in a maturation product of SMR1 (Submandibular rat protein 1) of structural formula QHNPR, as well as the biologically active derivatives of the said peptide, for preventing or treating diseases associated with a mineral ion imbalance in a human or an animal body. More particularly, the present invention relates to the therapeutic use of the above-cited molecules for preventing or treating an hydromineral imbalance in organs and tissues such as kidney, bone, dental enamel, dental ivory, gut matrix, pancreas or glandular gastric mucosa. This invention also deals with therapeutic compositions comprising a pharmaceutically active amount of the above-described therapeutic molecules as well as with therapeutic methods using the said therapeutic compositions. Finally, the present invention relates to processes for selecting ligand molecules that possess an agonist or an antagonist biological activity on the target receptor of the QHNPR pentapeptide as well as to the selected ligand molecules themselves.

28 Claims, 27 Drawing Sheets

 
FIG.8A-1    FIG.8A-2

SEQUENCE LISTING

```
<160> NUMBER OF SEQ ID NOS: 14

<210> SEQ ID NO 1
<211> LENGTH: 5
<212> TYPE: PRT
<213> ORGANISM: Rattus rattus

<400> SEQUENCE: 1

Gln His Asn Pro Arg
1               5

<210> SEQ ID NO 2
<211> LENGTH: 6
<212> TYPE: PRT
<213> ORGANISM: Rattus rattus

<400> SEQUENCE: 2

Val Gln His Asn Pro Arg
```

```
1               5
```

<210> SEQ ID NO 3
<211> LENGTH: 7
<212> TYPE: PRT
<213> ORGANISM: Rattus rattus

<400> SEQUENCE: 3

```
Val Arg Gln His Asn Pro Arg
1               5
```

<210> SEQ ID NO 4
<211> LENGTH: 8
<212> TYPE: PRT
<213> ORGANISM: Rattus rattus

<400> SEQUENCE: 4

```
Val Arg Gly Gln His Asn Pro Arg
1               5
```

<210> SEQ ID NO 5
<211> LENGTH: 9
<212> TYPE: PRT
<213> ORGANISM: Rattus rattus

<400> SEQUENCE: 5

```
Val Arg Gly Pro Gln His Asn Pro Arg
1               5
```

<210> SEQ ID NO 6
<211> LENGTH: 10
<212> TYPE: PRT
<213> ORGANISM: Rattus rattus

<400> SEQUENCE: 6

```
Val Arg Gly Pro Arg Gln His Asn Pro Arg
1               5                   10
```

<210> SEQ ID NO 7
<211> LENGTH: 11
<212> TYPE: PRT
<213> ORGANISM: Rattus rattus

<400> SEQUENCE: 7

```
Val Arg Gly Pro Arg Arg Gln His Asn Pro Arg
1               5                   10
```

<210> SEQ ID NO 8
<211> LENGTH: 33
<212> TYPE: DNA
<213> ORGANISM: Unknown
<220> FEATURE:
<223> OTHER INFORMATION: synthetic DNA

<400> SEQUENCE: 8

```
gtcagaggcc caagaagaca acataatcct aga                           33
```

<210> SEQ ID NO 9
<211> LENGTH: 5
<212> TYPE: PRT
<213> ORGANISM: Unknown
<220> FEATURE:
<223> OTHER INFORMATION: synthetic peptide
<220> FEATURE:
<221> NAME/KEY: Xaa
<222> LOCATION: (1)..(1)

```
<223> OTHER INFORMATION: Xaa is Glp

<400> SEQUENCE: 9

Xaa His Asn Pro Arg
1               5

<210> SEQ ID NO 10
<211> LENGTH: 5
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa is D3,4 Pro

<400> SEQUENCE: 10

Gln His Asn Xaa Arg
1               5

<210> SEQ ID NO 11
<211> LENGTH: 4
<212> TYPE: PRT
<213> ORGANISM: Unknown
<220> FEATURE:
<223> OTHER INFORMATION: synthetic tetrapeptide

<400> SEQUENCE: 11

Gln His Asn Pro
1

<210> SEQ ID NO 12
<211> LENGTH: 6
<212> TYPE: PRT
<213> ORGANISM: Unknown
<220> FEATURE:
<223> OTHER INFORMATION: synthetic peptide

<400> SEQUENCE: 12

Arg Gln His Asn Pro Arg
1               5

<210> SEQ ID NO 13
<211> LENGTH: 6
<212> TYPE: PRT
<213> ORGANISM: Unknown
<220> FEATURE:
<223> OTHER INFORMATION: synthetic peptide

<400> SEQUENCE: 13

Trp Gln His Asn Pro Arg
1               5

<210> SEQ ID NO 14
<211> LENGTH: 11
<212> TYPE: PRT
<213> ORGANISM: Unknown
<220> FEATURE:
<223> OTHER INFORMATION: SMR1-related peptide structure or motif
<220> FEATURE:
<221> NAME/KEY: MISC_FEATURE
<222> LOCATION: (1)..(6)
<223> OTHER INFORMATION: Xaa at positions 1-6 may be present or absent.
      When present at positions 1-6 the sequence is VRGPRR; when present
      only at positions
```

```
                                                    -continued
      2-6, 3-6, 4-6, 5-6 or 6 this sequence represents the following
      residues respectively:  VRGPR, VRGP, VRG, VR, or V.

<400> SEQUENCE: 14

Xaa Xaa Xaa Xaa Xaa Xaa Gln His Asn Pro Arg
1               5                   10
```

THERAPEUTIC USE OF THE SMR1 PROTEIN AND ACTIVE DERIVATIVES THEREOF

CROSS-REFERENCE TO RELATED APPLICATIONS

This application is a divisional of U.S. application Ser. No. 09/367,703, filed Oct. 13, 1999, now U.S. Pat. No. 6,818,405 which is a 371 of PCT/EP98/00956, filed Feb. 19, 1998, which claims benefit under 365(c) to U.S. application Ser. No. 08/801,405, filed Feb. 20, 1997, now U.S. Pat. No. 6,589,750.

BACKGROUND OF THE INVENTION (i) Field of the Invention

The present invention pertains to the therapeutic use of a peptide molecule derived from maturation products of SMR1 (Submandibular rat protein 1).

(ii) Description of the Related Art

The intracellular or systemic hydro-mineral imbalance of the body of a mammal, and more specifically of the human body is the cause of multiple pathologies affecting the metabolism and the physiological behavior of diverse organs and tissues, such as bone, kidney, parathyroid, pancreas, intestine, the glandular mucosa of the stomach or the prostate as well as salivary glands.

In the body of a mammal, the maintenance of the transmembrane potassium/sodium and magnesium/calcium ratios is critically important in the control of cell excitation and the regulation of many aspects of intracellular metabolism. The most active tissues such as nerve, liver and muscle have a higher ratio of potassium/sodium and magnesium/calcium than inactive tissues such as skin and erythrocytes. In addition, the most active tissues have a higher phosphorus content than inactive tissues, in keeping with the role of phosphate esters in cellular energy metabolism.

An adult human contains approximately 1,000 g of calcium (Krane et al., 1970). Some 99% of this calcium is in the skeleton in the form of hydroxyapatite, and 1% is contained in the extracellular fluids and soft tissues. About 1% of the skeletal content of calcium is freely exchangeable with the extracellular fluids. Although small as a percentage of skeletal content, this exchangeable pool is approximately equal to the total content of calcium in the extracellular fluids and soft tissues, and serves as an important buffer or storehouse of calcium. Thus, calcium plays two predominant physiological roles in the organism. In bone, calcium salts provide the structural integrity of the skeleton. In the extracellular fluids and in the cytosol, the concentration of calcium ions is critically important in the maintenance and control of a number of biochemical processes, and the concentrations of $Ca^{2+}$ in both compartments are maintained with great constancy (Broadus, 1993). Other important mineral ions such as sodium, magnesium or phosphorus are deeply involved in the mineral ion balance necessary for a good intra- and extra-cellular metabolism. The term mineral ion balance refers to the state of mineral homeostasis in the organism vis-à-vis the environment. In zero balance, mineral intake and accretion exactly match mineral losses; in positive balance, mineral intake and accretion exceed mineral losses, and in negative balance, mineral losses exceed mineral intake and accretion. Under normal circumstances net calcium absorption provides a surplus of calcium that considerably exceeds systemic requirements.

The extracellular pool of orthophosphate (about 550 mg in human) is in dynamic equilibrium with phosphorus entry and exit via the intestine, bone, kidney and soft tissues. In zero balance, fractional net phosphorus absorption is about two-thirds of phosphorus intake. This amount represents a vast excess over systemic requirements and is quantitatively excreted into the urine.

The extracellular pool of magnesium (about 250 mg in human) is in bidirectional equilibrium with magnesium fluxes across the intestine, bone, kidney and soft tissues. In zero balance, the magnesium derived from the net intestinal absorption (about 100 mg/day in human) represents a systemic surplus and is quantitatively excreted.

Two organs are mainly involved in the absorption and excretion of the different mineral ions of the body: 1) Hormonal and/or intrinsic mechanisms of mineral ion absorption in the intestine provide the body with a mineral supply that exceeds systemic mineral needs by a considerable measure; 2) the renal tubule plays the dominant quantitative role in maintaining normal mineral homeostasis.

Few endogenously produced metabolites have already been shown to participate actively in the maintenance of the mineral ion balance within the body.

The 1,25-dihydroxyvitamin D (also named calcitriol) is the only recognized hormonal stimulus of active intestinal calcium absorption that occurs principally in the duodenum and the jujenum (Lemann Jr J., 1993). As a consequence, reduced net intestinal calcium absorption occurs when either dietary calcium intake is limited, when serum 1,25-dihydroxyvitamin D concentrations are low or when the intestine is unresponsive to this hormone. In contrast, increased intestinal calcium absorption occurs when serum 1,25-dihydroxyvitamin D concentrations are high. Thus defects in the regulation of the 1,25-dihydroxyvitamin D concentration in the serum can cause major disorders reducing or enhancing intestinal calcium absorption and lead to a pathological state. The 1,25-dihydroxyvitamin D also influences the body intake of phosphate.

A second endogenous factor involved in the mineral ion balance is the parathyroid hormone (PTH). Parathyroid hormone regulates the level of calcium, and phosphate in blood by modulating the activity of specific cells in bone and kidney. These actions serve to: 1) stimulate reabsorption of calcium and phosphate from bone; 2) stimulate reabsorption of calcium and inhibit reabsorption of phosphate from glomerular filtrate; and 3) stimulate the renal synthesis of 1,25-dihydroxyvitamin D thereby increasing intestinal absorption of calcium and phosphate.

A third endogenous factor intervening in the mineral ion balance is calcitonin. Calcitonin (CT) is a 32-amino-acid peptide that is secreted primarily by thyroidal C-cells (Deftos, 1993). Its main biological effect is to inhibit osteoclastic bone resorption. This property has led to CT's use for disorders characterized by increased bone resorption, such as Paget's disease, osteoporosis and for the hypercalcemia of malignancy. The secretion of CT is regulated acutely by blood calcium and chronically by gender and perhaps age. Calcitonin is metabolized by the kidney and the liver. The amino acid sequence of CT is widely conserved through the evolution, from fish to mammals.

Defects in the mineral ion balance are the cause of multiple disorders affecting either the bone, the kidney, the intestine, the pancreas, the dental tissues (enamel and ivory), or the stomach mucosa.

A mineral ion imbalance affects the bone remodeling capacity causing disorders such as osteoporosis or affects the bone resorption capacity such as in the hyper-parathyroidism disease. The bone remodeling system has been characterized in numerous publications in the recent past (Parfitt, 1986).

Bone remodeling occurs on trabecular and Haversian bone surfaces. The first step is activation of osteoclast precursors to form osteoclasts that then begin to excavate a cavity on a surface. After removal of bone tissues (about 0.05 mm$^3$), the site remains quiescent for a short time, following which activation of osteoblast precursors occurs at the site and the excavation is refilled. This process serves several functions, among them the removal of aged, microdamaged bone tissue and rearrangement of the bone architecture to meet the needs of mechanical support. With normal daily use of the skeleton, bone loss, abnormal accumulation of microdamage, or errors in geometry can come about only through defects in this system, for example a defect in the mineral ion balance. Osteoporosis is a major public health concern and there is consequently a great need for new therapeutical molecules that will be able to regulate the mineral ion balance in the body and, if possible, more efficient and more selective (target specific) than the molecules presently used in therapeutic, such as oestrogen and calcitonin. Other bone absorption or resorption diseases may be caused by defects in the renal or gastrointestinal mineral ion metabolism, such as renal osteodystrophy or even caused by a pancreatic insufficiency.

Primary hyperparathyroidism is a very common cause of hypercalcemia, with estimates of incidence as high as 1 in 500 to 1 in 1000 (Bilezikian, 1990). Hyperparathyroism is a hypercalcemia occurring in association with elevated levels of parathyroid hormone, often caused by a benign, solitary adenoma.

Hypercalcemia may be the result of diverse other disorders such as familial hyperparathyroid syndromes (Szabo J. et al., 1993), familial hypocalciuric hypercalcemia (Marx S. J., 1993), hypercalcemia due to malignancy states (Stewart A. F., 1993; Mundy G. R., 1993) or due to granuloma-forming disorders (Adams, J. S., 1993).

On the order hand, defects in the mineral ion balance can result in hypocalcemia which is encountered in diseases associated with a low serum albumin concentration or also with idiopathic hypoparathyroidism. Hypocalcemia itself is sometimes due to hypomagnesemia or hyperphosphatemia, or to an impaired secretion of the parathyroid hormone (Shane E., 1993) or also to vitamin D disorders (Insogna K. L., 1993).

The dental tissues may also be affected in the case of a defect in the mineralization and formation of the dental ivory or enamel. Pancreas is also an organ very sensitive to a defect in mineral ion equilibrium, which is able to cause an inflammation named pancreatitis. Even the submandibular gland may be affected, causing a pathological state of lithiasis which is associated with calcium deposits. The kidney may also be affected, resulting in the development of nephrolithiasis.

In the same way, aluminum accumulation in uremic patients is associated with bone disease, which is characterized by reduced bone formation leading to osteodystrophy (Sherrard et al., 1988).

Two other disorders of public health concern are respectively a hypercalcemia resulting from medications (Stewart, 1993) and the parathyroid hormone resistance syndromes (Levine, 1993).

Due to the multiple disorders caused by a decrease or an increase of the mineral ion metabolism (principally calcium, magnesium, phosphorous or aluminum ions) and the very small number of molecules that are, to date, of therapeutic value in the prevention or in the treatment of the above-described pathological states, there exists a great public need for new active molecules that are able to regulate the mineral ion concentrations within the body.

The inventors have previously characterized a new rat submandibular gland protein, named SMR1 (submandibular rat 1 protein), which has the structure of a prohormone and whose synthesis is under androgen control (Rosinsky-Chupin et al., 1988 and PCT Patent Application No. WO 90/03981). The gene encoding SMR1 belongs to a new multigene family, the VCS family, which has been localized to chromosome 14, bands p 21-p 22 (Courty et al., 1996; Rosinsky-Chupin et al., 1995) and for which human gene counterpart has been characterized. The gene has a similar organization to a number of hormone precursor genes (Rosinsky-Chupin et al., 1990). SMR1 mRNA is expressed in a highly tissue-, age- and sex-specific manner in the acinar cells of the male rat submaxillary gland (SMG) and in the prostate (Rosinsky-Chupin et al., 1993).

It has been described that, in vivo, SMR1 is selectively processed at pairs of basic amino acid sites in a tissue- and sex-specific manner to give rise to mature peptide products, in a manner similar to the maturation pathway of peptide-hormone precursors (Rougeot et al., 1994). Generally, this selective proteolytic fragmentation has been shown to be critical for the generation and the regulation of biologically active peptides (Lindberg et al., 1991; Steiner et al., 1992). The biosynthesis of the peptides generated from SMR1 or from its human counterpart by cleavage at pairs of arginine residues e.g. the undecapeptide: VRGPRRQHNPR (SEQ ID NO: 7); the hexapeptide: RQHNPR (SEQ ID NO: 12); and the pentapeptide: QHNPR (SEQ ID NO: 1), is subject to distinct regulatory pathways depending on 1) the organ: SMG and prostate, 2) the developmental stage: from 6 weeks postnatal, 3) the sex: predominantly in the male, and 4) gonad hormones: the androgens. Furthermore, in vivo, the mature peptides which accumulate in the male rat SMG, are exported into the extracellular space in response to a specific external stimulus and, in this way are transported within the salivary and blood fluids (Rougeot et al., 1993). The fact that these peptides are mainly produced in postpubescent male rats and are secreted into the saliva and blood under stimulated conditions, led one to postulate that they have a local and systemic physiological role in mediating some male-specific behavioral characteristics but this role was totally unknown.

SUMMARY AND OBJECTS OF THE INVENTION

The inventors have now discovered that the maturation products of the SMR1 protein, specifically a peptide of structural formula XQHNPR (SEQ ID NO: 14) recognize specific target sites in organs that are deeply involved in the mineral ion concentration. This discovery has led the inventors to assign to the SMR1 pentapeptide, hexapeptide or undecapeptide an active role in the regulation of the metal ion concentrations in the body fluids and tissues, and thus a therapeutic role of these peptides in all the metabolic disorders related to a mineral ion imbalance.

Thus, the present invention concerns the therapeutic use of the peptide of structural formula XQHNPR (SEQ ID NO: 14) wherein X denotes a hydrogen atom or X represents an amino acid chain chosen from the following: X=V or X=VR or X=VRG or X=VRGP or X=VRGPR or X=VRGPRR, for preventing or treating diseases caused by a mineral ion imbalance in a mammal, specifically in human.

More particularly, one object of the present invention is the use of the above-described therapeutic peptides for treating bone, teeth, renal, kidney, intestine, pancreas, stomach mucosa or parathyroid disorders caused principally by a mineral ion imbalance in the body fluids or tissues.

Accordingly, the therapeutic peptides according to the present invention are used for preventing or treating diseases like hyper- or hypo-parathyroidism, osteoporosis, pancreatitis, submandibular gland lithiasis, nephrolithiasis or osteodystrophy.

The discovery of the therapeutic activity of the SMR1 protein and its derived peptides as well as their physiological in vivo targets has allowed the inventors to design new molecules that can be considered as biologically active derivatives of the above-described therapeutic peptides.

Such biologically active derivatives of the therapeutic peptides according to the invention are peptides that are structurally and chemically related to the XQHNPR (SEQ ID NO: 14), such as peptides having the same amino acid sequence as the initial peptides but containing one or several modified amino acids that are able to confer a better in vivo stability to the therapeutically active molecule and which possess the same biological activity as the endogenous peptide or which behave as an antagonist molecule of the endogenous peptide.

Thus, the therapeutic use of peptides that are homologous to the XQHNPR (SEQ ID NO: 14) peptide is also part of the present invention. By homologous peptide according to the present invention is meant a peptide containing one or several amino acid substitutions in the XQHNPR (SEQ ID NO: 14) sequence. The amino acid substitution consists in the replacement of one or several-consecutive or non-consecutive-amino acids by "equivalent" amino acids. The expression "equivalent" amino acid is used herein to name any amino acid that may substituted for one of the amino acids belonging to the initial peptide structure without modifying the hydrophilicity properties and the biological target of the initial peptide structure. Preferably, the peptides containing one or several "equivalent" amino acids retain their specificity and affinity properties to the biological targets of the XQHNPR (SEQ ID NO: 14) peptide. In other words, the "equivalent" amino acids are those which allow the generation or the obtention of a polypeptide or peptide with a modified sequence as regards to XQHNPR (SEQ ID NO: 14), said modified polypeptide or peptide being able to act as an agonist or an antagonist molecule of the XQHNPR (SEQ ID NO: 14) peptide.

These equivalent amino acids may be determined by their structural homology with the initial amino acids to be replaced and by their biological activity on the target cells of the XQHNPR (SEQ ID NO: 14) peptide.

As an illustrative example, it should be mentioned the possibility of carrying out substitutions like, for example, leucine by valine or isoleucine, aspartic acid by glutamic acid, glutamine by asparagine, arginine by lysine etc., it being understood that the reverse substitutions are permitted in the same conditions.

By modified amino acid according to the present invention is also meant the replacement of a residue in the L-form by a residue in the D form or the replacement of the glutamine (Q) residue by a Pyro-glutamic acid compound. The synthesis of peptides containing at least one residue in the D-form is, for example, described by Koch et al. in 1977.

The 20 μm sections were exposed for 15 days with 3H hyperfilm. Black areas correspond to high uptake of radioactivity. The highest concentration of silver grains is seen in the renal outer medullary, gastric glandular mucosa, pancreatic and submandibular lobules as well as visible bone tissues (skull base, rib, vertebra and limb) and dental tissue.

Figure 1A:
FIG. 1. Representative whole-body autoradiographs of a five week-old male rat, 60 min after i.v. injection of SMR1-derived $^3$H-pentapeptide (2 μg or 3 nmoles/100 g body weight). A: lateral sagittal section, and B: midsagittal section.
Figure 1B:
Figure 2:
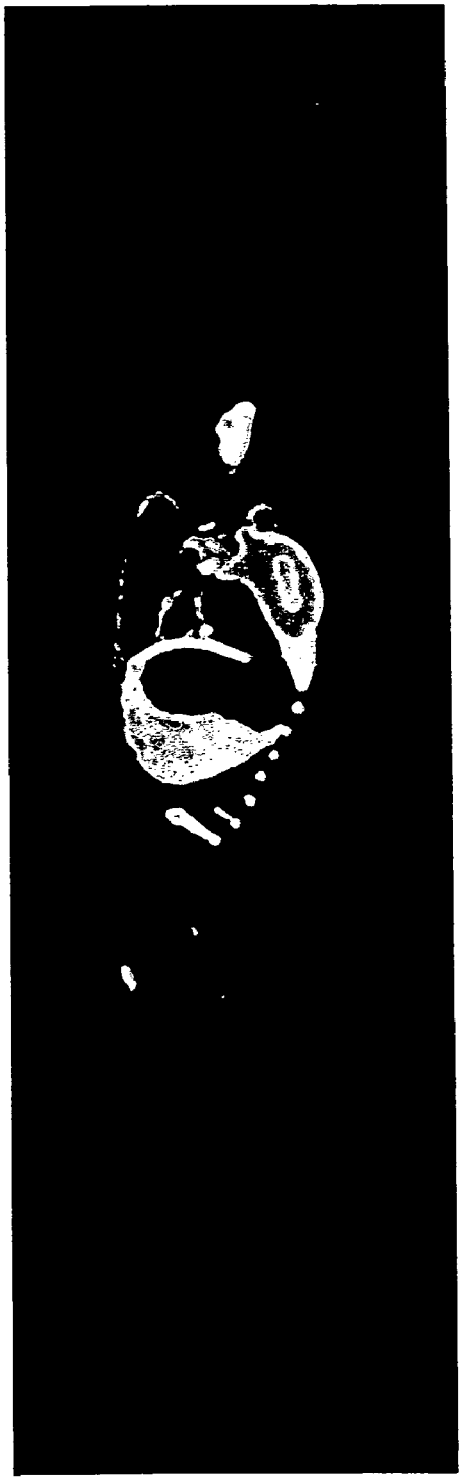
Figure 2:
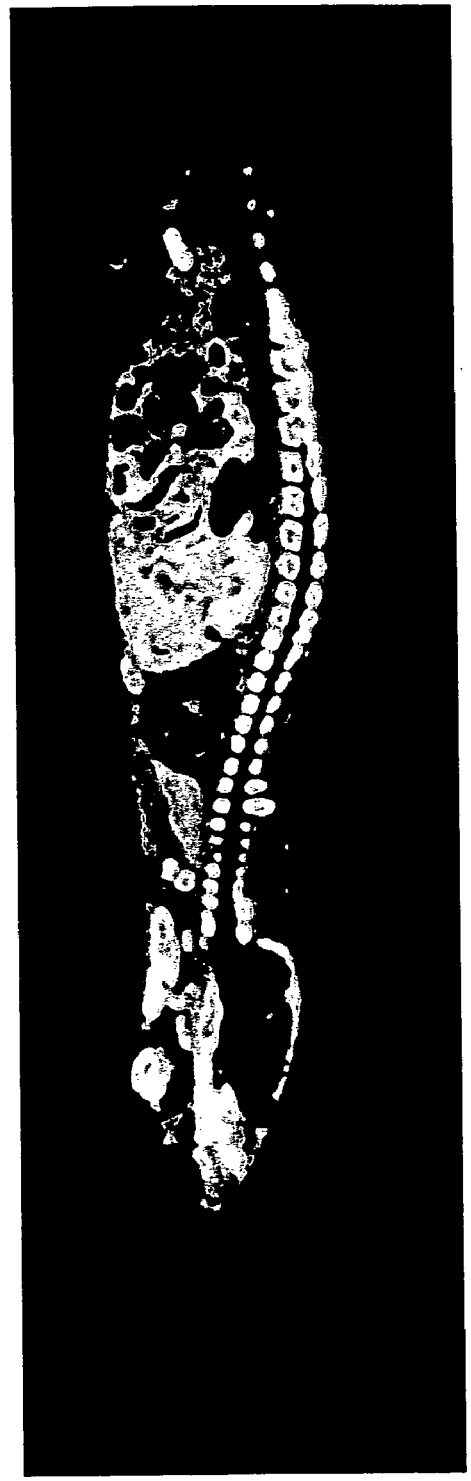

FIG. 2. Representative mapping of target organs for SMR1-derived $^3$H-pentapeptide using the high resolution β-radio imager.

A: midsagittal section, and B: lateral sagittal section of rat whole body, 60 min. post-injection of 3 nmoles or 2 μg tritiated peptide.

The 20 μm sections were exposed for 8 hrs. Red areas correspond to high uptake of radioactivity. The highest concentration of radioactivity is seen in the renal outer medullary, gastric glandular mucosa, pancreatic and submandibular lobules as well as visible bone tissues (skull base, rib, vertebra and limb) and dental tissue.

Figure 3:
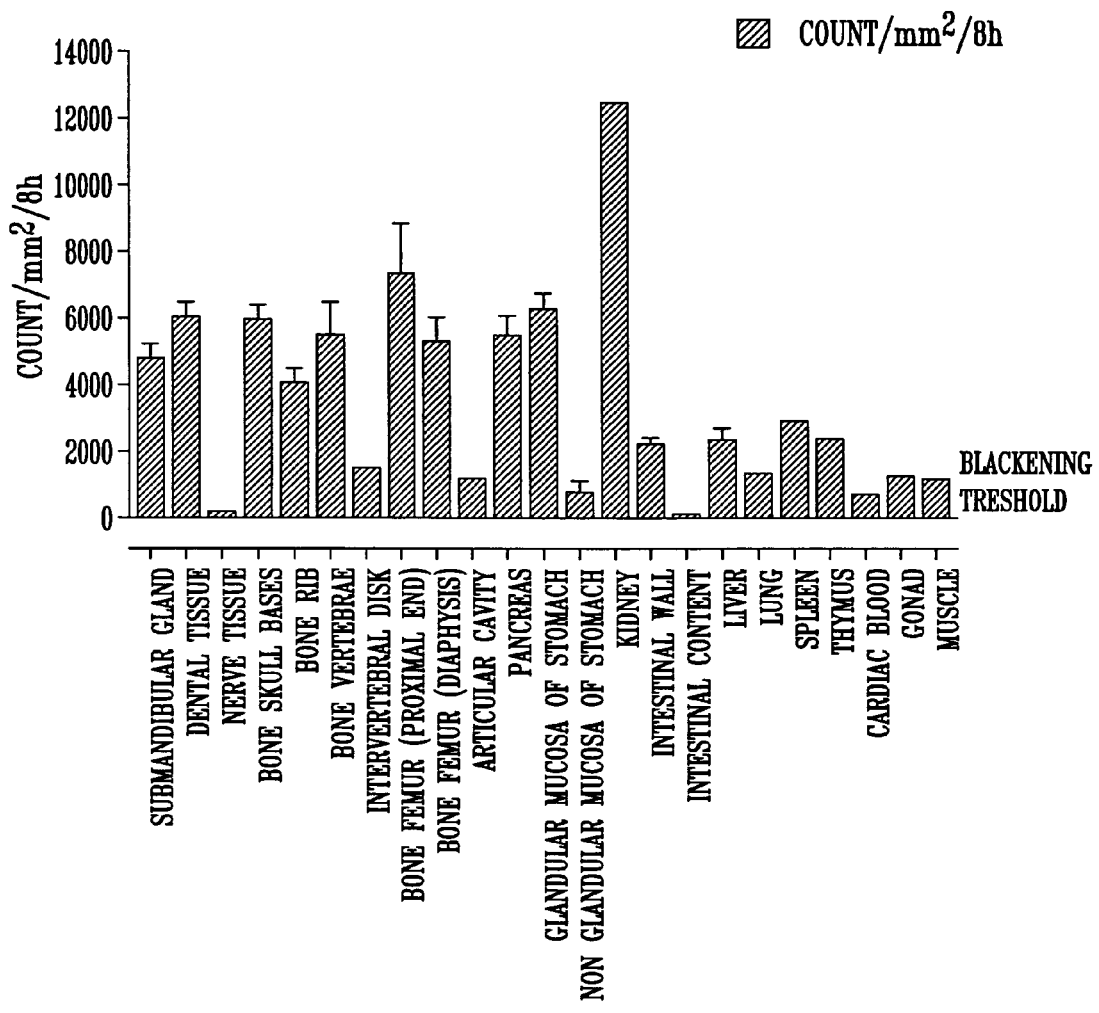

FIG. 3. Quantitative profile of radioactivity in various tissues following administration of 2 μg or 3 nmoles $^3$H-pentapeptide (QHNPR, SEQ ID NO: 1), 60 min post-dose. Direct quantification was assessed using the β-radio imager within sagittal whole body sections. The number of β particles emitted per area was counted for 8 hrs., and expressed as counts/mm$^2$. Assessment of quantitative regional differences was performed with computer-assisted image analysis using the β-vision program. Bars represent means ±SD of triplicate determinations from the same structure and two whole body sections.

Figure 4:
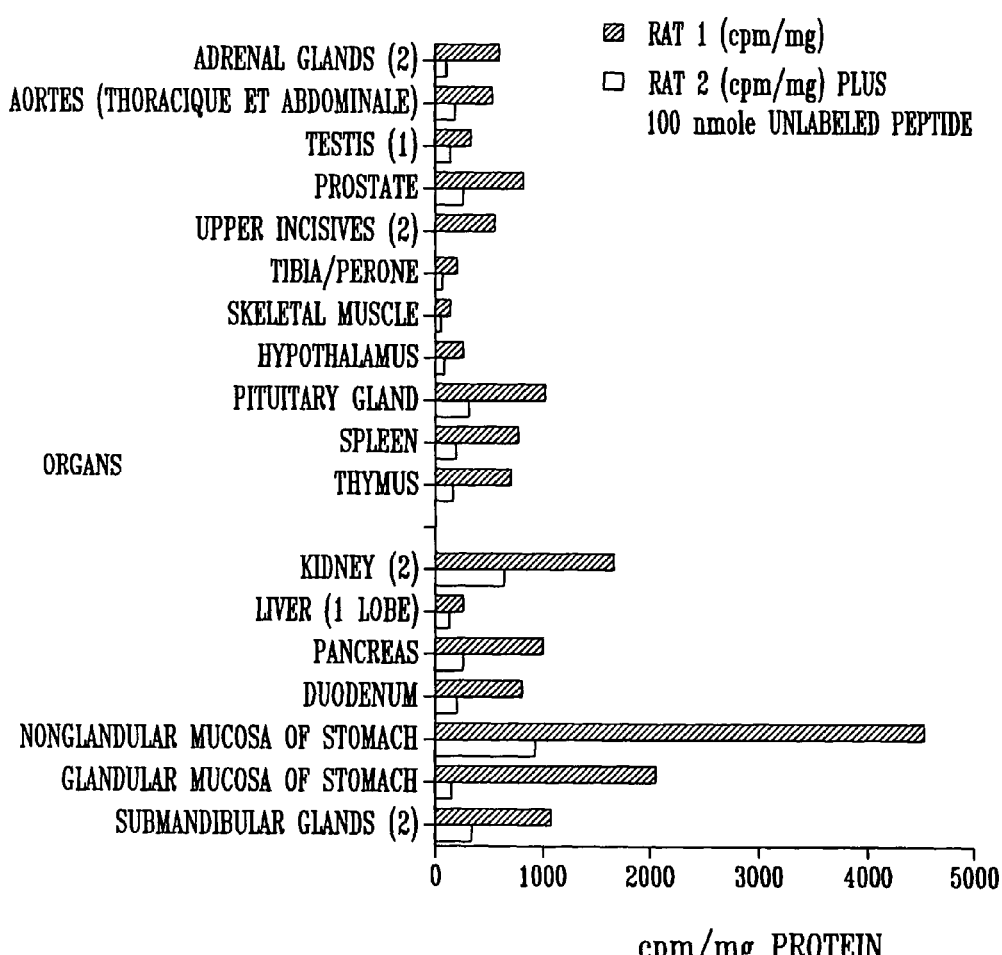

FIG. 4. Quantitative profile of radioactivity in various tissues following administration of 100 pmoles $^3$H-hexapeptide, 60 min post-dose or plus 100 nmoles unlabelled peptide to non specific binding.

Quantification was assessed using a spectrometer and calculated as cpm/mg protein from whole tissue extracts.

Figure 5:
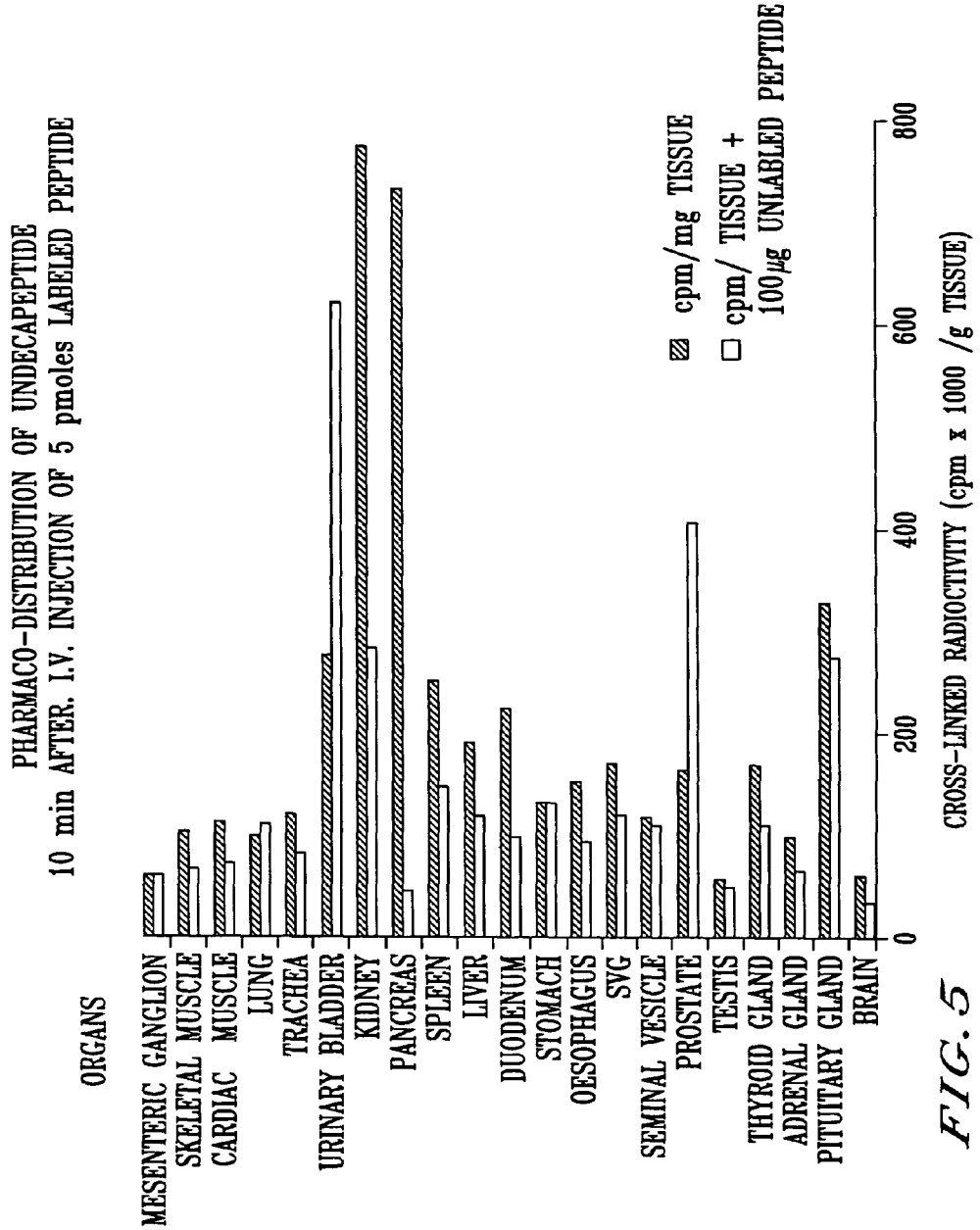

FIG. 5. Quantitative profile of radioactivity in various tissues following administration of 5 pmoles $^{125}$I-undecapeptide (VRGPRRQHNPR, SEQ ID NO: 7), 10 min post-dose or plus 100 nmoles unlabeled peptide to non specific binding.

Quantification was assessed using a gama-spectrometer and calculated as cpm/g tissue.

Figures 6A, 6B:
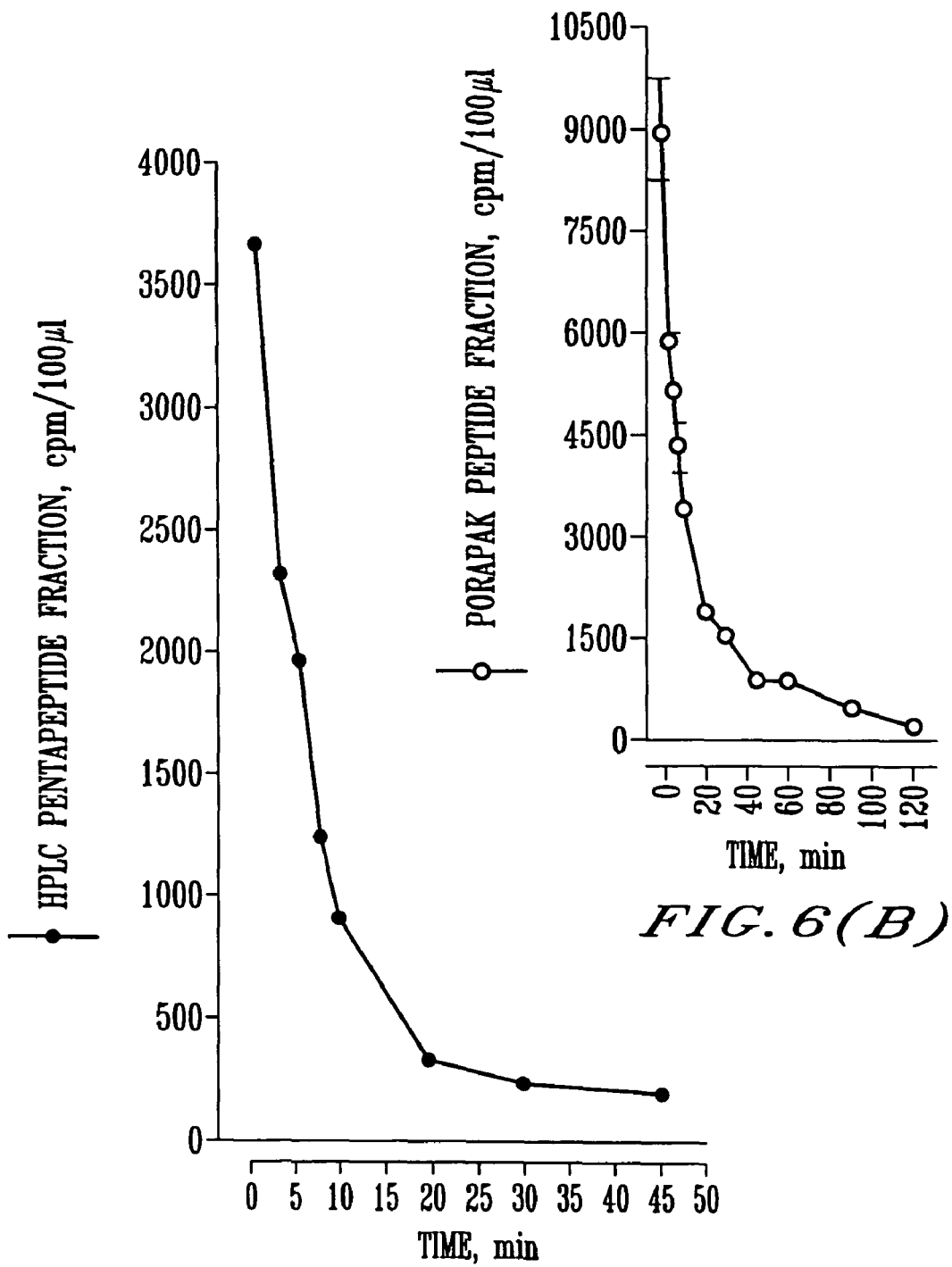
Figure 7A:
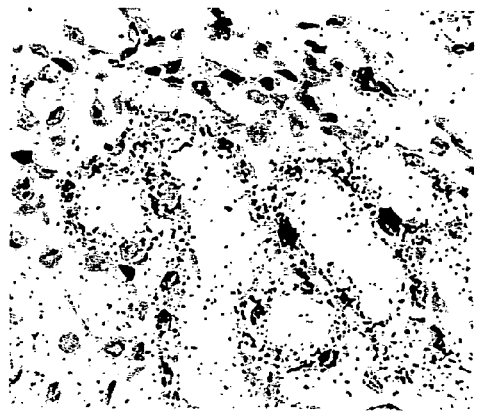
Figure 7B:
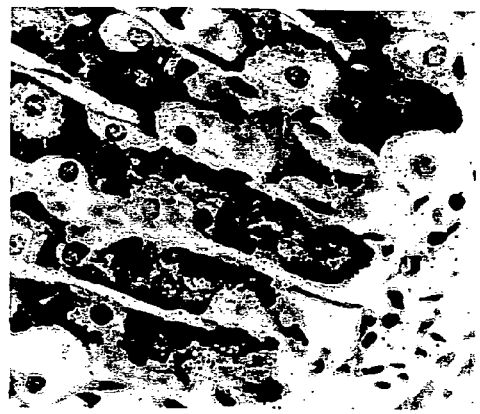
Figure 7C:
Figure 7D:
Figure 7E:
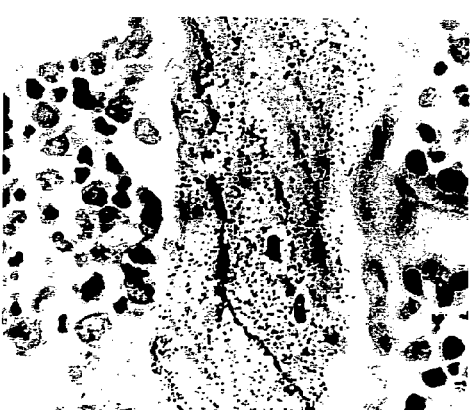
Figure 7F:

FIG. 6. Representative profile of the time course of SMR1-derived pentapeptide plasma levels, in male rats, after a single intravenous injection of 110 ng tritiated pentapeptide.

Plasma free peptide fraction was measured after RP porapak Q purification (values are mean ±SD of 2 rats) and free pentapeptide fraction after RP HPLC chromatography, as described in "materials and methods."

FIG. 7. Bright-field photomicrograph of autoradiograph of in vivo $^3$H-pentapeptide cellular uptake in sections of various organs, including A: outer medulla of kidney, B: glandular gastric mucosa, C: pancreatic lobules, D: root of upper incisor, E: vertebral bone, F: proximal long bone tibia.

Bright-field images represent in vivo radiolabeling 5 μm sections, 60 min after injection of physiological concentrations of tritiated peptide (160 ng). The sections were stained with hematoxylin and toluidine blue in order to verify microanatomical details and was photographed to a final print magnification of 400× (A, B, D, E, F) and 600× (C).

Figures 3, 8B:
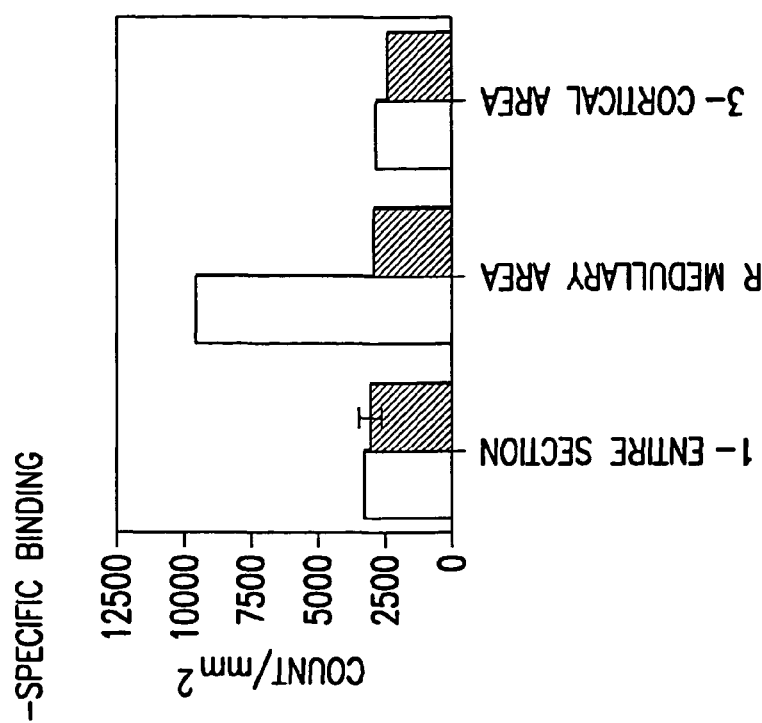
Figures 2, 8B:
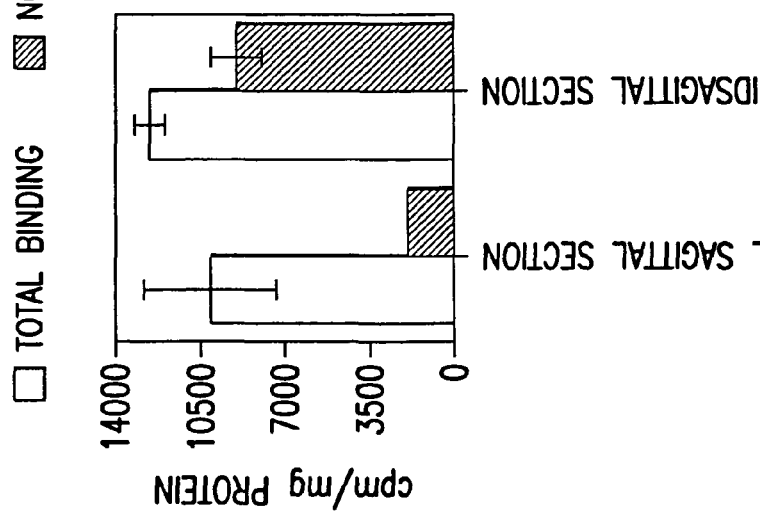

FIG. 8. A: Mapping of $^3$H-pentapeptide renal distribution using the high resolution β-radio imager. In vivo radiolabeling, 60 min after injection of physiological concentrations of tritiated peptide (160 ng) (A-1), or plus 100-fold excess of unlabeled peptide to nonspecific binding (A-2). The 5 μm sections were exposed for 50 hr. The white area corresponds to the highest concentration of radioactivity.

B: Quantification of the radioactivity within the kidney following 60 min administration of physiological concentrations of $^3$H-pentapeptide in vivo or plus 100-fold excess of unlabeled corresponding peptide.

The radioactivity content was measured directly with a β-spectrometer and calculated as cpm/mg protein from whole tissue 20 μm sections (B-2) or from whole tissue extracts (B-1) or with a β-radio imager and calculated as count X100/mm² from 5 μm sections (B-3-1). Assessment of quantitative regional differences was performed with computer-assisted image analysis using the β-vision program. (B-3-2 and B-3-3).

Figure 9:
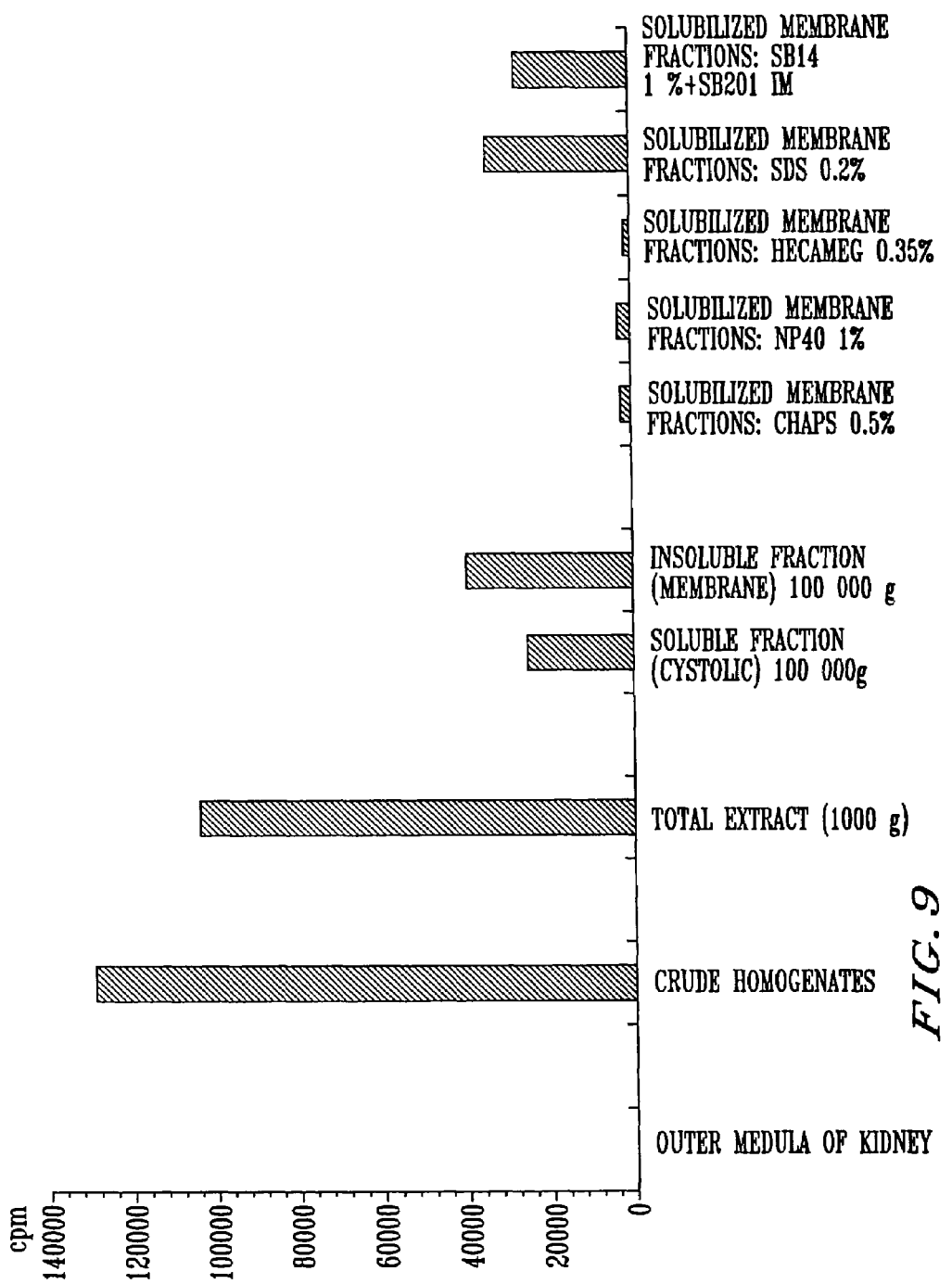

FIG. 9: quantitative profile of radioactivity of different fractions of membrane preparations of outer medulla of kidney.

Figure 10:
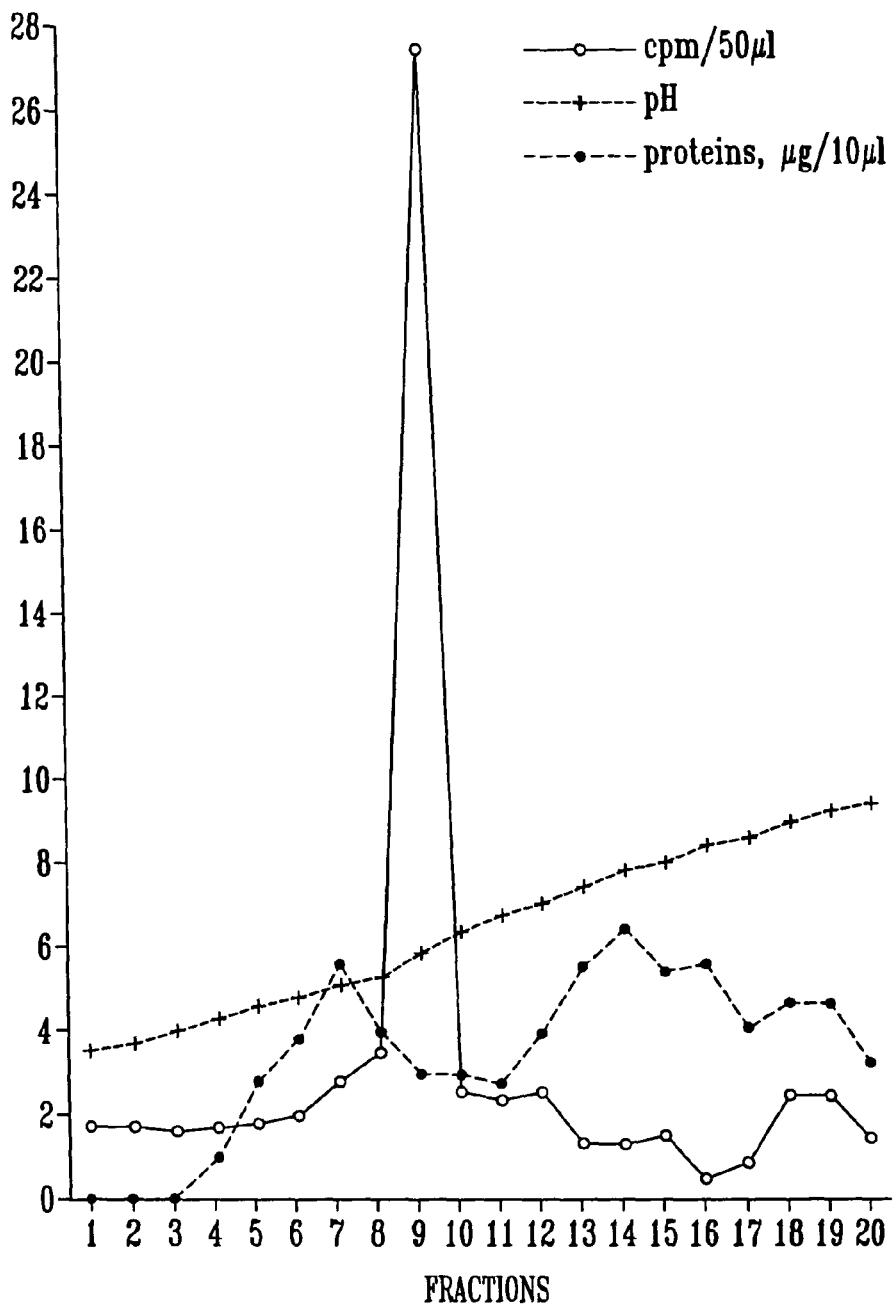

FIG. 10: Isoelectrofocusing (IEF) of membrane proteins of outer medulla of kidney solubilized with SB14 1% and SB201 1 M.

Figure 11:
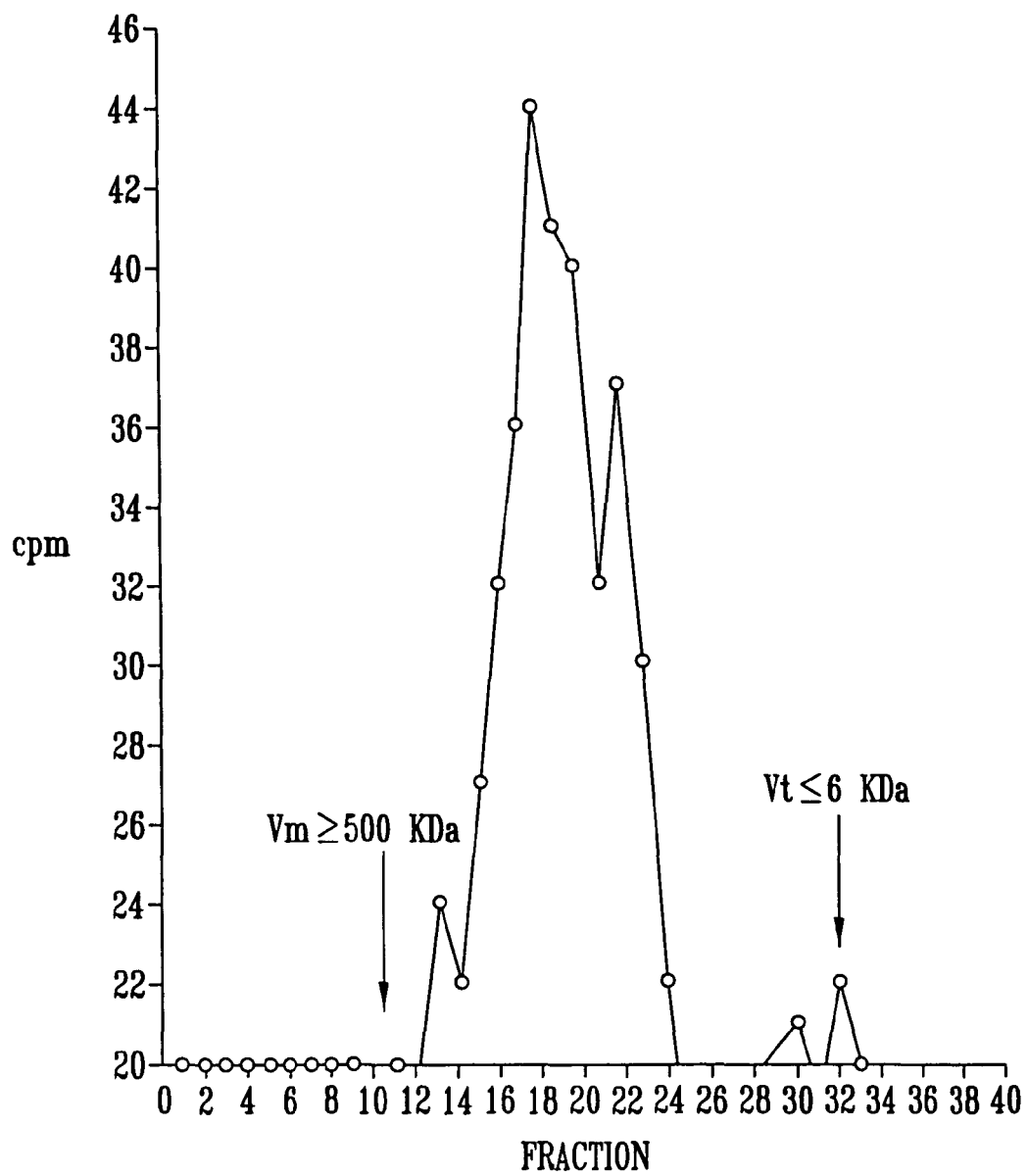

FIG. 11: Molecular sieve (Superdex 200) of the fractions resulting from isoelectrofocusing of solubilized membrane preparations of outer medulla of kidney.

Figure 12:
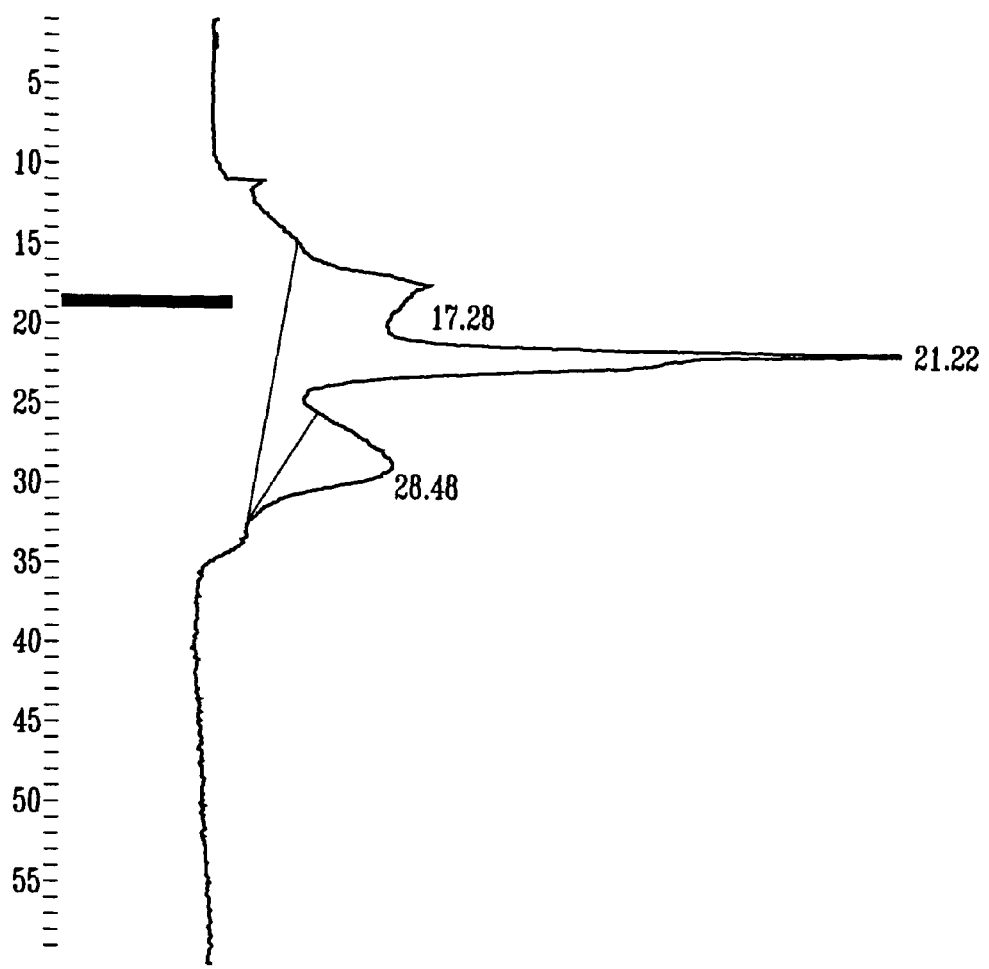

FIG. 12: Chromatographic profile corresponding to FIG. 10 with an optical density at 274 nm, and resulting from fractionating at 0.75 ml/min.

Isoelectrofocusing fractions of the solubilized membrane preparations of outer medulla of kidney.

Figure 13A:
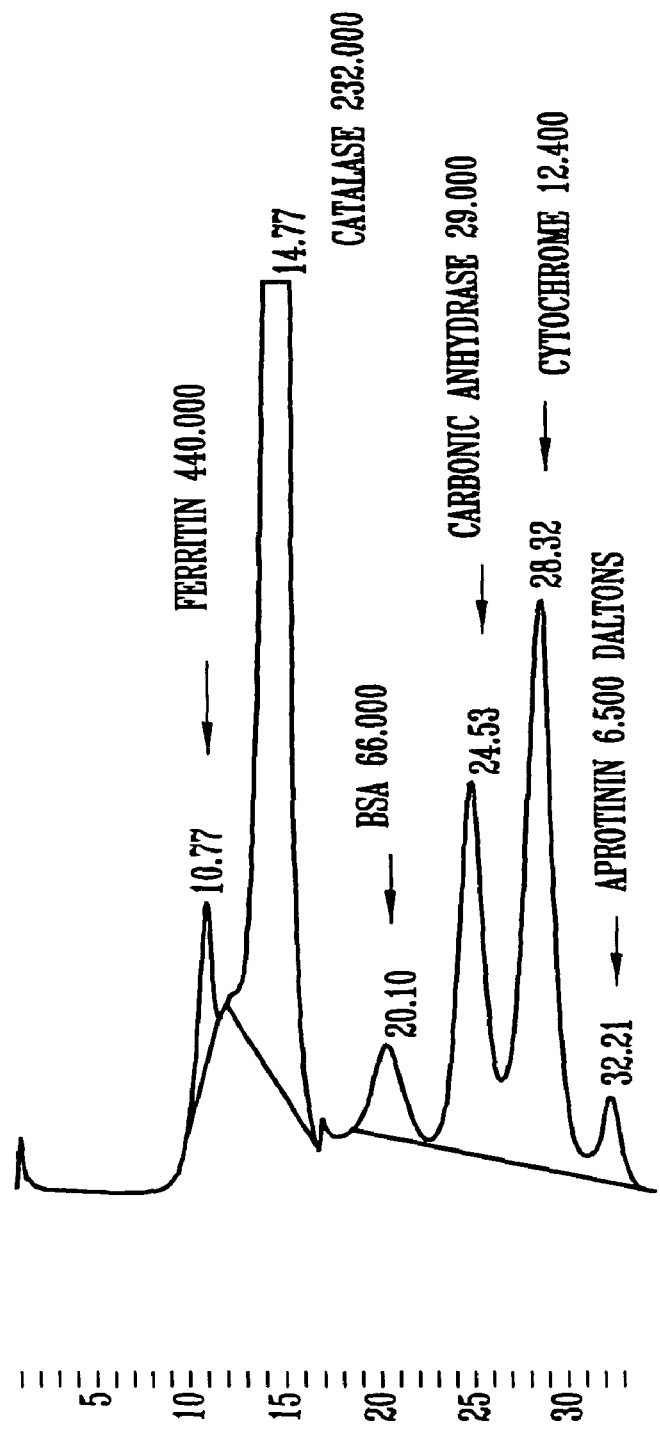
Figure 13B:
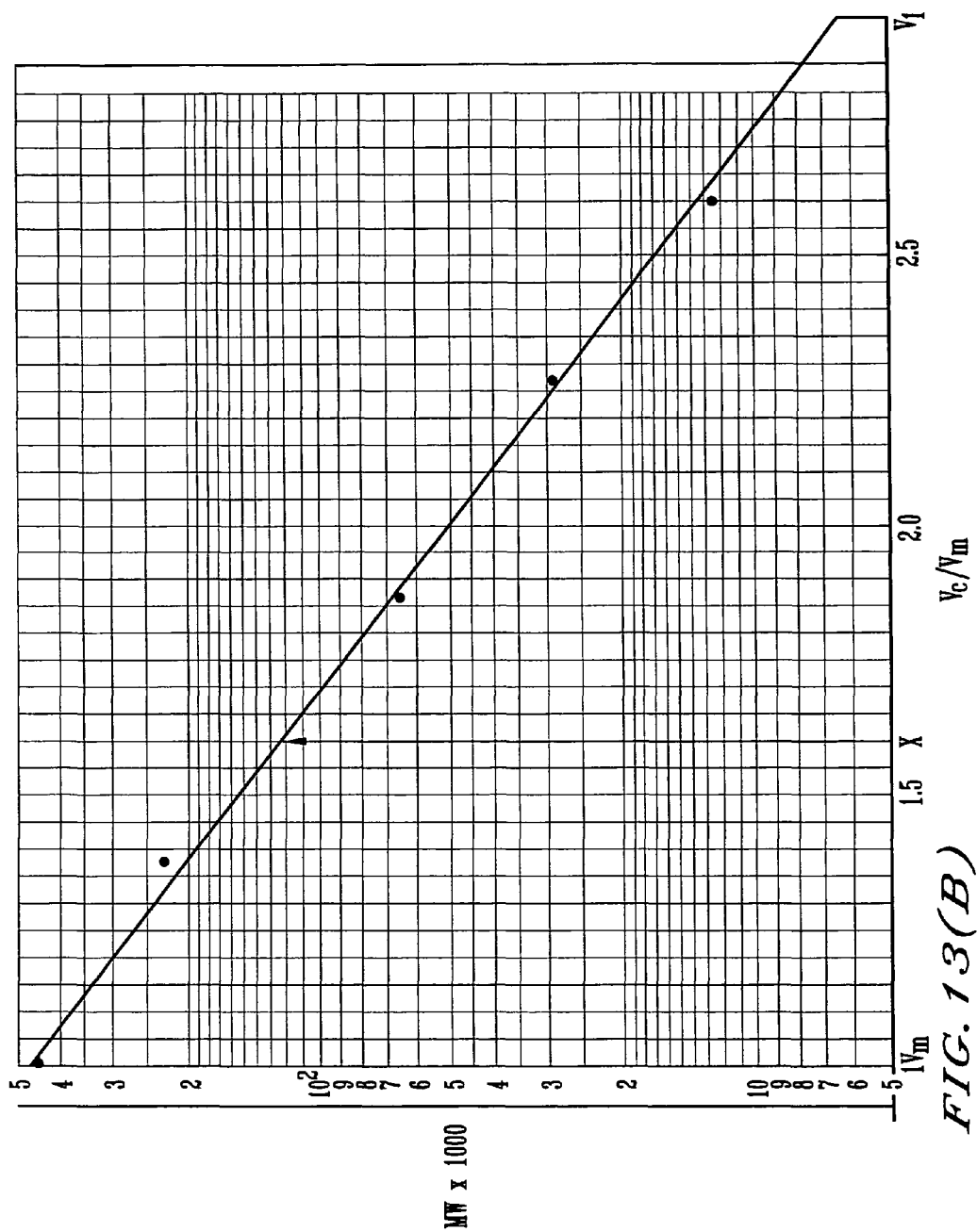

FIG. 13: calibrating of Superdex 200.

Figure 14:
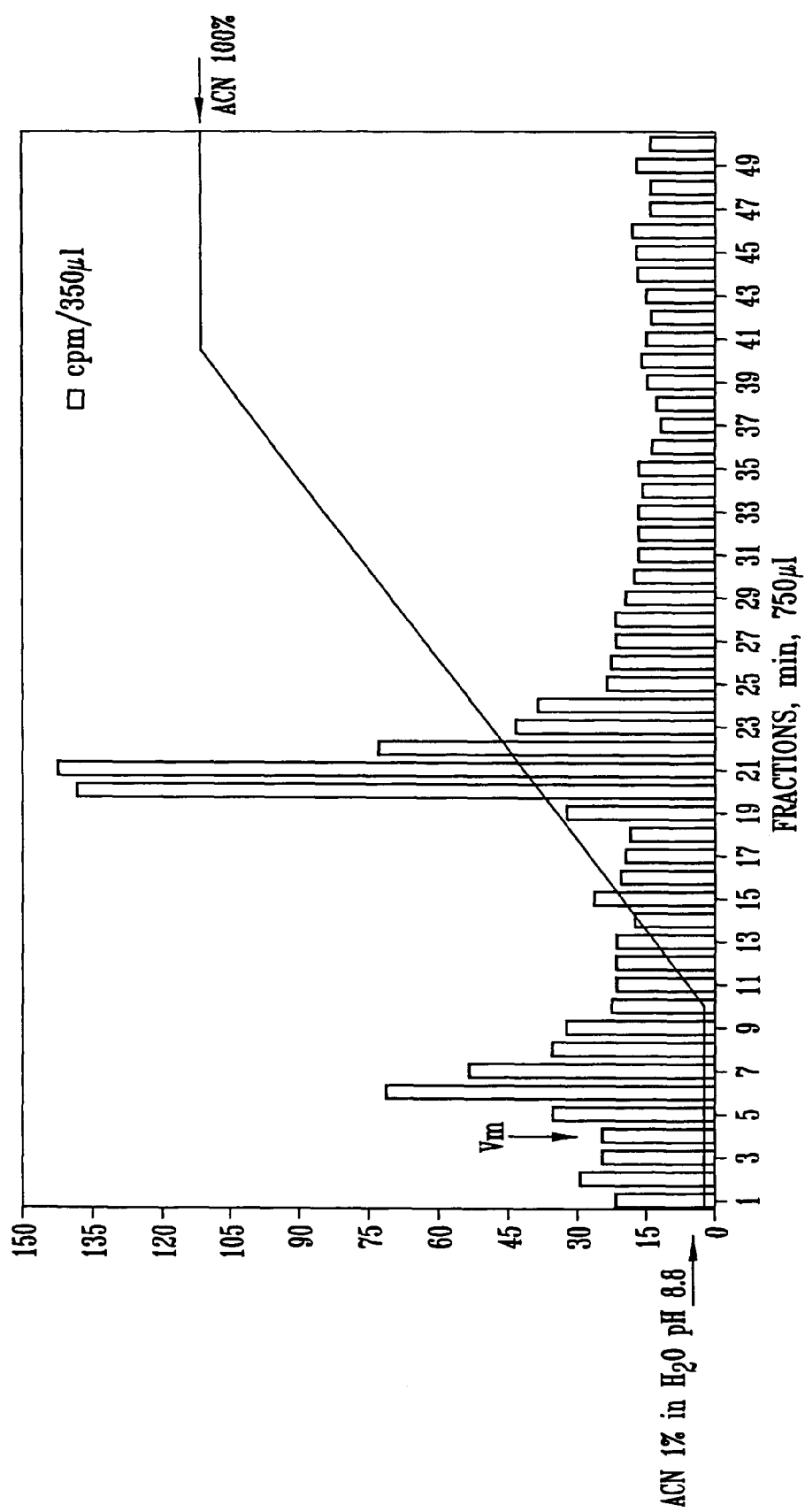

FIG. 14: FPLC $C_{18}$ reverse phase liquid chromatography (Rep RPC, Pharmacia).

IEF fractions of membrane preparations of outer medulla of kidney.

Figure 15:
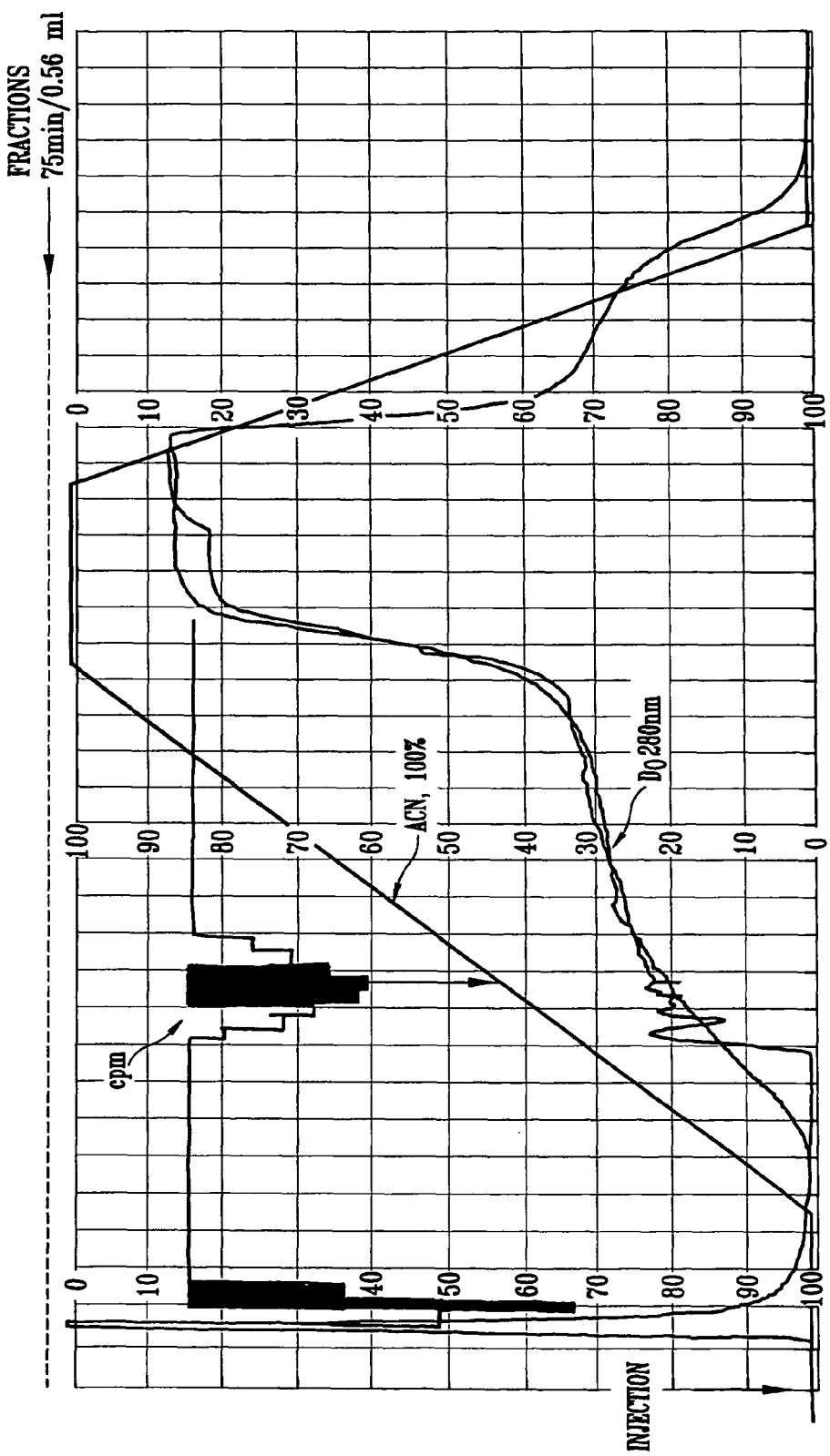

FIG. 15: FPLC RP-18 chromatographic profiles of radioactivity, optical density at 280 nm, acetonitrile concentration and fractionating at 0.75 ml/min.

Representative chromatogram of IEF fractions of solubilized membrane preparations of outer medulla of kidney.

Figure 16:
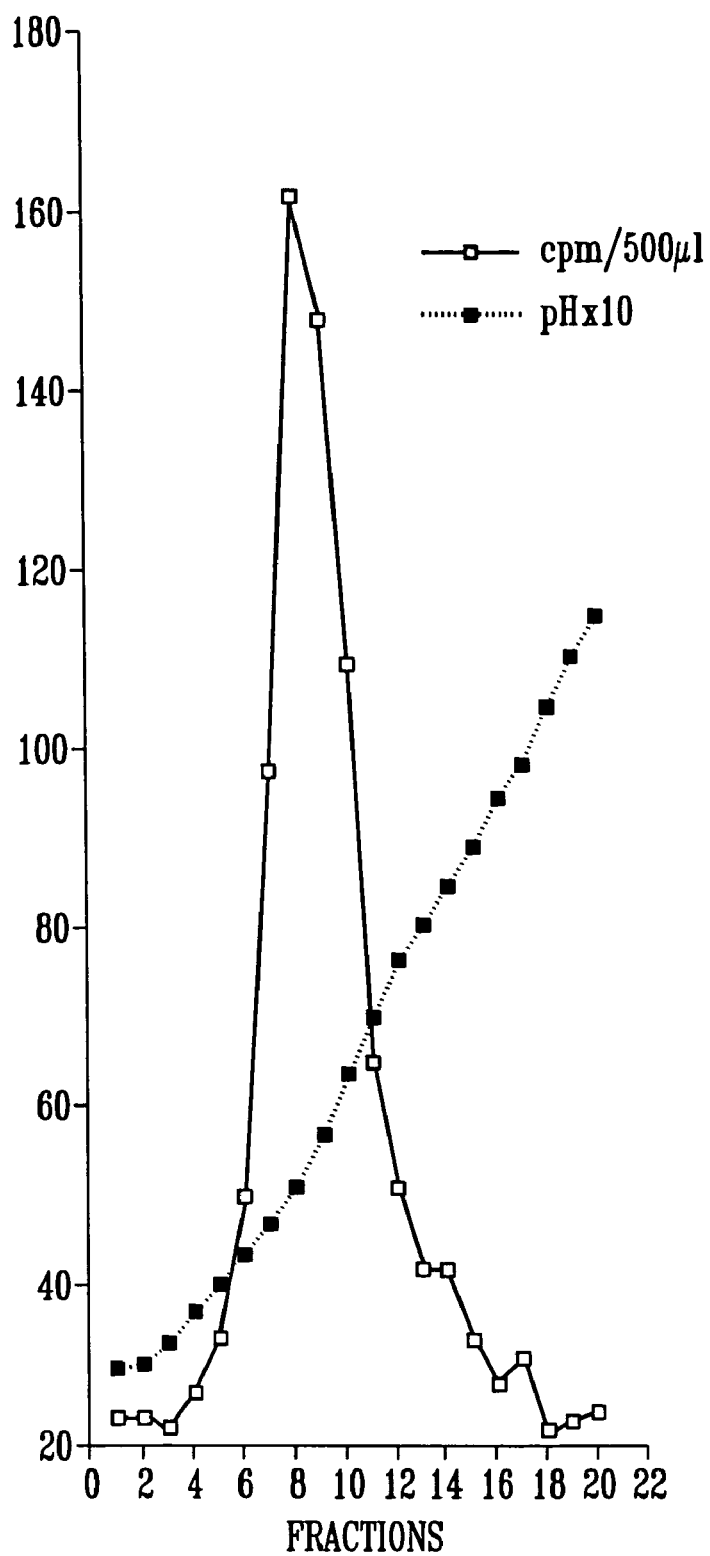

FIG. 16: Profile of preparative isoelectrofocusing of membrane preparations solubilized in SB14/SB201 of outer medulla of kidney.

Figure 17:
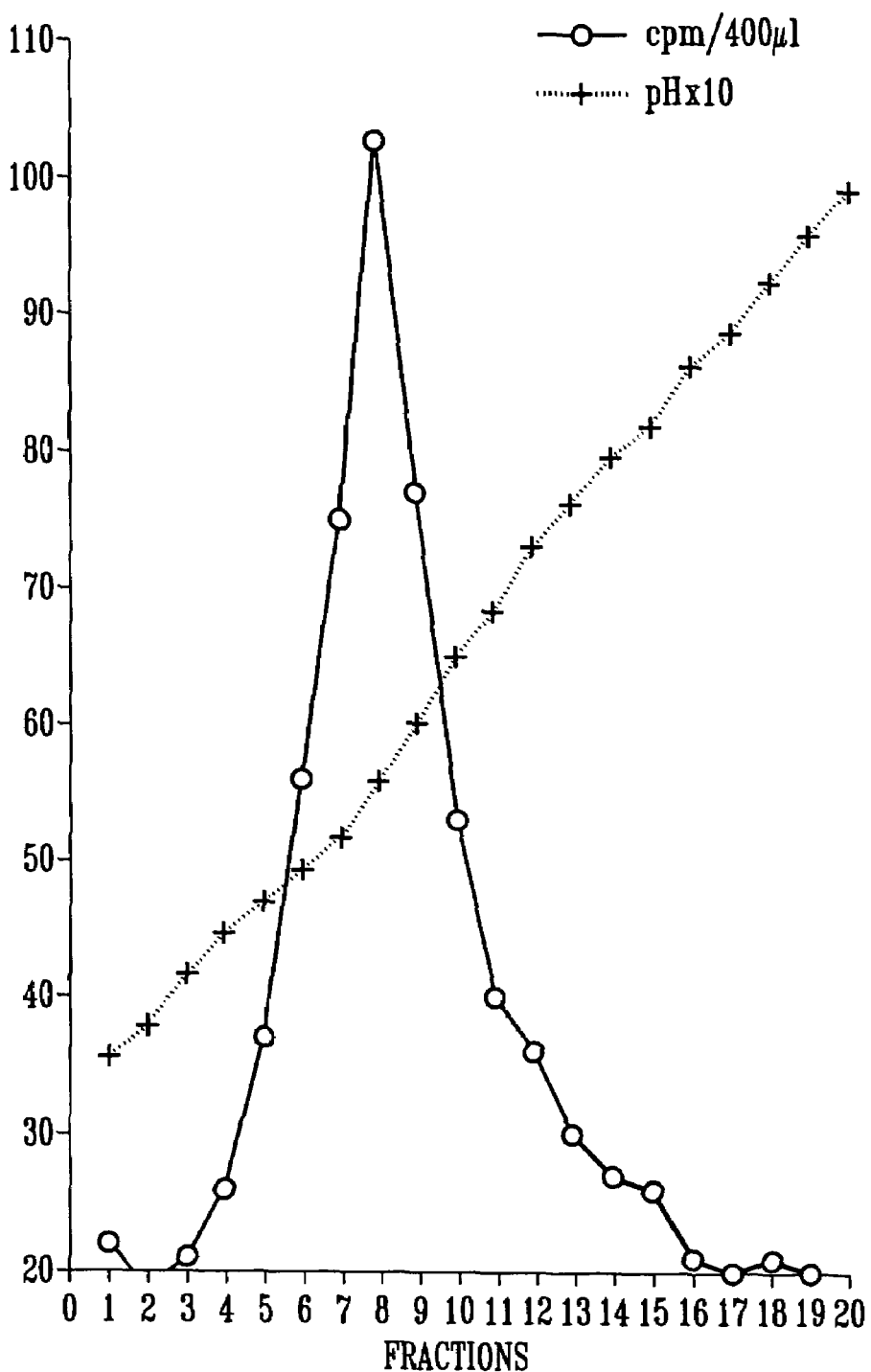

FIG. 17: Membrane preparations of pancreatic lobules solubilized in SB14/SB201.

Figure 18A:
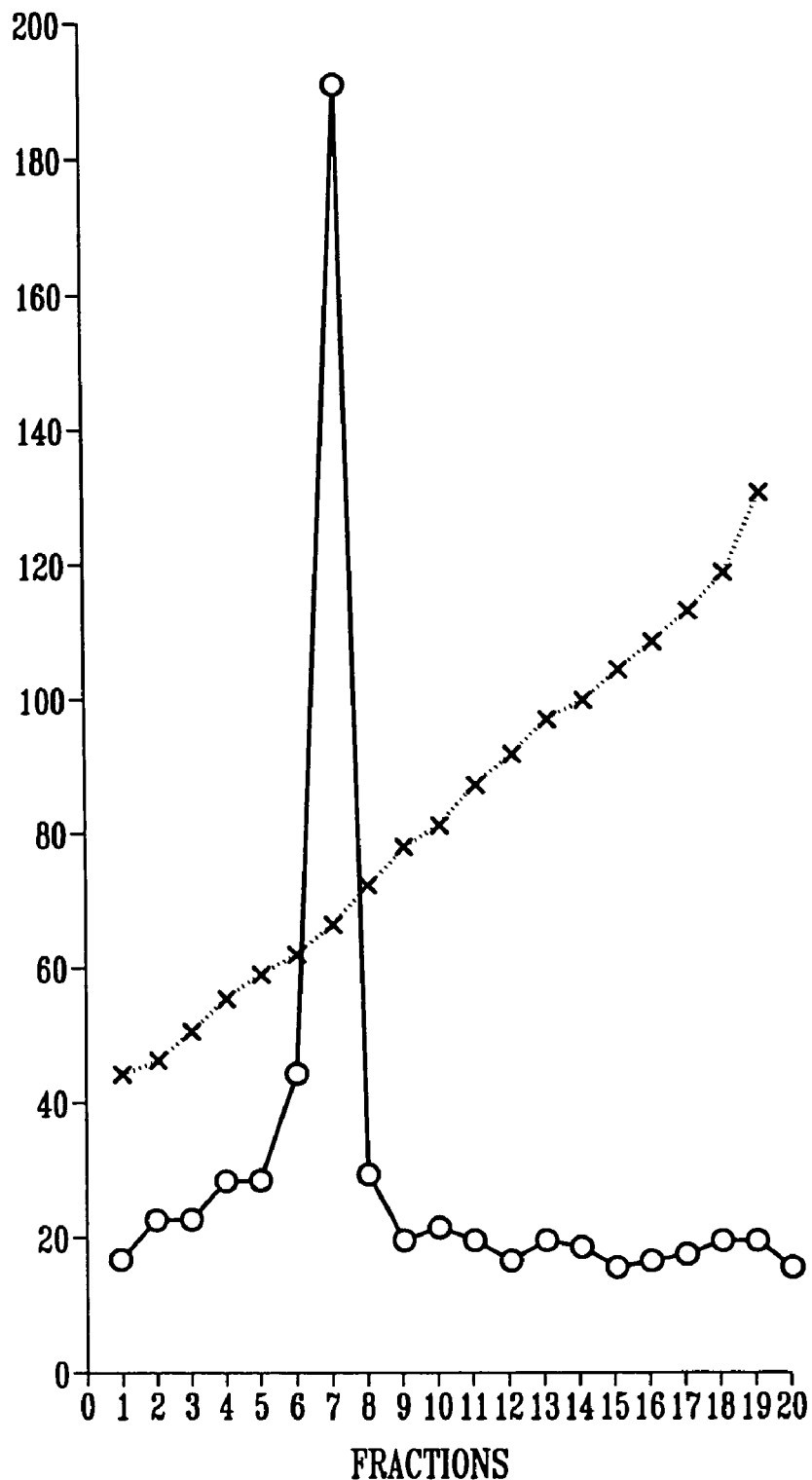
Figure 18B:
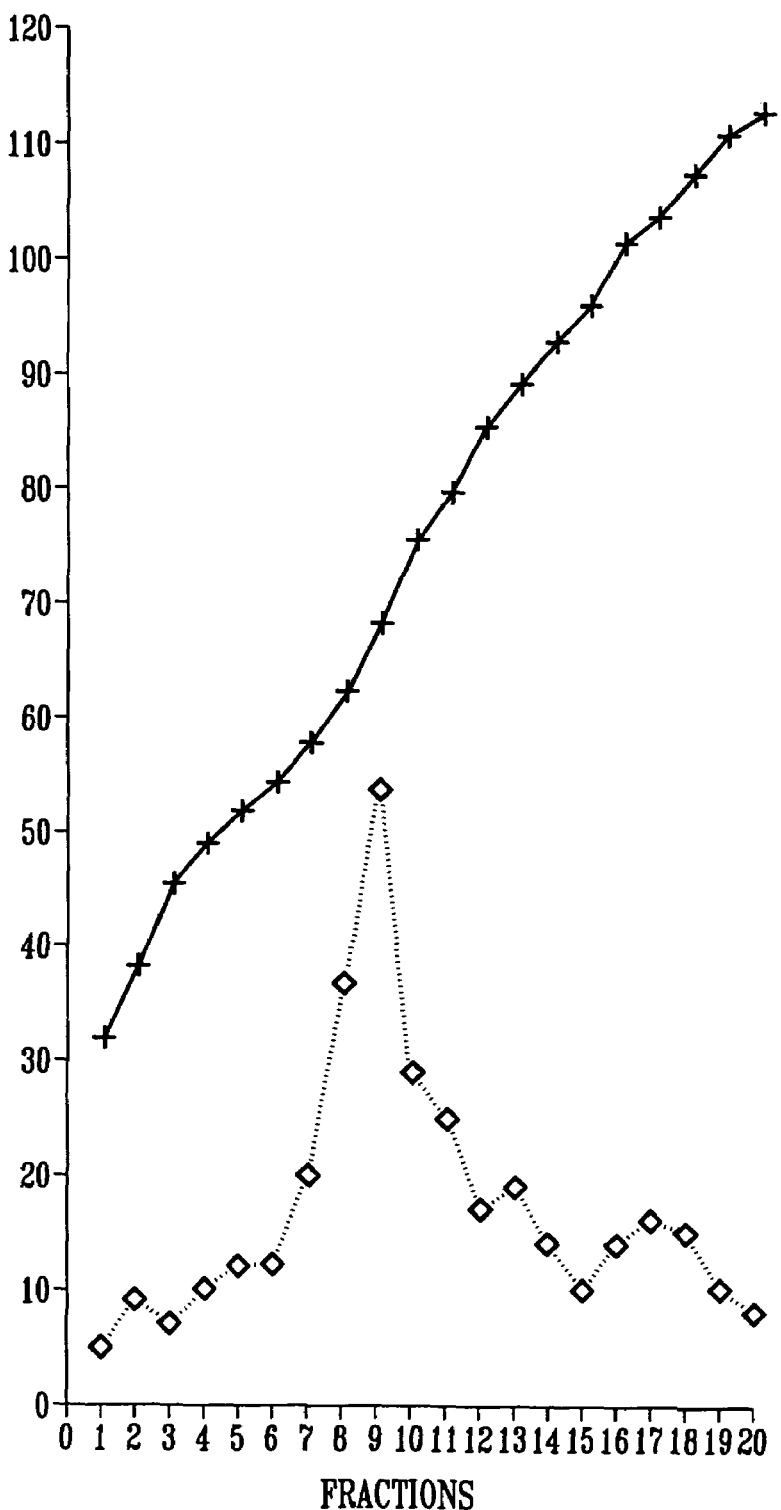
Figure 18C:
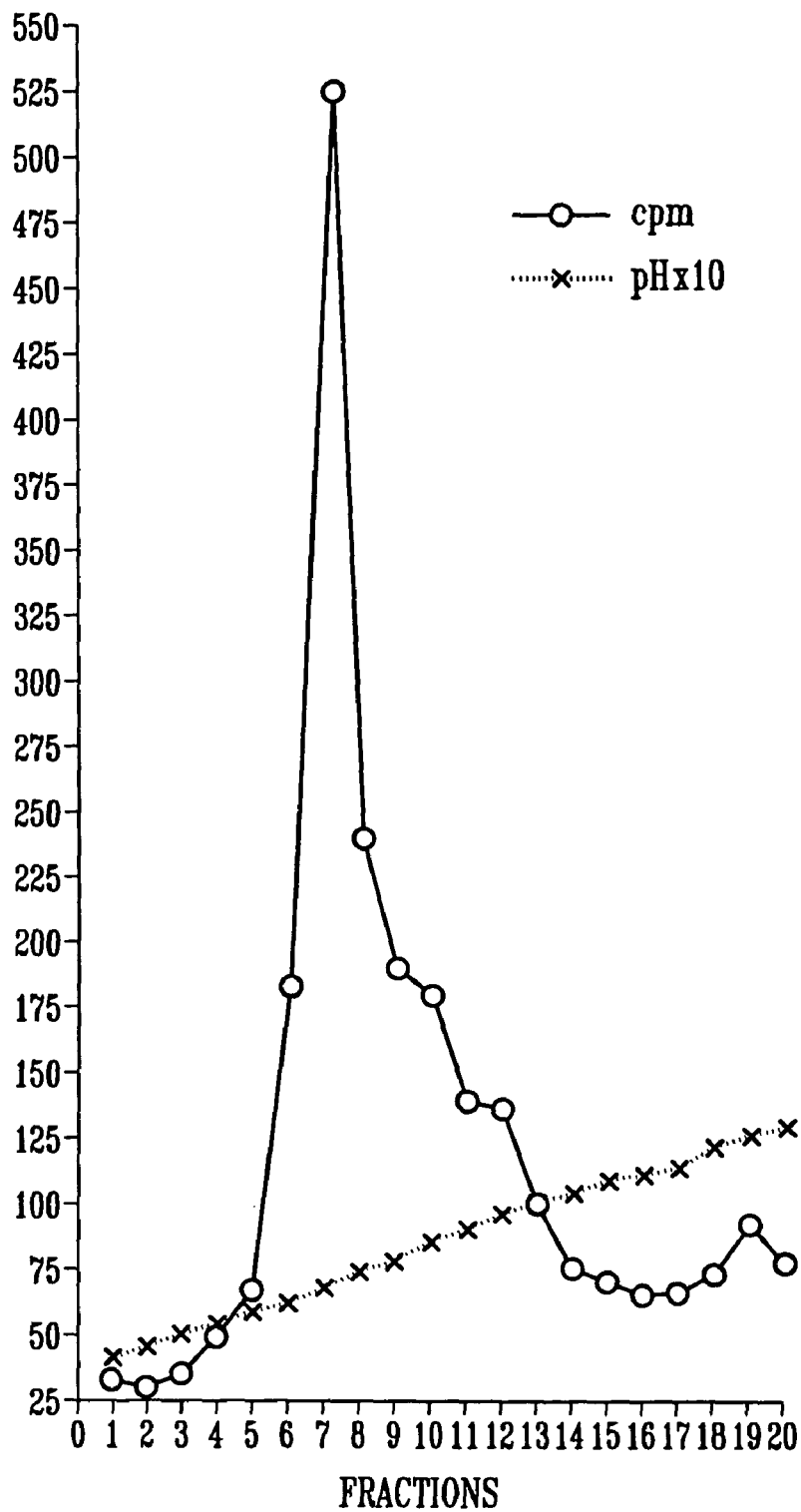

FIG. 18: IEF of membrane preparations of glandular gastric mucosa solubilized in SB14/SB201.

Figure 19:
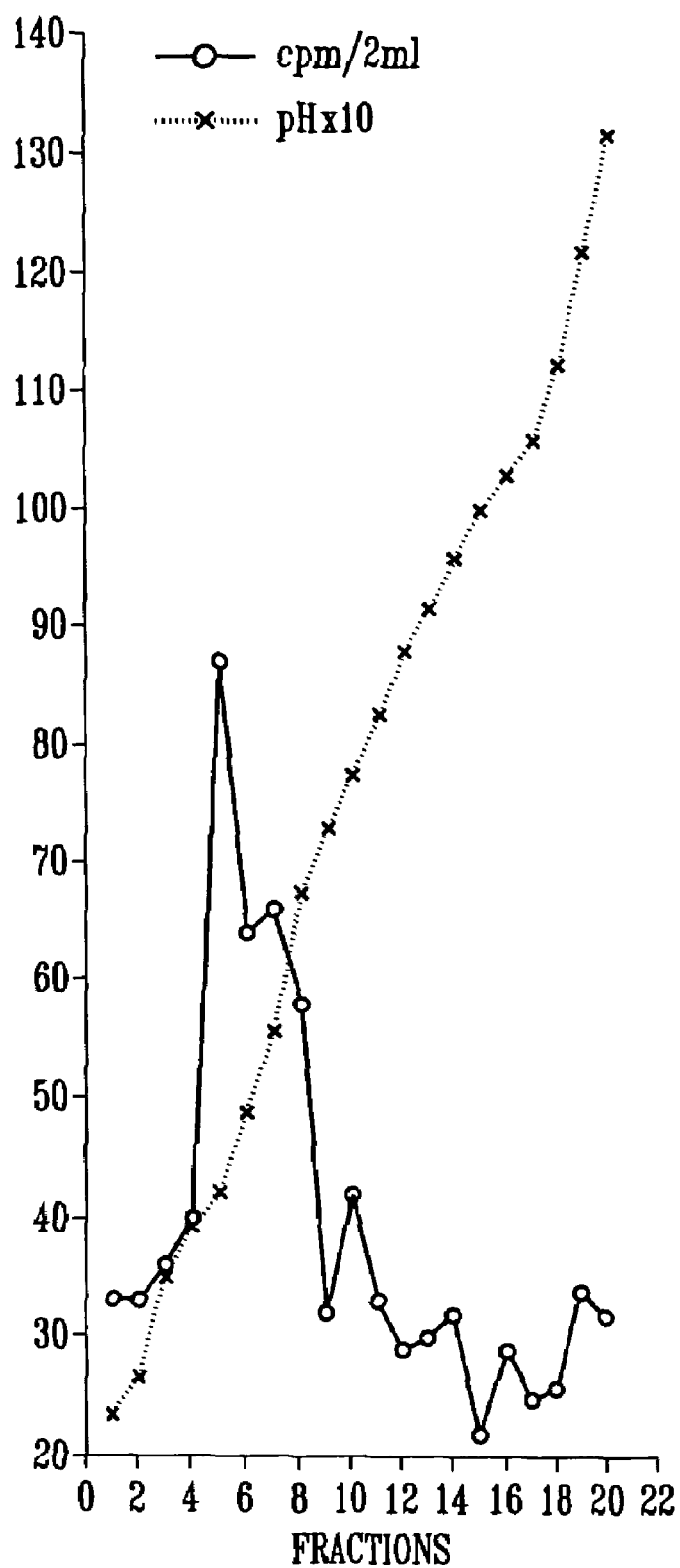

FIG. 19: IEF of membrane preparations of bone trabecular matrix solubilized in SB14/SB201.

Figure 20:
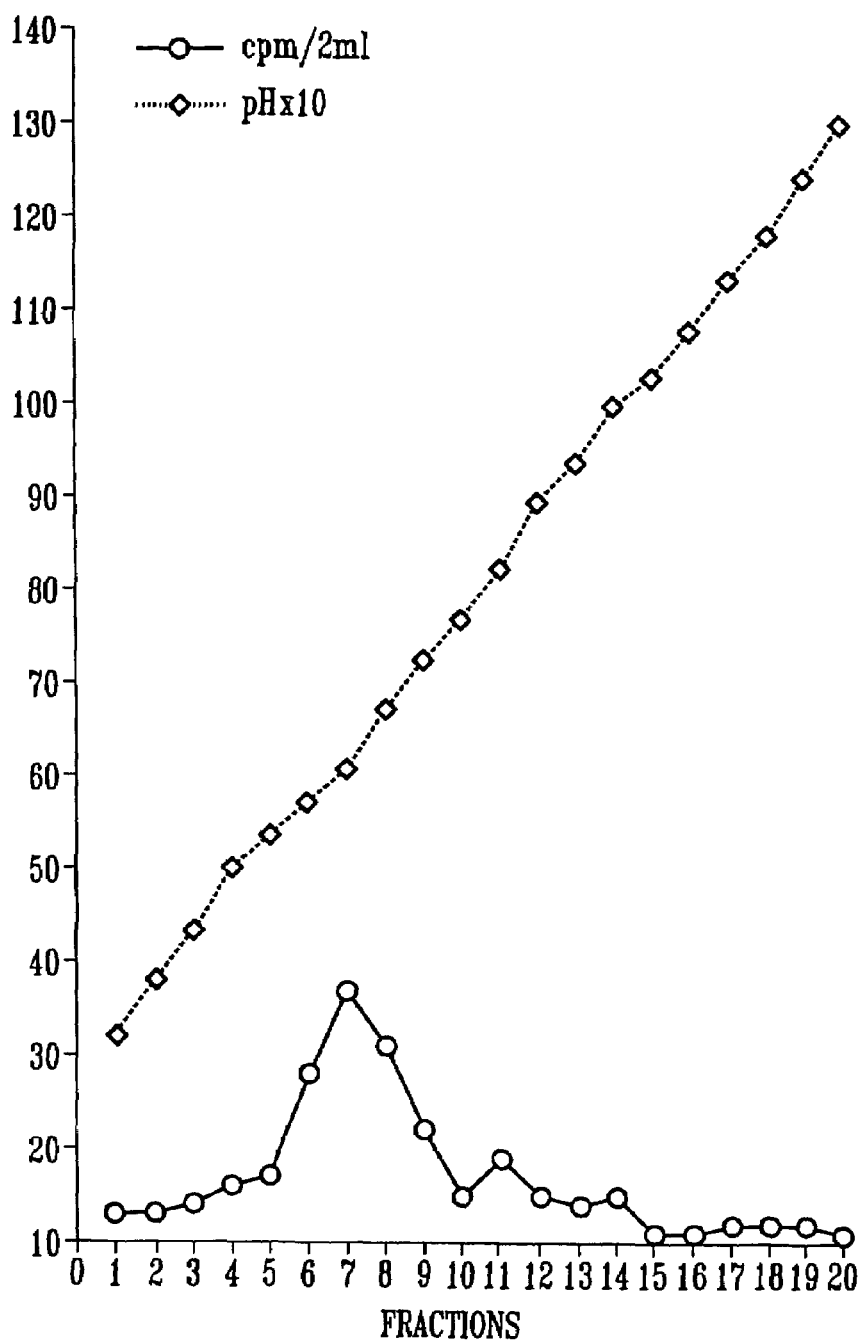

FIG. 20: IEF of membrane proteins of dentinal matrix solubilized in SB14/SB201.

Figure 21:
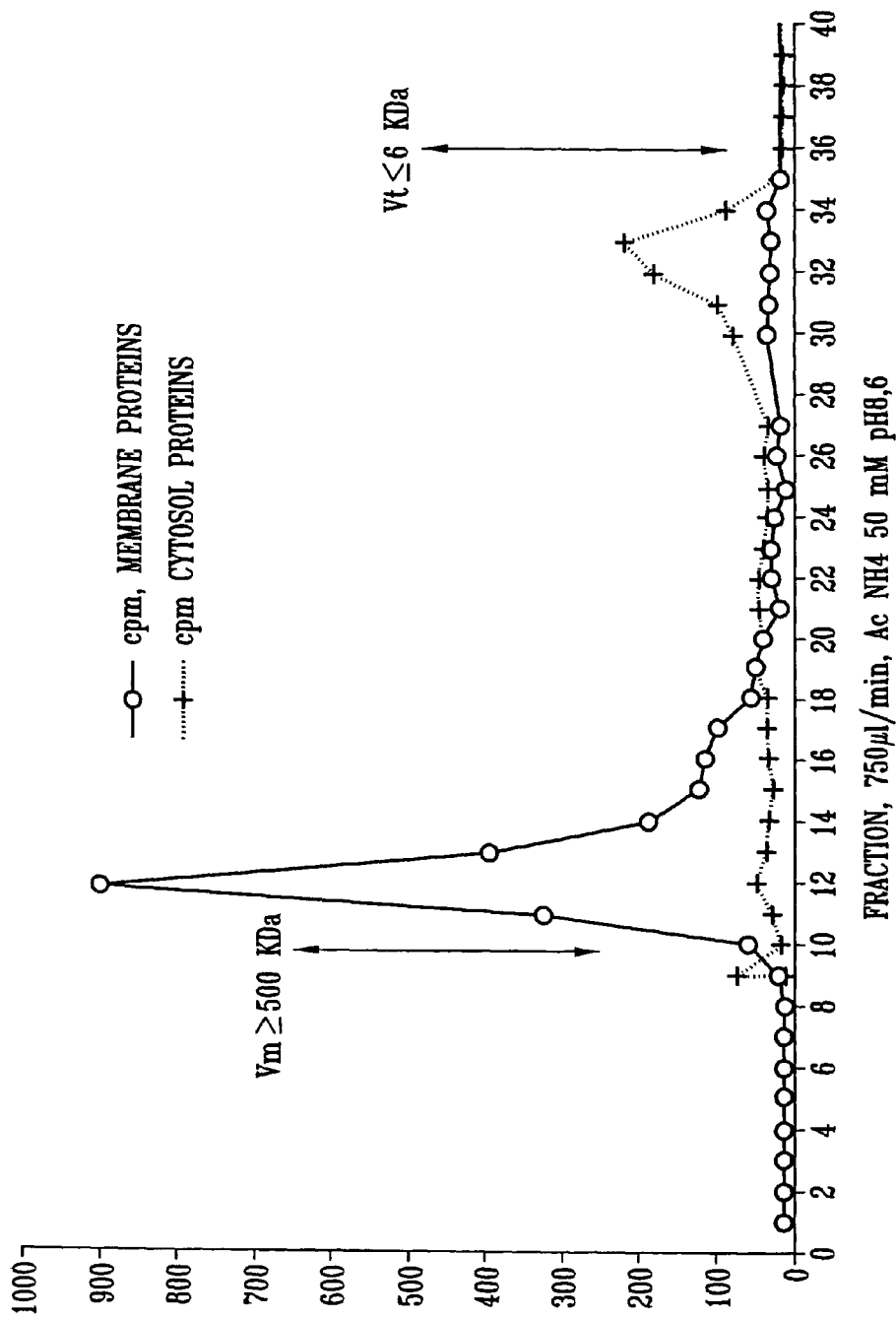

FIG. 21: Molecular Sieve (Superdex 200) of cytosolic and membrane fractions of outer medulla of kidney solubilized in detergent.

Figure 22A:
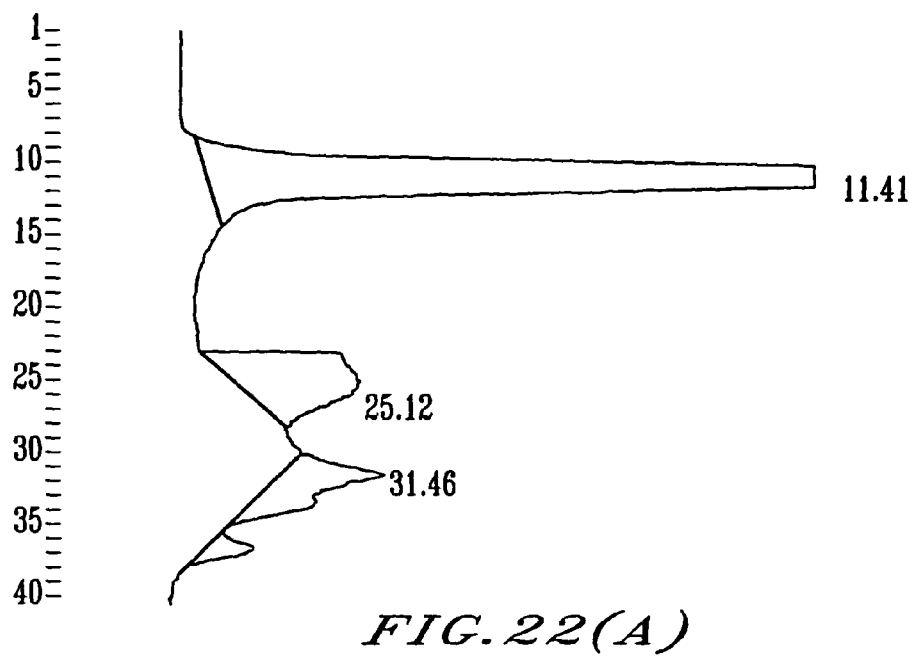
Figure 22B:
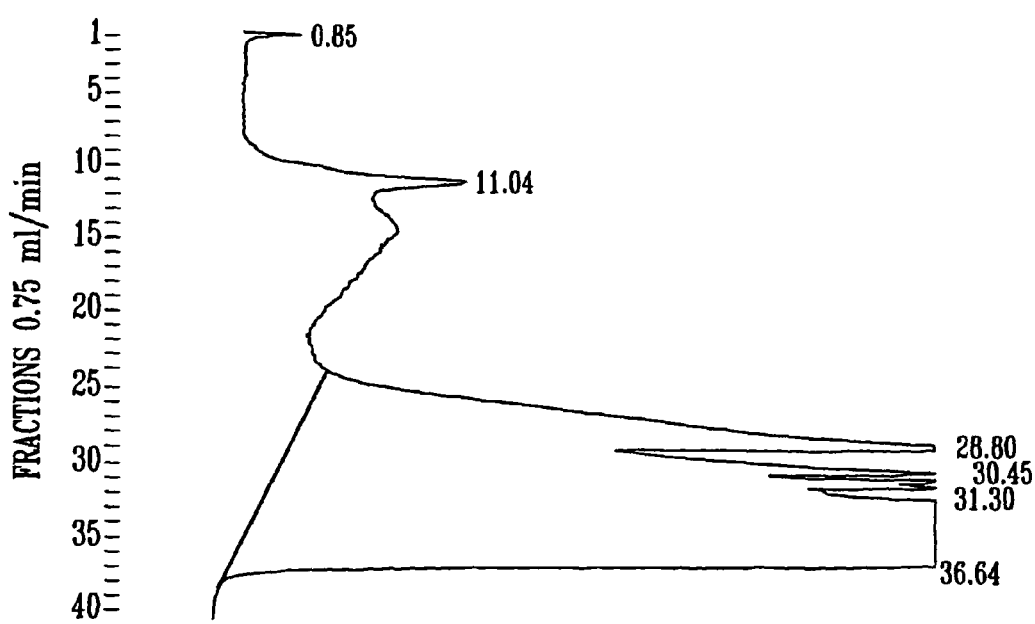

FIG. 22: Chromatographic profiles corresponding to FIG. 21 of OD at 274 nm and fractionating at 0.75 ml/min.

A: solubilized membrane fraction

B: cytosolic fraction of outer medulla of kidney.

Figure 23:
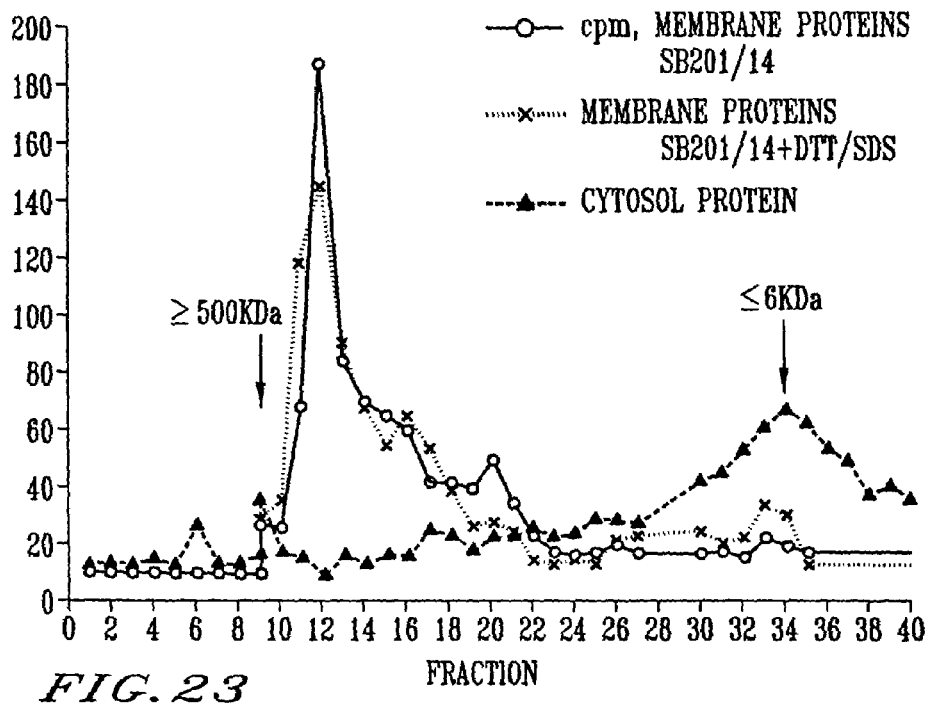

FIG. 23: Profile of molecular sieve (Superdex 200) of pancreatic membrane fractions solubilized in SB14/SB201.

Figure 24:
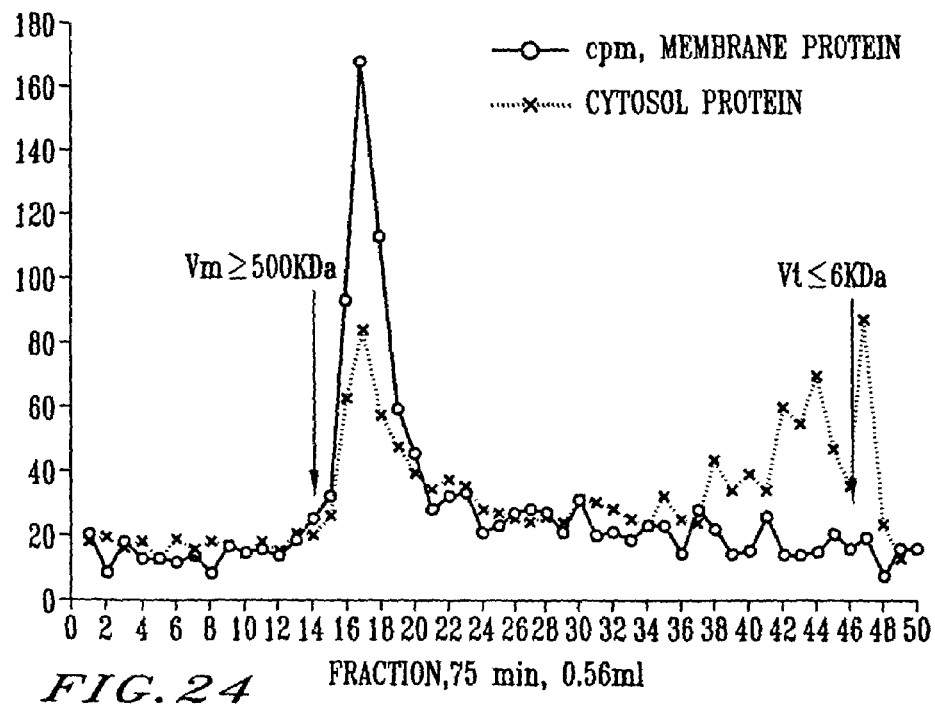

FIG. 24: Profile of molecular sieve (Superdex 200) of membrane proteins of glandular gastric mucosa solubilized in SB14/SB201.

DETAILED DESCRIPTION OF PREFERRED EMBODIMENTS

The peptides used according to the present invention may be prepared in a conventional manner by peptide synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis the technique described by Merrifield may be used in particular. Alternatively, the technique described by Houbenweyl in 1974 may also be used.

In order to produce a peptide chain using the Merrifield process, a highly porous resin polymer is used, on which the first C-terminal amino acid of the chain is fixed. This amino acid is fixed to the resin by means of its carboxyl groups and its amine function is protected, for example, by the t-butyloxycarbonyl group.

When the first C-terminal amino acid is thus fixed to the resin, the protective group is removed from the amine function by washing the resin with an acid. If the protective group for the amine function is the t-butyloxycarbonyl group, it may be eliminated by treating the resin with trifluoroacetic acid.

The second amino acid which supplies the second residue of the desired sequence is then coupled to the deprotected amine function of the first C-terminal amino acid fixed to the chain. Preferably, the carboxyl function of this second amino acid is activated, for example, using dicyclohexylcarbodiimide, and the amine function is protected, for example, using t-butyloxycarbonyl.

In this way, the first part of the desired peptide chain is obtained, which comprises two amino acids, the terminal amine function of which is protected. As before, the amine function is deprotected and the third residue can then be fixed, under similar conditions, to those used in the addition of the second C-terminal amino acid.

Thus, the amino acids which are to form the peptide chain are fixed, one after another, to the amine group, which is previously deprotected each time, to the portion of the peptide chain already formed, which is attached to the resin.

When all the desired peptide chain is formed, the protecting groups are eliminated from the various amino acids which constitute the peptide chain and the peptide is detached from the resin, for example using hydrofluoric acid.

The peptides thus synthesized may also be a polymer of the XQHNPR (SEQ ID NO: 14) peptide, that contains 2 to 20 monomer units of the amino acid sequence XQHNPR (SEQ ID NO: 14), preferably 4 to 15 monomer units and more preferably 5 to 10 monomer units. The polymers may be obtained by the technique of Merrifield or any other conventional peptide polymer synthesis method well known by a person skilled in the art.

The peptides thus obtained may be purified, for example by high performance liquid chromatography, such as reverse phase and/or cationic exchange HPLC, as described by Rougeot et al. in 1994.

The peptides used in the therapeutic method according to the present invention may also be obtained using genetic engineering methods. The nucleic acid sequence of the cDNA encoding the complete 146 amino acid SMR1 protein has been described in the PCT Patent Application No. WO 90/03891 (Rougeon et al.) For the biologically active peptide derivatives of the XQHNPR (SEQ ID NO: 14), a person skilled in the art will refer to the general literature to determine which appropriate codons may be used to synthesize the desired peptide.

For the genetic expression of the XQHNPR (SEQ ID NO: 14) peptide, the following nucleotide sequence may be used, based on the general codon usage in mammals:

Peptide (SEQ ID NO: 7)

V R G P R R Q H N P R GTC AGA GGC CCA
AGA AGA CAA CAT MT CCT AGA DNA (SEQ
ID NO: 8)

or a nucleotide sequence hybridizing with the above sequence under stringent conditions and which encodes a peptide having qualitatively the same mineral ion regulation activity than the QHNPR (SEQ ID NO: 1) peptide.

By stringent hybridization conditions according to the present invention, is intended the following conditions:

The hybridization step is performed at 65° C. in the presence of 6×SSC, 5×Denhardt solution, 0.5% SDS and 100 µg/ml salmon sperm DNA. The washing steps consist of:
- washing twice during 5 min at 65° C. in a 2×SSC and 0.1% SDS buffer;
- washing once during 30 min at 65° C. in a 2×SSC and 0.1% SDS buffer;
- washing once during 10 min at 65° C. in a 0.1×SSC and 0.1% SDS.

The expression of the polynucleotide that encodes the XQHNPR (SEQ ID NO: 14) may be optimized, according to the organism in which the sequence has to be expressed and the specific codon usage of this organism (mammal, plant, bacterium etc.) For bacteria and plants, respectively, the general codon usages may be found in European Patent Application No. EP-0359472 (Mycogen).

It is now easy to produce proteins in high amounts by genetic engineering techniques using, as expression vectors, plasmids, phages or phagemids. The polynucleotides that code for the polypeptides of the present invention are inserted in an appropriate expression vector in order to produce the polypeptide of interest in vitro. Consequently, the present invention also embraces the production by genetic engineering techniques of the SMR1 protein or one of its maturation products. The SMR1 protein (which can be considered as the precursor of the different maturation products) is processed by furin. Furin is a subtilisin-like convertase involved in pos-translation endoproteolytic processing of various pro-hormones. Thus, furin may be advantageously used in combination with a precursor of the XQHNPR (SEQ ID NO: 14) peptide in order to obtain the corresponding maturation product.

Thus, a method for producing the SMR1 protein or one of its maturation products such as a XQHNPR (SEQ ID NO: 14) peptide of the invention, or also a peptide containing "equivalent" amino acids as described above comprises the steps of:
a) Optionally amplifying the nucleic acid coding for the desired polypeptide using a pair of primers specific for the SMR1 genomic or cDNA sequence (by SDA, TAS, 3SR NASBA, TMA, LCR, RCR, CPR, Q-beta replicase or PCR);
b) Inserting the nucleic acid coding for SMR1 protein interest in an appropriate vector;
c) Inserting the nucleic acid coding for furin in a suitable vector, said vector being the vector of step b) or said vector being a vector different form the vector of step b).
d) culturing, in an appropriate culture medium devoid of serum, a cell host previously transformed or transfected with the recombinant vector of step b) and c);
e) harvesting the culture medium thus conditioned and the cell host, for example by lysing the cell host by sonication or by an osmotic shock;
f) separating or purifying, from the culture medium, or from the pellet of the resultant host cell lysate, the thus produced polypeptide of interest.
g) Characterizing the produced peptide of interest.
h) Optionally assaying for the specific recognition of the peptide by a polyclonal or a monoclonal antibody directed against the XQHNPR (SEQ ID NO: 14) peptide, specifically against the QHNPR (SEQ ID NO: 1) peptide.

A suitable vector for the expression of the SMR1 protein and the convertase protein above-defined is baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*.

Another suitable vector for performing the above-described process is a vaccinia virus vector. In this specific embodiment, BSC-40 or LoVo are used for the transfection and culture steps.

The purification of the recombinant protein may be realized by passage onto a Nickel or Copper affinity chromatography column. The Nickel chromatography column may contain the Ni-NTA resin (Porath et al., 1975).

The PCR amplification reaction was described by Saiki et al. in 1985; The SDA technique was described by Walker et al. in 1992 and was improved by Spargo et al. in 1996; The TAS amplification reaction was described by Kwoh et al. in 1989; The 3SR technique was described by Guatelli et al. in 1990; The NASBA technique was described by Kievitis et al. in 1991; The LCR reaction was described by Landergen in 1991 and improved by Barany et al. in 1991; The RCR technique was described by Segev in 1992; The CPR technique was described by Duck et al. in 1990. Ref Co-transfection with convertase.

The peptides produced by genetic engineering methods according to the invention may be characterized by binding onto an immunoaffinity chromatography column on which polyclonal or monoclonal antibodies directed to XQHNPR (SEQ ID NO: 14) have previously been immobilized.

More preferably, the peptide of therapeutic value contained in the therapeutic compositions according to the present invention is purified by HPLC as described by Rougeot et al. in 1994. The reason to prefer this kind of peptide or protein purification is the lack of side products found in the elution samples.

The antibodies may be prepared from hybridomas according to the technique described by Kohler and Milstein in 1975. The polyclonal antibodies may be prepared by immunization of a mammal, especially a mouse or a rabbit, with a peptide according to the invention that is combined with an adjuvant of immunity, and then by purifying the specific antibodies contained in the serum of the immunized animal onto an affinity chromatography column on which has previously been immobilized the peptide that has been used as the antigen. A technique for preparing and using an immunoaffinity chromatography column was described, for example, by Bird et al. in 1984.

A preferred embodiment for preparing antibodies raised against the SMR1 protein or its maturation products is described hereafter, using the QHNPR (SEQ ID NO: 1) pentapeptide as an example. Briefly, the QHNPR (SEQ ID NO: 1) peptide is conjugated to egg albumin (Calbiochem) using the benzidine-bis-diazoted procedure described by Gregory et al. in 1967, the ratio of peptide residues to one molecule of ovalbumin being 5:1. Rabbits are injected at time 0 with 1 mg of the conjugated peptide. Two months after the primary injection, animals are injected with 0.5 mg of the conjugated peptide and a third injection of 0.5 mg of the same peptide is performed between two and four months after the second injection. Antiserum is harvested between two and four weeks following the third conjugated peptide injection and optionally purified onto an affinity chromatography column as previously described. Preferably the injection is an intradermally multi-points injection; generally ten points of injection are performed.

Other biologically active derivatives of the therapeutic peptides of the invention consist in molecules that are either or both structurally or chemically unrelated to the endogenous peptides but bind to the same specific targets and have an agonist or an antagonist activity. Preferably, the biologically active derivatives of the therapeutic peptides used in the therapeutic method according to the present invention are endowed with a longer in vivo half-life than their natural endogenous counterparts.

The methods that allow a person skilled in the art to select and purify the biologically active derivatives that bind to the same targets and have an agonist or an antagonist biological activity of the XQHNPR (SEQ ID NO: 14) peptide of the invention are described hereunder.

The biologically active derivative of the XQHNPR (SEQ ID NO: 14) peptide may be a protein, a peptide, a hormone, an antibody or a synthetic compound which is either a peptide or a non peptidic molecule, such as any compound that can be synthesized by the conventional methods of organic chemistry.

Selection of the biologically active derivatives of the XQHNPR (SEQ ID NO: 14) peptide of the invention is performed both in assessing the binding of a candidate ligand molecule to the known target cells or organs of the XQHNPR (SEQ ID NO: 14) peptide, specifically the QHNPR (SEQ ID NO: 1) pentapeptide, and in determining the metabolic changes induced by this candidate molecule on its target, such as the synthesis of the primary or secondary messenger metabolites as a result of a transduction signal via the protein kinases or adenylate cyclase and the activation of a protein of the G family.

The binding of the candidate molecule to primary culture cells, established cell lines or fresh tissue samples (cryosections or slices) is performed as described hereafter.

Binding assays of the candidate molecule are generally performed at a cold temperature (4° C.). However, variations of the standard procedure described below involving incubation at 37° C. are useful to assess the internalization and fate of the pentapeptide or one biologically active derivative candidate ligand molecule upon binding at the cell surface (Wakefield, 1987). In order to facilitate the reading of the hereinafter described protocol, QHNPR (SEQ ID NO: 1) pentapeptide is used instead of a biologically active derivative candidate molecule.

Accordingly, one object of the present invention is a process for screening ligand molecules that specifically bind to the target receptor for the XQHNPR (SEQ ID NO: 14) pentapeptide, comprising the steps of:
a) Preparing a confluent target cell culture monolayer or preparing a target organ specimen or a tissue sample;
b) Adding the candidate molecule to be tested in competition with half-saturating concentration of labeled pentapeptide;
c) Incubating the cell culture, organ specimen or tissue sample of step a) in the presence of the labeled candidate molecule during a time sufficient for the specific binding to take place;
d) Quantify the label specifically bound to the target cell culture, organ specimen or tissue sample.

Another object of the present invention is a process for determining the affinity of ligand molecules that specifically bind to the target receptor for the XQHNPR (SEQ ID NO: 14) pentapeptide, comprising the steps of:
a) Preparing a confluent target cell culture monolayer or preparing a target organ specimen or a tissue sample;
b) Adding the candidate molecule to that which has been previously labeled with a radioactive or a nonradioactive label;
c) Incubating the cell culture, organ specimen or tissue sample of step a) in the presence of the labeled candidate molecule during a time sufficient for the specific binding to take place; and
d) Quantify the label specifically bound to the target cell culture, organ specimen or tissue sample.

The candidate ligand molecule may be radioactively labeled ($^{32}P$, $^{35}S$, $^{3}H$, $^{125}I$ etc.) or nonradioactively labeled (biotin, digoxigenin, fluorescein etc.)

Specifically, the materials used to perform the above binding process are:
Binding buffer I: 128 mM NaCl, 5 mM KCl, 5 mM $MgSO_4$, 1.2 mM CaCl, 50 mM HEPES, pH 7.5, BSA (between 0.1 and 2 mg/ml).
Binding buffer II: Dulbecco's modified Eagle's medium (Gibco BrI) supplemented with 25 mM HEPES, pH 7.5, and 2 mg/ml of BSA (between 0.1 and 2 mg/ml).
$^{3}H$-Labeled or $^{125}I$-Labeled QHNPR (SEQ ID NO: 1): An appropriate dilution is prepared in binding medium immediately before each experiment. This dilution should be made in a Minisorb™ plastic tube (Nunc). the $^{3}H$-Labeled QHNPR (SEQ ID NO: 1) has a specific radioactivity of 60 Ci/mmole (CEA, Saclay, France). The 1251 labeling technique is hereafter described.
QHNPR (SEQ ID NO: 1): Diluted appropriately using the same buffer and conditions as for $^{3}H$-Labeled or $^{125}I$-Labeled QHNPR (SEQ ID NO: 1).
Cell solubilization buffer: 1% (v/v) Triton X-100, 10% (v/v) glycerol, 25 mM HEPES, pH 7.5,1 mg/ml BSA.
Cells: 2 or 10-$cm^2$ confluent monolayers preferably seeded in multiwell plates are used. Assays involving cell types that detach easily from the substratum should be performed with cell suspensions. Single cell suspensions can be obtained by mechanical detachment (by pipetting) or brief exposure at 37° C. to detachment buffer containing 1 mM EDTA, 128 mM NaCl, 5 mM glucose, 25 mM HEPES, pH 7.4, 2 mg/ml BSA.

The radio-iodinated label of QHNPR (SEQ ID NO: 1) is realized as follows: The peptide QHNPR (SEQ ID NO: 1) is labeled according to the method of Greenwood et al., 1963, using 1 mCi Na $^{125}I$ (Amersham), 0.8 µg (1 nmol) pentapeptide and 15 µg chloramine T (Fluka) in 50 µl sodium borate, pH 8. After a 2 min-reaction, the mixture is chromatographed by GF05 gel filtration (Pharmacia-LKB) to isolate the $^{125}I$-Labelled pentapeptide and is subsequently chromatographed on reverse-phase porapak Q™ (Waters-Millipore) to elute the mono-iodinated-labelled labeled pentapeptide. The specific radioactivity, corresponding to one atom of radioiodine/peptide molecule, is estimated as 1500 Ci/mmol.

The assay, by itself, comprises the following steps:
a) Wash cell monolayers with binding buffer. Binding buffers I and II can be used interchangeably in assays performed at 4° C., but binding buffer II should be used in assays involving an incubation step at 37° C. After washing once, monolayers are allowed to equilibrate with binding buffer for 30 min at 4° C.
b) Aspirate buffer and add ice-cold binding buffer to plates on ice. The volume of buffer is about 1 ml/2-$cm^2$ well.
c) Add $^{3}H$-Labeled or $^{125}I$-Labeled QHNPR (SEQ ID NO: 1) diluted approximately in a small volume of binding buffer. Concentrations of ³H-Labeled or ¹²⁵I-Labeled QHNPR (SEQ ID NO: 1) in the pH range defined by the saturation curve (near the dissociation constant Kd). If desired, the ³H-Labeled or ¹²⁵I-Labeled QHNPR (SEQ ID NO: 1) may be incorporated in the buffer used in step b) before addition to the wells. Immediately before or after addition of ¹²⁵I-Labeled QHNPR (SEQ ID NO: 1), add unlabeled QHNPR (SEQ ID NO: 1) to those wells that require it. QHNPR (SEQ ID NO: 1) is used for two purposes. Increasing concentrations of QHNPR (SEQ ID NO: 1) are used to supplement the tracer concentration of ³H-Labeled or ¹²⁵I-Labeled QHNPR (SEQ ID NO: 1) in experiments designed to establish the saturation curve of QHNPR (SEQ ID NO: 1) binding to the cells. Increasing concentrations of QHNPR (SEQ ID NO: 1) or of the candidate ligand molecule are also used in the competitive binding receptor method. Additionally, a 50-fold or larger excess of unlabeled QHNPR (SEQ ID NO: 1) is used in all experiments to determine the amount of ¹²⁵I-Labeled QHNPR (SEQ ID NO: 1) which is non-specifically bound. This determination is based on the assumption that ³H-Labeled or ¹²⁵I-Labeled QHNPR (SEQ ID NO: 1) and QHNPR (SEQ ID NO: 1) compete for binding to relevant high-affinity sites, but not to nonspecific sites on the surfaces of cells or dishes.

d) Incubate assays for about 1.0 hour at 4° C. on a platform oscillating at 120 cpm.

e) Aspirate the medium. Wash cultures five times with ice-cold binding buffer I.

f) Add solubilization buffer (0.5 or 1.5 ml for 2- or 10-cm² wells, respectively). Incubate 40 min at 4° C.

g) Count radioactivity in the soluble extracts. To determine specific binding, subtract the counts per minute obtained in wells incubated with ³H-Labeled or ¹²⁵I-Labeled QHNPR (SEQ ID NO: 1) in the presence of excess QHNPR (SEQ ID NO: 1) from the counts per minute in wells incubated with ³H-Labeled or ¹²⁵I-Labeled QHNPR (SEQ ID NO: 1) alone. Count an aliquot of each ³H-Labeled or ¹²⁵I-Labeled QHNPR (SEQ ID NO: 1) dilution used in the experiment to determine specific radioactivity values. Count the number of cells per well to determine the amount of QHNPR (SEQ ID NO: 1) bound per cell.

By about one hour incubation according to step a) above, it is intended a time period of incubation that is sufficient for the QHNPR (SEQ ID NO: 1) or labeled QHNPR (SEQ ID NO: 1) to bind to its specific target sites on the cell, taking into account that the assay is performed at a temperature of 4° C., thus at a temperature for which the membrane fluidity is low. Consequently, the appropriate incubation time period is comprised between 1 and 12 hours (overnight).

Other receptor binding methods may also be used in order to select biologically active derivatives of the XQHNPR (SEQ ID NO: 14) peptide of the invention such as those described by Whitcomb et al. in 1993, Epelbaum et al. in 1993, Ricci et al. in 1993, Loring et al. in 1993, Walsh et al. in 1995, Roberts et al. in 1995 or also Wu et al. in 1996 the binding assays described in the aforementioned articles being herein incorporated by reference.

In order to assess the biological activity of a candidate ligand molecule of interest for the purpose of the present invention that has been positively selected according to the previously described binding assay and in order to determine if this selected competitive ligand molecule acts as an agonist or as an antagonist molecule of the XQHNPR (SEQ ID NO: 14) peptide of the invention, different metabolic assays may be performed. Hereinafter is described an adenylate cyclase assay that is performed either on primary cultures of target cells or on cell lines or on target tissue homogenates.

Briefly, tissue homogenates or cultured cells (1-100 µg protein) are incubated in 50 mM of Tris/HEPES buffer, pH 7.5, containing 1 mM Mg SO₄, 1 mM EGTA, 1 mM 3-isobutyl-1-methylxanthine, 0.1% (wuvol) BSA, 1 mM ATP, 25 mM creatine phosphate, 260 U/ml creatine kinase (E.C. 2.7.3.2), and 6.5 U/ml myokinase (E.C. 2.7.4.3) in a final vol of 100 µl for 10 min at 37° C. The reaction is stopped by addition of 100 µl 0.5% (wt/vol) SDS and boiling for 2 min. cAMP is extracted with Dowex 50WX-8 and analyzed by RIA (Stangi et al., 1993).

The quantity of cAMP produced in response to the presence of the candidate ligand molecule ($10^{-10}$-$10^{-5}$ M. range) is assessed as described above. A stimulation of adenylate cyclase activity which is equivalent, when used alone, or greater, when associated with suboptimal concentration of QHNPR (SEQ ID NO: 1), than the stimulation of adenylate cyclase activity induced by XQHNPR (SEQ ID NO: 14) alone, and more specifically QHNPR (SEQ ID NO: 1) alone, is considered as positive and the candidate ligand molecule is thus classified as an agonist of the XQHNPR (SEQ ID NO: 14) peptide of the invention.

In another embodiment of the screening method according to the present invention, the quantity of cAMP produced in the presence of both XQHNPR (SEQ ID NO: 14), specifically QHNPR (SEQ ID NO: 1), and the candidate ligand molecule is assessed. If the presence of the candidate ligand molecule is able to abolish or block the stimulation of adenylate cyclase activity induced by XQHNPR (SEQ ID NO: 14), specifically, QHNPR (SEQ ID NO: 1), then the candidate ligand molecule is classified among the antagonist compounds of the peptide according to the invention.

Indeed, quantification of the adenylate cyclase activity represents only one embodiment of the screening methods according to the present invention. A person skilled in the art would have understood that diverse metabolic changes of the cell physiology may be visualized in order to assess the agonist or antagonist activity of the candidate ligand molecule to be assayed. Other metabolic change quantification assays are also encompassed by the present invention, such as changes in the kinases activity, in the GTP-G proteins dependent activity, in the production of cell- or tissue-specific metabolites such as collagenase by osteogenic cell types.

Thus, the present invention also pertains to a process for screening ligand molecules that possess an agonist biological activity on the target receptor of the XQHNPR (SEQ ID NO: 14) pentapeptide, comprising the steps of:

a) Preparing a confluent target cell culture monolayer or preparing a target organ specimen or a tissue sample (cryosections or slices);

b) Incubating the cell culture, organ specimen or tissue sample of step a) in the presence of the candidate molecule ($10^{-10}$-$10^{-5}$ M) and of a submaximal concentration of QHNPR (SEQ ID NO: 1) (70 to 80% receptor saturation) during a time sufficient for the adenylate cyclase activation to take place;

c) Quantifying the adenylate cyclase activity present in the biological material of step a), respectively in the presence or in the absence of the candidate ligand molecule and in the presence or in the absence of a submaximal concentration of XQHNPR (SEQ ID NO: 14).

Another object of the present invention comprises a process for screening ligand molecules that possess an antagonist biological activity on the target receptor of the XQHNPR (SEQ ID NO: 14) pentapeptide, comprising the steps of:

a) Preparing a confluent target cell culture monolayer or preparing a target organ specimen or a tissue sample;

b) Incubating the cell culture, organ specimen or tissue sample of step a) in the presence of the XQHNPR (SEQ ID NO: 14) peptide, specifically the QHNPR (SEQ ID NO: 1) peptide, in the presence or in the absence of the candidate molecule during a time sufficient for the adenylate cyclase activation to take place, more particularly during 2-20 min, preferably 5-15 min, and most preferably 10 min;

c) Quantifying the adenylate cyclase activity present in the biological material of step a), respectively in the presence or in the absence of the candidate ligand molecule.

As mentioned above, another metabolic assay in order to assess the agonist or the antagonist activity of the candidate ligand molecule comprises incubating the ligand candidate in the presence of an osteogenic primary cell culture or cell line and determining, either or both quantitatively and qualitatively, the collagen produced in response to the in vitro stimulation (with $10^{-10}$-$10^{-5}$ M range concentration of the molecule to be tested).

As already mentioned, the binding assay and the metabolic assay, such as the adenylate cyclase assay, may be performed on primary cell cultures, on established cell lines or on fresh tissue slices, tissue cryosections or tissue homogenates.

A preferred cell line that is used in the screening methods according to the present invention is an osteogenic clonal mesodermal cell line from mouse, named C1, which is derived from mouse teratocarcinoma. It expresses the SV40 oncogenes under the control of the adenovirus E1a promoter (Chentoufi et al., 1993; Kellermann et al., 1990; Poliard et al., 1993; Poliard et al., 1995).

Other preferred cell lines consist in various clonal cell lines derived from the same mouse strain from which the clonal cell line C1 above has been initially derived, more specifically, clonal cell lines derived from the epithelial cell of renal proximal tubules.

Other preferred cell lines of different origin are the followings, which are publicly available from the ATCC cell culture collection:

1) Pancreas Cell Lines:
   AsPC-1 (ATCC N° CRL1682), human origin;
   Bx PC-3 (ATCC N° CRL 1687), human origin;
   Capan-1 (ATCC N° HTB 79), human origin;
   Capan-2 (ATCC N° HTB 80), human origin;
   PANC-1 (ATCC N° CRL1469), human origin;
   ARIP (ATCC N° CRL 1492), rat origin;
   ARIP (ATCC N° CRL 1674, rat origin;

2) Prostate Cell Lines:
   DU145 (ATCC N° HTB 81), human origin;
   LNCaP.FGC (ATCC N° CRL 1740), human origin;
   PC-3 (ATCC N° CRL 1435), human origin;

3) Kidney Cell Line:
   RAG (ATCC N° CCL 142), mouse origin;

4) Submandibular Gland Cell Line:
   SCA-9 Clone 15 (ATCC N° CRL 1734), mouse origin;

5) Intestine Cell Line:
   IA-XsSBR (ATCC N° CRL 1677), rat origin;

6) Osteogenic Cell Lines:
   FC25T (ATCC N° CRL 6090), cat origin;
   D-17 (ATCC N° CCL 183), dog origin;
   143B (ATCC N° CRL8303), human origin;
   HOS (ATCC N° CRL 1543), human origin;
   Saos-2 (ATCC N° HTB 85), human origin;
   SK-ES-1 (ATCC N° HTB 86), human origin;
   UMR-106 (ATCC N° CRL 1661), rat origin;
   UMR-108 (ATCC N° CRL 1663), rat origin;

For the purpose of one specific embodiment of the metabolic assay according to the present invention, namely the collagen analysis, the assay is performed as described below:

Confluent osteogenic cells, specifically the C1 cell line described above, are labeled for 24 h with 50 μCi/ml of 4.5 [$^3$H]proline (32 Ci/mmol; Commissariat à l'Energie Atomique, Saclay, France) in DME supplemented with 1% FBS, 100 μg/ml ascorbic acid, and 50 μg/ml b-aminopropionitrile fumarate (Sigma Chemical Co., Saint Louis, Mo., USA). The cells are collected in 50 mM Tris-HCl (pH 7.4) containing 150 mM NaCl, 25 mM EDTA, 10 mM N-ethylmaleimide, and 2 mM PMSF, and pooled with the culture medium. After sonication and addition of trichloroacetate (TCA) (10%), the insoluble residue is collected by centrifugation.

The amount of [$^3$H]proline incorporated into collagenase-digestible protein and non-collagenase protein is determined as described by Peterkofsky et al. in 1971.

Collagen types are determined by PAGE: pellets resuspended in 0.5 M acetic acid are digested with 100 μg/ml pepsin fumarate (Sigma Chemical Co., Saint Louis, Mo., USA), pH 2.0 for 4 h at 4° C. The pepsin digest brought to pH 8.0 is dialyzed and lyophilized. Samples are then analyzed by SDS-PAGE. Delayed reduction with 2-mercaptoethanol is used in some samples. Labeled proteins are visualized by fluorography or autoradiography and quantified by a beta radioimager device.

Other metabolic events are followed in determining the metabolic changes induced by the therapeutic molecules used according to the present invention, such as the mineral component deposits on the collagen matrix. For this purpose, the hereunder described assay is used:

Cell cultures: the clonal mesodermal cell line C1 is used. The C1 cells are plated at 3×10$^5$ cells in 100 mm-diameter untreated plastic dishes and are cultured in Dulbecco modified Eagle medium (DMEM, Gobco, Grand Island, N.Y., USA) with 10% fetal calf serum (FCS). After 8-10 days of culture, three-dimensional clusters are formed. At that time (day 0), the cells are cultured in DMEM with 1% FCS in presence of 10 mM beta-glycerophosphate (Sigma) and 50 μg/ml ascorbic acid (Sigma). In some wells, 50 μg/ml of tetracycline are added to the media in order to visualize by fluorescent labeling the mineral incorporated within the matrix. The medium is changed every 3 days and the cultures are conducted for up to 30 days.

Biochemical determinations. At 0, 2, 7, 11, 16, 22 and 30 days, the cultures are collected, rinsed three times in calcium-free PBS, and divided into three equal parts for evaluation of calcium, alkaline phosphatase activity and DNA synthesis. For determination of calcium, the cultures are dissolved in 1 ml 6N HCl for 1 h at 100° C. Calcium is assayed in aliquots by atomic absorption spectrometry after dilution in lanthanum chloride. For determination of alkaline phosphatase activity, 1 ml of cold distilled water is added to the cultures. After sonication for 10 sec, the insoluble material is removed by centrifugation. Some samples are heated at 56° C. for 1 h to measure the bone-type (heat labile) alkaline phosphatase activity. The activity of the enzyme is determined by measuring the amount of p-nitrophenol formed at 37° C. after 30 min. Cell protein content is measured by the method described by Lowry et al. in 1951.

The non-radioactive beta-glycerophosphate may be replaced by a radioactive molecule. The phosphorous compound conventionally used as bone localizing agent is an inorganic phosphate or pyrophosphate. A radioactive molecule that can be used in the above assay is tetrasodium $^{32}$P pyrophosphate (NEX 019, New England Nuclear) or $^{99}$technetium that binds to the phosphorous compound.

Thus, another object of the present invention comprises a method for screening ligand molecules that possess an agonist or an antagonist biological activity on the target receptor of the XQHNPR (SEQ ID NO: 14) pentapeptide, comprising the steps of:
  a) Culturing a eukaryotic cell capable of synthesizing collagen;
  b) Incubating the eukaryotic cell of step a) beta-glycerophosphate in the presence of the candidate molecule ($10^{-10}$-$10^{-5}$ M) and of a submaximal concentration of QHNPR (SEQ ID NO: 1) peptide;
  c) Quantifying the production of a specific metabolite, such as calcium, alkaline phosphatase or DNA synthesis, respectively in the presence or in the absence of the candidate ligand molecule and in the presence or in the absence of a submaximal concentration of QHNPR (SEQ ID NO: 1).

The eukaryotic cell of the above method may be either a cell that has been transfected or transformed with a nucleic acid coding for collagen, or a eukaryotic cell that is able to synthesize collagen in a constitutive or in an inducible manner. A preferred cell is a mammalian cell that is able to naturally synthesize collagen, such as the C1 cell line.

Other metabolic changes induced by the therapeutic molecules used according to the present invention may also be assessed, such as other enzyme assays, ion transport assays or signal transduction assays. Enzyme assays that may be performed comprise acetylcholinesterase (Ellman G. L. et al., 1961, Biochem. Pharmacol., 7:88), cathepsin (Barret A. J. et al., 1981, Methods Enzymol., 80:535), ATPase, cyclooxygenase (Mitchell J. A. et al., 1993, Proc. Natl. Acad. Sci., 90:11693), guanylate cyclase (Wolin M. S. et al., 1982, J. Biol. Chem., 257, 13312), lipoxygenase (Shimizu T. et al., Proc. Natl. Acad. Sci., 1984, 81:689), monoamine oxidase (Weyler W. et al., 1985, J. Biol. Chem., 260:13199), myeloperoxidase (Desser R. K. et al., 1972, Arch. Biochem. Biophys., 148:452), phosphodiesterase (Nicholson C. D. et al., 1989, Br. J. Pharmacol., 97:889), protein kinase (Hannun Y. A. et al., 1985, J. Biol. Chem., 260:10039), tyrosine hydroxylase (Nagatsu et al., 1964, Analyt. Biochem., 9:122) or xanthine oxidase (McCord J. K. et al., 1969, J. Biol. Chem., 244:6049) assays. Ion transport assays comprise Ca pump (Jean T. et al., 1986, J. Biol. Chem., 261:16414), Ca channel (Galizzi J. P. et al., 1987, J. Biol. Chem., 262:6947), Na channel (Jacques Y. et al., 1978, J. Biol. Chem., 253:7383), Na—K pump (Chassande O. et al., 1988, Eur. J. Biochem., 171:425), Na—Ca antiport (Barle A. B. et al., 1990, Am. J. Physiol., 259:19), Na—H antiport (Jean T. et al., 1986, Eur. J. Biochem., 160:211), Na/K/Cl cotransport (Chassande O. et al., 1988, Eur. J. Biochem., 171:425) assays. Signal transduction assays that may be also used comprise Ca release (Grynkievicz G. et al., 1985, J. Biol. Chem., 260:3440) or PI turnover (White T. E. et al., 1993, Br. J. Pharmacol., 108:196). The technical content of the above-referenced articles relative to the metabolic assays are herein incorporated by reference.

An object of the present invention is also a method for screening ligand molecules that possess an agonist or an antagonist biological activity on the target receptor of the XQHNPR (SEQ ID NO: 14) pentapeptide, comprising the steps of:
  a) Preparing a confluent target cell culture monolayer or preparing a target organ specimen or a tissue sample (cryosections or slices);
  b) Incubating the cell culture, organ specimen or tissue sample of step a) in the presence of the candidate molecule ($10^{-10}$-$10^{-5}$ M) and of a submaximal concentration of QHNPR (SEQ ID NO: 1) during a time sufficient for the metabolic change to take place;
  c) Quantifying the production of the corresponding metabolite, respectively in the presence or in the absence of the candidate ligand molecule and in the presence or in the absence of a submaximal concentration of QHNPR (SEQ ID NO: 1).

The metabolic change referred to in the above screening method is interchangeably a change in the production of any of the metabolites that are assayed according to the above-referenced methods. Consequently, the time that is sufficient for the metabolic change to take place will depend on the assayed metabolite and is indicated, for a particular metabolite, in each article reference that has been given hereinbefore.

Tissue slices, tissue cryosections or tissue homogenates are used in the performing of the binding or metabolic assays in order to select the ligand molecules of interest that represent the biologically active derivatives of the XQHNPR (SEQ ID NO: 14), specifically QHNPR (SEQ ID NO: 1), peptide according to the present invention. Preferred tissue samples are of kidney, pancreas, bone, dental, glandular mucosa of stomach, prostate and intestine origin as well as salivary glands.

Tissue homogenates are prepared by first immersing biopsies in liquid nitrogen. The frozen samples are then homogenized in 20 vol ice-cold 50 mM Tris/HEPES buffer, pH 7.5, containing 1 mM EGTA, 0.3% (wt/vol) bacitracin, 20 mM 4-amidinophenylmethanesulfonyl fluoride, and 10 mM leupeptin with a motor-driven Teflon-glass homogenizer. The homogenates are centrifuged at 24,000×g for 20 min at 4° C. and the pellets washed once with 50 mM Tris/HEPES, pH 7.5, containing 1 mM EGTA. The final pellets are suspended in 50 mM Tris/HEPES pH 7.5 containing 1 mM EGTA and 0.3% (wt/vol) bacitracin, and stored at −20° C. Further details of procedure are described by Stangi et al in 1993, depending on the origin of the tissue to homogenize, the procedures used by Stangi being herein incorporated by reference.

In order to obtain intact tissue samples, for example of kidney origin, the following procedure is used:

Before organ or tissue harvesting, for example in rat, the animal is anesthetized with chloral hydrate (35%, 0.14 ml/100 g body weight) or with pentobarbital (45 mg/kg body weight). Then, an intracardiac perfusion with 100 ml 4° C. isotonic sucrose is performed (Loring et al., 1993).

Kidneys may be obtained after human biopsies or from male Wistar rats immediately after death by cervical dislocation, or anesthesy as described above. Tissue samples are immediately embedded in Tissue-Tek (Miles, Elkhart, Ind.) and frozen to cork mounts in melting isopentane (at −70° C.) without prior fixation. Specimens are stored at −70° C. until use. 10-30-μm thick sections are cut in a cryostat (at a temperature range of −20° C. to −30° C.) and are thaw-mounted onto uncoated low-iron glass slides. They are then used immediately or vacuum-dried and stored at −20° C. with silica gel for up to 5 days until use. Such a technique was described by Walsh et al. in 1995, the details of which are herein incorporated by reference.

Alternatively, tissue sections are frozen in dry ice in the presence of isopentane and thaw-mounted onto microscope slides, and stored at −80° C. until use (Whitcomb et al., 1993).

As another alternative method for obtaining fresh tissue samples, specimens of human renal cortex and medulla are obtained from subjects undergoing nephrectomy. The portions of the kidney collected are placed in ice-cold 0.9% NaCl solution to remove blood and cell debris. Blocks including the renal cortex and medulla or separate samples of the cortex or of the medulla are embedded in a cryoprotectant medium (OCT, Ames, Iowa) and frozen in isopentane cooled with liquid nitrogen or dry ice. OCT blocks are stored at −80° C. until use. Serial 8-μm thick sections are obtained using a −20° C. microtome cryostat, mounted on gelatin-coated microscope slides and air-dried. Such a technique is described by Ricci et al. in 1993.

Preferred biologically active derivatives of the XQHNPR (SEQ ID NO: 14) peptide of the therapeutic composition according to the present invention have better pharmacokinetics than the endogenous natural or synthetic XQHNPR (SEQ ID NO: 14) peptide and thus possess a longer in vivo half-life as compared to their natural counterparts.

A method for assessing the pharmacokinetics of the ligand molecules selected according to the binding assay and the metabolic assay above described is exemplified in Example 3. Alternatively or in addition, plasma clearance of the selected ligand molecules is determined according to the technique described by Wu et al. in 1996 or the technique described by Ezan et al. in 1986, or by Ezan et al., 1996, which techniques are herein incorporated by reference.

The above-described biologically active derivatives, which could not have been identified before the discovery of the inventors, are also an object of the present invention.

Thus, the invention also concerns the biologically active derivatives of the XQHNPR (SEQ ID NO: 14) peptide that have been selected according to the screening processes hereinbefore described, provided that they have not the following structure: Y—HNP-Z, wherein Y denotes a glutamine (Q) or a pyroglutamic acid residue and Z represents an OH group or a basic amino acid, the basic amino acid being a Lysine (K) or an Arginine (R). Indeed, also excluded, as a member of the biologically active derivatives of the XQHNPR (SEQ ID NO: 14) peptide, is the 146 amino acid protein constituting the SMR1 peptide itself (PCT Patent Application N° WO 90/03981). However, the therapeutic use of these molecules that are themselves excluded by the present invention, is a main object of the instant invention.

The biologically active derivatives of the XQHNPR (SEQ ID NO: 14) peptide used in the therapeutic compositions according to the present invention have been, in a preferred embodiment, selected firstly according to their ability to bind to the same targets as the XQHNPR (SEQ ID NO: 14), specifically QHNPR (SEQ ID NO: 1), peptide and secondly by their capacity to induce metabolic changes (adenylate cyclase activity stimulation, collagen production, etc.) within the target or to abolish, block or prevent said metabolic changes of the target that are induced by the XQHNPR (SEQ ID NO: 14), specifically QHNPR (SEQ ID NO: 1), peptide.

The present invention also deals with the use of therapeutic compositions comprising an effective amount of the XQHNPR (SEQ ID NO: 14) peptide or of one of its biologically active derivatives.

As previously detailed, the use of the therapeutic compositions according to the invention is indicated in case of an hydro-mineral imbalance of the body. These use of the compositions is also indicated in the case where a defect in the normal endogenous level of the QHNPR (SEQ ID NO: 1) pentapeptide is diagnosed from a biological sample of the patient, particularly from patient fluids such as serum or plasma, saliva and urine. The level of pentapeptide concentration in the biological sample is considered defective when it is at least five-fold less important than the non pathological concentration usually found as well as when it is at least five-fold more important than the non pathological concentration usually found in this particular biological sample.

A diagnostic method that allows determination of the concentration of the QHNPR (SEQ ID NO: 1) pentapeptide in a biological sample, specifically from serum or plasma, is a competitive radioimmunoassay (RIA), as described by Rougeot et al. in 1994.

Briefly, the liquid phase RIA is performed in 0.2 M Tris/HCl pH 8.5, containing 0.25% bovine serum albumin (Fr 5, Miles), 0.1% Triton X-100 (Sigma), 1000 KIU (kallikrein international unit)/ml Trasylol (a trypsin and kallikrein inhibitor; Bayer), EDTA (1 mM) and 0.1 g/l $NaN_3$. Standard or sample (0.1 ml), 0.1 ml diluted anti-pentapeptide serum (Rougeot et al., 1994) and $^{125}$I-Labelled pentapeptide (15× $10^3$ dpm, 0.1 ml) are incubated overnight at 4° C. Bound and free fractions are separated by propanol precipitation (10 μl normal rabbit serum and 1 ml ice-cold 1-propanol) and the radioactivity of the precipitate is determined using a gamma counter. The plasma, saliva or urine samples would be collected into previously cooled tubes containing a mixture of peptidase inhibitors (1 mM EDTA, 1000 U/ml Aprotinin, 130 μM bestatin, 1 μM leupeptin, 0.4 mM pefabloc, 1 μM pepstatin).

The above diagnostic method is now used as a tool of medical use to determine the type of defect that can be associated with a mineral ion imbalance symptom. In its medical use, this diagnostic test is also an object of the present invention. The successive steps of this diagnostic test are the following:

a) Incubating a labeled XQHNPR (SEQ ID NO: 14), specifically QHNPR (SEQ ID NO: 1), peptide with a polyclonal or a monoclonal antibody directed against the same peptide;

b) Bringing into contact the immune complexes formed with a biological sample from a patient to be tested suspected to contain an endogenous non-labeled XQHNPR (SEQ ID NO: 14) peptide, specifically the QHNPR (SEQ ID NO: 1) peptide;

c) Detecting the monoclonal or polyclonal antibody-bound labeled peptides, that have not been displaced by the endogenous non-labelled XQHNPR (SEQ ID NO: 14), specifically QHNPR (SEQ ID NO: 1), peptide contained in the biological sample in order to determine the concentration of this endogenous peptide that is contained in the biological sample;

d) Comparing the concentration of the XQHNPR (SEQ ID NO: 14), specifically QHNPR (SEQ ID NO: 1), peptide found at step c) with the concentration of the XQHNPR (SEQ ID NO: 14), specifically the QHNPR (SEQ ID NO: 1), peptide normally found in a healthy individual.

e) Calculating the amount of a therapeutic composition that is necessary in order to supply the defect of the XQHNPR (SEQ ID NO: 14) peptide in the body fluids and tissues.

The amount of therapeutic molecule to be administered is calculated, taking into account the specific in vivo pharmacokinetics of said therapeutic molecule, the in vivo pharmacokinetics being assessed as described in Example 3 and, of course, the normal amount of XQHNPR (SEQ ID NO: 14), specifically QHNPR (SEQ ID NO: 1), peptide normally found in the body fluids (plasma, saliva, urine) or organs.

The labelled XQHNPR (SEQ ID NO: 14) peptide used in the diagnostic test is radioactively or non-radioactively labelled.

The polyclonal antibody used in this diagnostic method may be optionally under the form of an immune serum.

The particular quantitative immunodetection system designed by the inventors is both extremely specific and sensitive: 50% displacement of the $^{125}$I-Labelled pentapeptide QHNPR (SEQ ID NO: 1) is obtained with no more than 570 fmol pentapeptide standard ([Glp$^1$] pentapeptide or [Gln$^1$] pentapeptide. The detection limit (80% binding) is 106 fmol standard peptide. The inter-assay variation coefficient is 12%, n=24. The cross-reactivity of the antiserum with tetrapeptide sequence (QHNP) (SEQ ID NO: 11) and thyrotropin-releasing hormone (Glp-His-Pro) is less than 0.01%.

In one specific embodiment of the present invention, the XQHNPR (SEQ ID NO: 14) peptide concentrations quantified according to the above described diagnostic method are used to determine the amount of the XQHNPR (SEQ ID NO: 14) peptide or of one of its biologically active derivatives to be administered to the patient in order to supply for the diagnosed defect, in case of a low level in the endogenous peptide and to determine their pharmacokinetic parameters in pathologic and non-pathologic subjects.

The therapeutic compositions containing the SMR1 protein or SMR1 maturation products or their derivatives and used according to the present invention may be either under the form of a liquid solution, under the form of a gel or under the form of a dry powder.

The therapeutic peptides according to the present invention are advantageously complexed with metal salt ions such as Ca$^{++}$, Cu$^{++}$, Ni$^{++}$, Mg$^{++}$ or Al$^{++}$ either directly or indirectly with the carrier ions proteins or also calcium phosphate as described in the French Patents N° FR-2,543,439 and N° FR-2,181,426 (Reliveld et al.), or also with ATP.

The therapeutic peptides according to the present invention may also be complexed to Dextran or Dextran derivatives.

A specific embodiment of the use of controlled delivery systems containing dextran molecules is represented by "long Action (LA)" form and "Renewable Long Action (RLA)" form. The LA form consists of microspheres of polylactic acid that contain bromocriptin included in Dextran. In the RLA form, bromocriptin is contained in microspheres of D, L-polylactide-coglycolide-glucose, the degradation of which is almost complete in a period of time of less than three months and which allows repeating the administration numerous times for a long period of time (Montini et al., 1986; Kato et al., 1988).

Preferably, the therapeutic compositions according to the present invention are administered locally, near the site, organ or tissue, to be treated. As an alternative embodiment, the therapeutic compositions of the invention are administered by the oral route in order to act systemically or at the level of the buccal or stomach mucosa or at the level of the gastro-intestinal tract. Such therapeutic compositions may be in the form of a saline solution or a tablet, preferably a controlled release tablet. A typical controlled release tablet is described in the PCT Patent Application No. WO 9622768, which contains from about 30 to about 70 percent by weight of one or more cellulose ethers such as hydroxypropyl methylcellulose, and from about 30 to about 70 percent by weight of an inert substance such as corn starch.

In another embodiment of the therapeutic compositions of the present invention, the XQHNPR (SEQ ID NO: 14) peptide or its biologically active derivatives are included in a controlled release device to be placed locally in the body, in order to obtain a sustained delivery of the active molecules in the surrounding of the site to be treated.

Preferably, the controlled release devices that are used for the purpose of the present invention are lipid or polymer microparticles that dissolve or are hydrolyzed slowly within the body, specifically in the stomach or in the gastro-intestinal tract.

In a preferred embodiment of the controlled release devices of the present invention, the latter can be implanted locally in order to ensure a limited area diffusion of the active molecule, surrounding the organ or tissue to be treated.

Preferred sustained delivery devices according to the present invention contain biodegradable polymers such as described in the PCT Patent Application No. WO 9701331. The polymer may be a polysaccharide as in the PCT Patent Application No. WO 9613253, such as sodium alginate. A biodegradable sustained preparation is preferably composed of a polysaccharide which is coated with cationic molecules such as chitosan, the carrier being slowly enzymatically hydrolyzed, for example by lysozyme, in vivo after the release of the active molecule.

The polymer used in the controlled release devices according to the present invention may also be a polyvinylpyrrolidone type polymer, such as described in the PCT Patent Application No. WO 8804922, or a starch hydrolysate, such as described in the PCT Patent Application No. WO 9417676.

In a specific embodiment, the polymer is a bioadhesive polymer such as carboxymethylcellulose, Carbopol™, Polycarbophil™ or sodium alginate, which binds with an excellent efficiency to the mucin present at the surface of the epithelium (Robinson et al., 1998), these polymers being used especially in the case of an oral drug delivery.

Other preferred sustained delivery devices according to the present invention are under the form of polymer microbeads, for example porous crosslinked polymeric microbeads, such as described in the PCT Patent Application No. WO 9533553.

Another embodiment of the controlled release devices according to the present invention are liposomes either in a hydrated form, such as in the PCT Patent Application No. WO 8601102 or in the PCT Patent Application No. WO 9522961 (Capron et al.), or in a dehydrated form, such as in the PCT Patent Application No. WO 8601103. Other lipid emulsions used as drug delivery systems that may be used for the purpose of the present invention are described by Davis et al. in 1988, that may be administered via the oral, parenteral or the intravenous route. The liposomes may contain saccharide determinants that bind to specific cell membrane components in order to facilitate the delivery of the active molecule towards a selected target cell, in particular saccharide determinants that bind to specific lectins of the cell membrane (Shen, 1988).

Another embodiment of the sustained delivery formulations used according to the present invention consists of a particle vector comprising, from the inner layer to the outer layer:
  a non liquid hydrophilic core, for example a crosslinked polysaccharide or oligosaccharide matrix, said core being optionally grafted with ionic ligands carrying at least one group selected from phosphate, sulfate, carboxylic acid, quaternary ammonium, secondary amine or tertiary amine.
  an external layer consisting of lipid compounds that are grafted onto the core by covalent bounds.

Such a particulate vector is described in the PCT Patent Application No. WO 94/23701 (Perrin et al.)

Exceptionally, the peptide XQHNPR (SEQ ID NO: 14) of the invention may be administered to the skin via a transdermal iontophoretic delivery system, such as described by Chien et al. in 1988.

The therapeutic compositions used according to the present invention contain a pharmaceutically effective amount of the XQHNPR (SEQ ID NO: 14) peptide or of one of its biologically active derivatives.

The amount of active principle contained in one therapeutic dosage of the XQHNPR (SEQ ID NO: 14) peptide or biologically active peptide derivative is contained in the range between 10 µg/kg and 10 mg/kg of body weight, preferably between 50 µg/kg and 5 mg/kg of body weight and more preferably between 200 µg/kg and 1 mg/kg of body weight.

One object of the present invention is also a therapeutic composition comprising a pharmaceutically active amount of the SMR1 protein, its maturation products, specifically the XQHNPR (SEQ ID NO: 14) peptide, more specifically the QHNPR (SEQ ID NO: 1) pentapeptide, as well as the biologically active derivatives of the latter, used in combination with a pharmaceutically effective amount of another molecule involved in the regulation of the mineral ion balance. The preferred molecules to be associated with the SMR1 protein or derivatives are the parathyroid hormone (PTH), calcitonin (CT) and 1,25-dihydroxyvitamin D.

The fact that the inventors have determined, in the male rat, the precise topographical distribution of target organs for XQHNPR (SEQ ID NO: 14) peptides, has allowed the present inventors to understand and specify the role of these peptides in local and peripheral systems.

More specifically, the inventors have mapped the peripheral targets for the final secretory maturation product of SMR1, the pentapeptide, by examining in vivo the gross tissue distribution of the radiolabeled peptide with whole body autoradiography (WBA) (Ullberg et al., 1981). This method provides a visual image of the entire animal, therefore rendering it possible to examine simultaneously the uptake of the pentapeptide in a large number of tissues and compartments. Furthermore, this approach is considerably more attractive than an in vitro method, since labeling in living tissue minimizes the possibility of misinterpretation due to non-specific distribution, to receptor site degradation and to nonreceptor site-bound peptide eliminated through the bloodstream (Lindberg et al., 1991). For these reasons, the time-related tissue uptake for the pentapeptide has been assessed in vivo. In order to eliminate the possibility of competition for the available binding sites from endogenous peptide, labeling has been achieved by intravenously infusing tritiated pentapeptide in five weeks old pubescent rats. In addition to film autoradiography, the mapping and the time course of the tritiated peptide uptake by the living organs has been recorded by the recently developed β-radio imager, which offers the unique capability of detecting and quantifying the β particles emitted from tritiated ligand bound to flat surfaces such as whole body sections (Charpak et al., 1989; Tribollet et al., 1991). The inventors have also analyzed the chromatographic characteristics of the labeled compound associated with the target organ.

Biological receptor sites have two essential characteristics that allow specific binding to be identified, in vivo; they have a high affinity for the ligand and the binding is saturable (Whitcomb et al., 1993). Therefore, displacement experiments, using parallel systemic administration of an excess of the corresponding unlabeled peptide has been performed. Furthermore, the specific cellular localization of labeled pentapeptide to target tissues has been identified by section microscopic autoradiography.

Finally, to appreciate the relevance of the pentapeptide uptake under physiological conditions the inventors have determined the endogenous bloodstream secretion pattern of the peptides related to SMR1 in conscious adult male rats. It is important to stress that all the pharmacokinetic and cellular-site distribution studies were realized using physiological concentrations of labeled pentapeptide.

The present invention will be illustrated in details in the following Examples without being in any way limited in scope to these specific embodiments.

MATERIALS AND METHODS

A. Chemicals

The peptides corresponding to the sequences $(Glp_1)$-His-Asn-Pro-Arg (SEQ ID NO: 9), $(Gln_1)$-His-Asn-Pro-Arg (SEQ ID NO: 1) and $(Gln_1)$-His-Asn-(D3,4-Pro)-Arg (SEQ ID NO: 10) were synthetized by the Laboratoire de Chimie Organique, Institut Pasteur, Paris, France.

Labeled compound: $(Glp_1/Gln_1)$-His-Asn-$(3,4^3H)$Pro-Arg was synthesized by Dr. R. Genet, Departement d'ingénierie et d'étude des protéines, CEA/Saclay, Gif/Yvette, France. The RP-C18 HPLC purified product ($\geq$98% purity) with a specific radioactivity estimated as 2.22 TBq/mmole was stored at −80° C. in 10% methanol/0.1% trifluoroacetic acid (1.11 GBq/ml). The purity of the tritiated pentapeptide was systematically assessed before use, by reverse-phase C18 and cation-exchange FPLC chromatographies according to the methods previously described (Rougeot et al., 1994).

B. Animals

Wistar male rats (4 weeks old), purchased from Iffa-Credo (France), were kept at 2-4 animals/cage under controlled lighting and temperature with free access to food and water, until use 5-7 days later for the study of pentapeptide receptor-site distribution and 5-6 weeks later for the study of endogenous pentapeptide secretion. They were gently handled daily by the operator throughout this period. All experiments were performed between 10.00 and 14.00 h.

C. Administration of Labeled Compound

Labeled compound i.e. 6.66 MBq, 3 nmoles or 2 mg for whole body autoradiography (WBA) and 370-555 KBq, 170-250 pmoles or 110-160 ng for the pharmacokinetic and cellular-site distribution studies was diluted in 100-200 ml of phosphate-buffered saline (PBS Dulbecco's, Bio Media, France) and administered intravenously into the jugular vein of anesthetized rats (halothan for WBA or pentobarbital for all the other experiments).

D. Whole-Body Macro Autoradiographic Visualization

The target tissues for the final secretory maturation product of SMR1, the pentapeptide, was examined, in vivo, by the whole body autoradiography procedure according to the method of Ullberg (Ullberg et al., 1981).

The five week-old rats were sacrificed under halothane, at 90 sec., 3, 60 and 240 min. after i.v. injection of 3 nmoles (6.66 MBq or 2 µg) of tritiated pentapeptide. At the selected time, the restrained animal was immediately immersed in a −80° C. mixture of dry ice and isopentane, to prevent artifactual tracer redistribution. After 48 hours in self-sealing plastic stored at −30° C., the animal was then blocked in mounting medium. Whole body sagittal sections (20 mm) of the frozen rat were made at −30° C. with a cryostat (whole body slicing microtome Leitz 400 with a chest mobile freezer Leitz O M, Leica, France). Sections adhering to Scotch tape were left in a freezer, temperature −30° C., for 4 days to insure complete drying. The tapes were placed in a film cassette with $^3$H Hyperfilm (Amersham, France) at −20° C. After two weeks the films were developed in Kodak D19 developer and fixed in Kodak fixer.

E. Tissue Preparation for Sectioning and Light Micro-Autoradiographic Visualization The cellular-site localization for physiological concentrations of labeled pentapeptide was investigated by paraffin- or resin-section microscopic autoradiography procedure. Sixty minutes after $^3$H-pentapeptide (555 KBq, 160 ng or 250 pmoles) i.v. administration, the anesthetized male rats were perfused via the jugular veins with ice-cold Krebs Ringer Bicarbonate Glucosed buffer and then 0.5% paraformaldehyde/0.5% glutaraldehyde fixative PBS buffer (plus glucose 1.6%, $CaCl_2$ 0.002% and DMSO 1%) (50 ml/5 min. for each). Tissues were rapidly removed and harvested for paraffin sectioning (Paraplast plus-Sherwood medical, OSI, France) or for resin sectioning (histo-resin Leica, France). All sections were cut at 5 microns (Reichert Jung for paraffin and RM2155 Leica for resin sections) and mounted on Superfrost/Plus glass slides (non gelatin-coated). Paraffin was removed with xylene, and sections were carried through a descending, then an ascending ethanol series (from 100 to 50%, V/V and reverse). Dried sections were then processed for light microscope autoradiography by attaching nuclear emulsion-coated (Kodak, NTB2, diluted 1:1 with distilled water) coverslips to them. After air drying for 2 hrs at room temperature the autoradiographs were exposed for 6 to 10 weeks in light-tight boxes at 4° C. Radiosensitive coverslips were developed in Kodak D19 (3 min.) developer and fixed in Kodak fixer (3 min.) Sections were counterstained with Harris' hematoxylin (Prolabo, France) and Toluidine blue (Sigma, France), dehydrated and mounted in Eukitt medium. The tissue and overlying silver grains were viewed and photographed with a Leica photomicroscope equipped with bright-field optics (DMRD Leitz, Leica).

F. Mapping and Quantification of 3H-pentapeptide Uptake by Living Tissues

The quantitative determination of the radioactivity in various organ sections was carried out by using a gaseous detector of β-particles, which has recently been developed (Charpak et al., 1989; Tribollet et al., 1991). Data from whole body sections or individual organ sections placed in the gas-chamber detector were collected for 8 hr. or 50 hr., respectively. The number of counts per pixel was recorded in the β imager 2200 (Biospace, France) with a surface detector of 20×20 $cm^2$, followed by computer-assisted image analysis with the β Vision program using a HP Vectra computer. The tritium activity was determined as counts/$mm^2$. The linearity of this method of detection allowed measurement of the non specific binding of $^3$H-pentapeptide, measured in various structures or compartments within the section with apparent non binding sites for the peptide (background tissues, e.g. muscle and cardiac blood except brain and spinal cord) or in the same labeled structure, in displacement experiments.

In the case of radioactive quantification of organ sections or acid extracts, using a liquid scintillation counter (MR300Kontron), the tritium activity was determined as cpm/mg protein. Protein concentration was determined by the Bradford method (Bradford et al., 1976).

G. Chromatographic Characterization of Radioactive Peptide Uptake by Tissues The chromatographic characteristics of the labeled compound associated, in vivo, to target organs were assessed by HPLC.

At selected time points (2 and 180 min.) after administration of tritiated pentapeptide, the anesthetized rats were sacrificed (cardiac blood puncture) and tissues quickly removed on ice. The tissues were immediately homogenized at 4° C. in 5-10 volumes of 0.1 M chlorhydric acid using a potter homogenizer (demineralization of bone tissue was realized after 24-48 h at 4° C. in guanidium hydrochloride and EDTA pretreatment, 4 M and 0.25 M final concentration, respectively). Homogenates were centrifuged for 30 min. at 4° C. and 15,000 g. To determine total radioactivity, aliquots of the supernatant solution were added to 50 volumes of Biofluor (NEN, Dupont de Nemours, France) and counted in a liquid scintillation counter.

To determine the radioactivity in the pentapeptide fraction, aliquots of the tissue extracts were submitted to a methanol-extraction procedure (Rougeot et al., 1994) after neutralization with Tris/HCl pH 8.5 containing 16 mM DTPA (DiethyleneTriaminePenta-Acetic acid, Sigma, France). The methanol phase was removed from the supernatant by partial evaporation, then lyophilization and the reconstituted aqueous phase containing 16 mM DTPA was applied to ODS AQ column (HPLC RP C18 chromatography) (AIT, France). Elution with a linear gradient of 0.1% trifluoro acetic (TFA) in water/0.1% TFA in acetonitrile (Merck, France) from 100/0 (vol/vol) to 50/50 (vol/vol) was performed for 30 min. at a flow rate of 1 ml/min. Fractions were collected every 60 sec. and analyzed for radioactivity using a liquid scintillation counter.

H. Pentapeptide Bloodstream Secretion and Pharmacokinetic, In Vivo a) Pentapeptide Systemic Secretion Under Basal or Ether-stress- and Adrenergic Agent-Induced Submandibular Gland Secretion of Conscious Male Rats The in vivo endogenous bloodstream secretion of peptides related to the SMR1 precursor, in particular the pentapeptide, was investigated in conscious adult male rats.

Rats of 9-10 week-old were placed in a jar for 2 min exposure to ether fumes, or were placed for 20-40 min. in individual metabolic cages after intra-peritoneal administration of adrenergic secretagogue agents (phenylephrine, 4 mg/kg plus isoprotereronol, 1 mg/kg) or vehicle (PBS Dulbecco's). At selected times, the rats were anesthetized with pentobarbital (45 mg/kg). Blood samples were taken by cardiac puncture and collected into previously cooled tubes containing a mixture of peptidase inhibitors (EDTA 1 mM, Aprotinin 1000 U/ml, bestatin 130 μM, leupeptin 1 μM, pefabloc 0.4 mM, pepstatin 1 μM). They were immediately centrifuged for 15 min. at 4000 g and 4° C. Plasma fractions were then submitted to a Porapak Q column extraction procedure (Rougeot et al., 1988) and tested for the pentapeptide content before and after HPLC separations.

Briefly, acidified plasma samples (HCl 0.1 N final concentration), were applied to Porapak Q beads (Waters, France), packed in 0.5×2 cm column. After, washing with TFA 0.1% in water, the peptides were eluted with TFA 0.1% in 50% methanol (recovery of the marker pentapeptide added was 93±6%, n=5). Each of the extracted samples was then analyzed by using a HPLC system (spectraphysic SP8000) connected to a HEMA-IEC BIO-1000 carboxymethyl column (Alltech, France). Cation-exchange chromatography was performed with a one step 30 min. linear gradient of 1-1000 mM ammonium acetate pH 4.6 at a 1 ml/min. flow rate. Fractions of 1 ml were collected and tested after lyophilisation for their pentapeptide content. The RIA procedure and characteristics for pentapeptide measurements have been described previously (Rougeot et al., 1994).

b). Pentapeptide Metabolic and Pharmacokinetic Studies

The in vivo time course of distribution, metabolism and elimination of the pentapeptide was investigated in anesthetized adult male rats using physiological concentrations of circulating tritiated pentapeptide.

Anesthetized male rats were given a bolus intravenous injection of 170 pmoles or 110 ng tritiated pentapeptide diluted in 100 µl PBS Dulbecco's. Blood was collected in tubes containing a mixture of peptidase inhibitors described above, via a silastic catheter implanted into the external jugular vein. Blood was withdrawn just before and 2, 4, 6, 8, 10, 20, 30, 45, 60, 90 and 120 min. after peptide administration. Two milliliters of blood per rat were taken in all and the entire urinary bladder content was collected at a last selected point.

The biological samples were submitted to centrifugation and Parapak Q extraction conditions, as described above. Chromatography using HPLC procedure described above and in the reference (Rougeot et al., 1994) was then applied to each extracted sample. The ODS AQ RP-C18 was used for identification of amino-terminal metabolites and Pep RPC HR C18 (Pharmacia, France) for identification of carboxyl-terminal metabolites. The radioactivity content of samples before and after chromatographic separations was determined using a beta counter (Kontron, MR300).

EXAMPLES

Example 1

Distribution of Target Organs for 3H-Labeled SMR1-Derived pentapeptide, hexapeptide or undecapeptide in Male Rats Examined by Whole-Body Autoradiography (WBA)

WBA has considerable application in studies of receptor binding and the analysis of the biological fate of proteins and peptides. We applied this approach to the examination of the potential target tissues of the SMG derived SMR1-pentapeptide. The mapping and time course of tissue distribution of radioactive pentapeptide was investigated at 90 sec., 3 min., 60 min., and 240 min. after 3 nmoles or 2 µg of $^3$H-pentapeptide were systemically injected into 5 week-old male rats. In order to generate autoradiographic images of sufficient density in a reasonable exposure time, and to appreciate the specific uptake compared to nonspecific labeling, a quantity of 6.66 MBq isotope was employed in these experiments. Although, we have used tritiated peptide of high specific activity (2.22 TBq/mmole), the dose of peptide infused into the circulation resulted in amounts of blood pentapeptide about 10 fold its physiological level (see following chapter). Furthermore, in order to eliminate the possibility of peptide binding sites previously occupied by endogenous peptide, pubescent male rats of five weeks old were used, since we have previously shown that the peptides derived from SMR1 were detectable in the male rat SMG only from six week-postnatal age (Rougeot et al., 1994).

Figures 1, 8B:
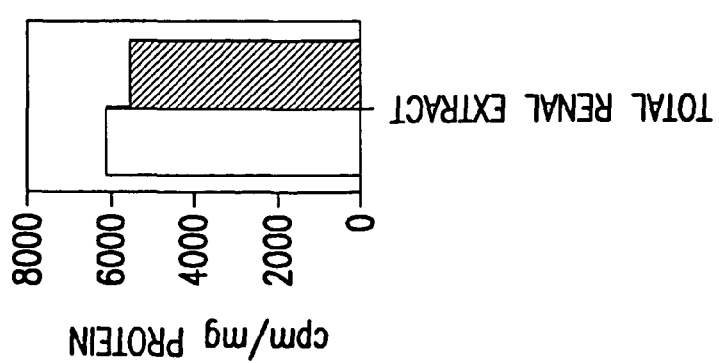

The gross anatomical distribution of $^3$H-pentapeptide uptake at 60 min. post dose, on whole rat body sagittal sections is shown in FIGS. 1 and 2. As illustrated in representative autoradiograms (FIGS. 1-A, 1-B), sixty minutes after a bolus intravenous injection of radioactive pentapeptide, a dense and distinct accumulation of the silver grains was apparent in the kidney and all bone tissue as well as dental tissue, glandular mucosa of stomach, pancreatic lobules and submandibular gland. At this selected time, moderate levels of labeling were seen in the liver, spleen, thymus and intestine wall. Neither the brain, nor spinal cord accumulated radioactive pentapeptide, demonstrating that a stringent blood-brain barrier limited the peptide uptake in vivo.

Assessment of tissue peptide targeting was accomplished by a β-radio imager quantification (FIG. 2). The number of β-particles emitted per unit area was collected directly from whole body sections, for 8 h. The linearity and selectivity of this method of detection allowed a relevant measurement of labeled structures compared to blackening defined with a selected anatomical area of the same section (here, blood in the cardiac space) (Tribollet et al., 1991).

In the kidney, pancreas, bone, incisor, submandibular gland and glandular gastric mucosa, the concentration of radioactivity at 60 min. post dose, count/mm$^2$ per 8 hr, was markedly higher, 4 to 10 times, than that of the blood in the heart. Much more radioactivity was present in these tissue spaces than is predicted by the same blood anatomical space (FIG. 3). This overestimation of the anatomical plasma and interstitial spaces may reflect the presence of peptide-receptor site binding within these tissues (Whitcomb et al., 1993). In the liver, thymus, intestinal wall and spleen the relative tissue accumulation was equal or less than 2 fold the blackening. And, in all the other tissues visualized (muscle, gonad, cartilage, non glandular gastric mucosa, brain) the level of radioactivity was equal, or less than that in blood area, reflecting restriction of the peptide solely to the anatomical plasma and interstitial spaces of these organs (FIG. 3).

The results of $^3$H-hexapeptide (FIG. 4) and of $^3$H-undecapeptide uptake (FIG. 5) clearly indicate that the target organs for these other maturation products of the SMR1 protein are almost the same as the target organs of the pentapeptide. Specifically, kidney and pancreas are the preferred target organs although the hexapeptide is also very efficiently retained by the glandular mucosa of stomach.

The dynamic profile of the $^3$H-pentapeptide uptake revealed that the radioactivity is rapidly distributed and differentially accumulated as early as 90 sec. and 3 min., in the kidney, pancreas, dental tissue and gastric glandular wall, with a tissue to blood ratio of close to 2. Label persisted within these tissues for longer than 240 min. More precisely, within the kidney, labeling was predominantly in the outer medullary area, over the time course studied from 90 sec. to 240 min. post injection (FIG. 1-A, 60 min. post injection). Within the bone, labeling was predominantly visualized as early as 90 sec. and 3 min, on the periosteal bone surfaces (periosteum). Within the tooth, labeling was also rapidly and long-lasting accumulated in the inner bulk of the incisor root as well as the alveolar bone. By contrast, in the blood and blood rich organs such as the lung and muscles, radioactivity was widely distributed at 90 sec and 3 min., but from where it was completely excluded at 60 min. No radioactivity was found in the intestinal content as late as 240 min post injection, whereas the bladder had radioactivity, indicating that some of the pentapeptide and/or metabolites had already been excreted into urine. This is consistent with the high labeling found in the renal pelvis and no labeling in the liver 90 sec. and 3 min post systemic injection. This result may be explained by a more efficient elimination of bloodstream pentapeptide through glomerular filtration than hepatic clearance and biliary excretion.

To determine whether the radioactive species detected is actually the compound administered, acid homogenates from target organs were analyzed after methanol extraction and reverse phase chromatography, 2-20 min. and 180-200 min. after systemic injection of 2 µg or 3 nmoles $^3$H-pentapeptide. A good correlation was obtained between the β-radio imager and liquid scintillation counting values for each organ, count/mm2 and cpm/g tissue weight, respectively. After 5-20 min. survival times, almost all the radioactivity uptake by tissues was extracted from the acid homogenates by the organic solvent used: 72±4%. While 180 min. after injection of $^3$H-pentapeptide, radioactive peptide fraction was picked up only when the methanol extraction was performed from tissue homogenates to which DTPA (16 mM), a strong metal chelating agent, was added: 53±9%. Moreover, only under this extraction condition did RP-HPLC chromatography reveal that the radioactivity was predominantly recovered in the peak corresponding to free pentapeptide: 52±8%. The rest of the radioactive extract represented metabolites, or undissociated peptide complex: 8±6% and 29±14%.

Taken together, these data provide strong evidence of selective, rapid and stable uptake of the pentapeptide by the outer medulla of the kidney, by the pancreatic lobules, by the glandular mucosa of stomach and by both bone and dental tissues.

Example 2

SMR1-Derived Pentapeptide Bloodstream Secretion Pattern in the Adult Male Rat

In order to appreciate the relevance of the pentapeptide uptake under physiological conditions, the endogenous bloodstream concentration of peptides related to the SMR1 precursor protein, in particular of the pentapeptide, was investigated in conscious adult male rats in response to pharmacological and acute stress stimuli. Blood sampling and extraction described in "methods" was carried out in the presence of a mixture of peptidase inhibitors plus EDTA and under these conditions, the basal plasma pentapeptide-immunoreactive level of 10 week-old male rats was: 1.9±0.2 ng/ml, n=5. In anesthetized rats, the time course response to adrenergic secretagogue agents of SMR1-derived peptide blood secretion had previously revealed that the peptides showed maximal circulating levels within 10-30 min following peritoneal administration of epinephrine (Rougeot et al., 1994). In conscious male rats, 20-40 min. post-injection of phenylephrine and isoproterenol, the plasma peptide-immunoreactive response was found to be 12.5±5.4 ng/ml, n=4.

The exposure of rats to saturated ether vapor for 2 min. is widely used to provoke stress, and its effect on endogenous adrenaline and adrenocorticotropin secretion, two of the major mediators of stress response, is well known (Rougeot et al., 1991; Van Herck et al., 1991). The endogenous adrenergic secretory response to acute ether stress in conscious rats resulted in an immunoreactive pentapeptide circulating level of 7.0±4.1 ng/ml, n=4. Extraction and fractionation by cation-exchange HPLC of plasma samples obtained under pharmacological or acute stress-induced conditions showed that 56±21%, n=6 of the immunoreactive peptide fraction corresponds to free pentapeptide; the rest corresponds primarily to the SMR1-derived hexapeptide and undecapeptide. The immuno-quantification of the pentapeptide plasma fraction could be assessed only if sampling and successive steps of extraction were carried out in the presence of EDTA or DTPA. The physiological range of circulating pentapeptide, in conscious adult male rats, was therefore established to 1-7 ng/ml.

Example 3

Time Course of Plasma SMR1-Derived Pentapeptide Distribution and Elimination

The in vivo fate of infused pentapeptide in the circulation was investigated. Plasma pentapeptide and its metabolites were measured with time after a single injection of a physiological quantity of 110 ng tritiated pentapeptide into the circulation of two male rats. Determination of plasma radioactive peptide fraction was performed by RP Porapak Q purification, and that of radioactive pentapeptide to metabolites by RP-HPLC chromatography. After reaching a maximal level within 2 min., the plasma pentapeptide concentration decreased rapidly, returning close to a basal level from 30 min. (FIG. 6).

HPLC fractionations of plasma peptide extracts revealed that in the bloodstream 35% of the infused pentapeptides were metabolized within 4 min., and that proteolysis occurred from the amino-terminal part of the peptide. Otherwise, plasma acidic pH treatment before porapak Q extraction partially dissociated a pentapeptide-binding substance complex, representing approximately 45% of the circulating peptide fraction.

Elimination was investigated by measuring radioactivity excreted over the time course of the experiment and was estimated in anesthetized rats, at 6 pmoles, eliminated through glomerular filtration, over a 60 min. period. Approximately 80% of the urine radioactivity appeared to be pentapeptide metabolites.

These results suggest that distribution of circulating pentapeptide to the tissues was almost complete 30 min. after injection. After this period, in order to allow for the total distribution of the peptide we examined its cellular uptake, at 60 min. post-injection with physiological concentrations of $^3$H-peptide.

Example 4

Cellular Localization of $^3$H-pentapeptide Binding Sites by Light Microscopic Autoradiography: In Vivo Radiolabeling 60 Min Post-Injection of Physiological Circulating Concentrations of $^3$H-Peptide The understanding of the function of SMR1-related peptide requires information about the identity of the cellular location of its binding sites within the target tissues identified above. Such a level of resolution can only be achieved by directly coating the in vivo radiolabeled organ sections with radiosensitive liquid nuclear emulsion, provided that the bound radioactive peptide is securely cross-linked to the binding sites with divalent aldehydes. Moreover, as the uptake of drugs or hormones can be influenced by dose, the significance of the selective cellular uptake of the pentapeptide was determined using physiological circulating concentrations of the tritiated molecule. The distribution volume for the pentapeptide in the male rat was calculated to be 35-40 ml/100 g. body weight, which is similar to the extracellular fluid volume. To achieve a final pentapeptide plasma concentration of 1-7 ng/ml, a five week-old, 100 g-male rat would require a systemic injection of 40-280 ng of labeled peptide.

Therefore, five week-old rats received between 110-160 ng $^3$H-pentapeptide, to reproduce physiological peptide plasma concentrations of ten week-old male rats for the following experiments: 1—cellular localization of peptide binding sites, and 2—regional and cellular saturation of peptide binding sites after coinjection of excess unlabeled peptide.

Light microscope autoradiographs of the kidney revealed the presence of silver grains confined preferentially within the deep inner cortex and the outer stripe of the outer medulla, over the epithelial cells of the S3 segment of the straight portion of the proximal tubules. Dense silver grains were also seen within the S1 and S2 segments of the initial convoluted portion of these tubules (FIG. 7-A). No specific cellular label was noticeable within the glomeruli, or within the epithelia of distal and collecting tubules.

Within the glandular gastric mucosa, 60 min. after $^3$H-pentapeptide injection, silver grains were exclusively distributed to the basal half of the gastric glands, over the chief or peptic cells (FIG. 7-B). Within the pancreatic tissue, silver grains were selectively and homogeneously concentrated over the cells of acini (FIG. 7-C). No label was observed within the various ducts and islets of Langerhans. Contrary to expectation, within the submandibular target tissue, no selective cell association of label was identifiable.

FIGS. 7-E and 7-F illustrate a section of part of the thoracic vertebrae and the proximal end of tibia respectively, both showing the trabecular bone. Within the bone tissue, the highest accumulation of silver grains occurred exclusively in the internal surface of the bone, in the spaces within marrow tissue, the trabeculae bone spaces. The intratrabecular spaces entrap bone cells, primarily the osteocytes and their long cytoplasmic processes occupy the lacunae and canaliculi, respectively. Within these spicules of bone, the silver grains were denser over the canalicular layer than over the lacunar layer. Specific accumulation of silver grains was not noticeable either in the cartilagenous growth plate or in the hematopoietic marrow (FIGS. 7-E, 7-F). FIG. 7-D illustrates a section into root of the rat upper incisor. In this dental tissue, silver grains were selectively concentrated over the entire dentin layer, along the length of the dentinal tubules of the canalicular system.

In displacement experiments, the cellular and total tissue distribution of 3H-pentapeptide were examined, after 60 min. post-coinjection of 100-fold excess of unlabeled peptide. The large excess of cold-ligand concentration resulted in the almost complete displacement of $^3$H-pentapeptide uptake within the renal outer medullary and diffusion of label toward the inner medullary collecting ducts (FIG. 8-A). Excess unlabeled peptide reduced binding to various extents within the glandular mucosa of the stomach, pancreatic and submandibular lobules and long bone, with a specific labeling percentage of 38-61%, 37-55%, 51-91% and 29-38%, respectively. The weak detectable reduction of radiolabeled peptide could be accounted for by the low abundance of receptor sites, or the presence of significant radioactive degradation products distributed between the plasma and interstitial space, and may obscure saturable binding, in vivo (Whitcomb et al., 1985). In our experiment, it appears that the effectiveness in detection of saturable binding in vivo depends on the distribution of the peptide binding sites within the specific organs, either wide distribution (pancreatic and submandibular lobules), or narrow distribution (bones, stomach, kidney) and on the selectivity of the analysis methods used, i.e. total tissue count or regional difference analysis, respectively (FIG. 8-B, kidney, specific labeling percentage from 12 to 92%).

In the present study, using an in vivo labeling method coupled to quantitative β-radio imager analysis of whole rat body sections, the inventors demonstrate that circulating SMR1-derived pentapeptide gains access to selective regions within the kidney, pancreas, submandibular gland, bone, tooth and stomach. The tissue uptake profiles have essential characteristics that allow specific binding sites to be identified in vivo, the binding is rapid (90 sec after administration, at the latest), stable (240 min), selective and saturable. It has also been demonstrated that this hormone-like peptide can bind to these tissue receptor sites at adult male rat physiological circulating concentrations.

As supported by the analysis of quantitative β-radio imager and kinetics of the distribution and elimination of pentapeptide in the rat bloodstream, at 90 sec. and 3 min. (circulating peptide distribution phase), the amount of pentapeptide in a distinct tissue reflects the sum of the amounts in the plasma and interstitial space plus bound receptor sites. At 60 min. (circulating peptide elimination phase) and later, the amount reflects the peptide binding sites-mediated sequestration. Therefore, the measure of selectivity and saturability of tissue and cellular uptake, realized 60 min. after peptide administration, actually reflects specific binding sites for the pentapeptide. A rapid and stable distribution and accumulation of the peptide was demonstrated within the outer medulla of kidney, pancreatic lobules, glandular mucosa of the stomach and periosteal and alveolar bone tissues as well as the incisor dentinal structure. The lack of early pentapeptide uptake by the inner bone matrix could be related to a substantially slower rate of exchange between the blood and the bone extracellular fluid as compared to the exchange between the blood and the nonbone extracellular fluids (Billinghurst et al., 1982).

The inventors extended this study by identifying the cellular localization to which the pentapeptide binds in each tissue in vivo. This approach provides the site of action, an essential step in the determination of the role of the SMR1-derived peptide in male rats.

The present results provide direct evidence that pentapeptide binding sites are localized within specific portions of the male rat nephron, with a density of distribution in the area of the deep inner cortex and the outer stripe of the outer medulla and in particular over the epithelial cells of S3, S2 and S1 segments of the proximal tubules. Therefore, from a histological point of view, the findings give evidence for a role of the circulating pentapeptide in the regulation of renal function in adult male rats. The proximal convoluted tubule plays a major role in the reabsorption of $Na^+$, $HCO3^-$, $Cl^-$, $Ca^{2+}$, $PO4^-$, water and organic solutes such as glucose and amino acids. The activity of most, if not all, renal epithelial transporting systems, is hormonally regulated by steroids (gonadal and glucocortico-adrenal steroids) and peptide hormones (pancreatic, pituitary and parathyroid hormones). Most of the hormones that modulate tubule reabsorption and secretion processes act on membrane receptors and can gain access to the cells from the blood flow (Tisher et al., 1996).

The visualization of pentapeptide binding sites within the internal area of bone, the trabeculae bone tissue and within the periosteal bone surface, the periosteum, provides in situ evidence for a role for the pentapeptide in the regulation of bone remodeling activities. Although the bone remodeling is a poorly understood process, numerous data indicate that this activity is ensured by various hormones, including steroids (androgens, oestrogens and glucocorticoids) and peptide hormones (parathyroid hormone, growth hormone, insulin growth factor-1, thyroxine, glucagon), derived from the blood supply to the bone. Furthermore, within the trabecular bone remodeling unit which has the highest bone turnover rate and hormone responsiveness, the pentapeptide accumulates over the long cytoplasmic processes of osteocytes, the canaliculi. These tubular channel processes lie adjacent to osteocyte lacunae and open to extracellular fluid at the bone surface. They are involved in the deposition, or resorption of calcium and phosphate ions which are present in the bone extracellular fluid, and with the laying down of hydroxyapatite crystals. In addition, the periosteum is needed in bone regeneration during fracture repair (Jee et al., 1988). This finding suggests that SMR1-derived peptides may contribute to the regulation of bone dynamics and turnover in adult male rat, as hormonal modulators.

Besides, SMG-derived pentapeptide could also act as mineral transport agent, however its exclusive uptake by skeletal bone matrix (not by cartilagenous matrix) and renal proximal tubules (not by distal tubules) argues against such a hypothesis. It could also interact as effector agent of membrane enzyme activity which is involved in skeletal mineralization and mineral renal reabsorption. However, peptide-enzyme interaction might have high-affinity binding characteristics in order to identify its selective location in vivo just as it is observed in the present study.

Evidence for the existence of pentapeptide binding sites localized within tubules of dentinal rat incisor, was obtained. The layer of mature dentin is postulated to be involved in the initiation of a mineralization process of the tooth (Bernard, 1972). Strikingly, it has been reported that the hormonal stimulation of fluid movement through these dentinal tubules may be dependent in part upon parotid factors which are carried by the circulation to the teeth (Leonora et al., 1987; Tieche et al., 1994).

Pentapeptide uptake by dentinal tissue and alveolar bone of the incisors, which are subject in the rat to continuous growth and rapid remodeling, respectively, gives additional evidence that the submandibular gland-derived pentapeptide is involved in the regulation of mineral balance between skeletal, dental and renal mineral transport and thus mineral homeostasis. Furthermore, in relation to male rat-specific behavioral characteristics, these data suggest that the androgen-regulated SMR1-derived pentapeptide may be a component, operating under stressful circumstances which lead to its systemic secretion, of a feedback loop to regulate the cascade side effects on mineral balance, thereby satisfying mineral homeostatic requirements.

Otherwise, intestine and liver as well as salivary glands are still major potential sites of ions handling and regulation. The moderate and delayed pentapeptide uptake by intestine and liver could be related to a weak distribution of active peptide in these tissues. Besides, delayed and widespread cellular distribution of peptide accumulation within the submandibular gland could be due to either a sufficient endogenous production of SMR1-derived peptides at concentrations that occupy available binding sites, and/or incomplete functional differentiation of 5 week-old rat SMG cells that are potentially involved in the peptide uptake. Indeed, if the SMR1 secreting acinar-cell differentiation occurs during the first six weeks, the ductal cells are fully differentiated only from 10 weeks postnatal developmental stage (Leeson et al., 1959). Nevertheless, the specific accumulation of the pentapeptide to the submandibular lobules supports the hypothesis that endogenously produced peptides act locally. In addition, since local concentration of SMR1-derived peptides might be greater than the micromolar range in adult male rat SMG, the circulating peptide would weakly if at all, intervene in gland function.

The gastric chief cells and pancreatic acinar cells are also targets for the pentapeptide, supporting the conclusion that the SMR1-derived peptides have a functional role in modulating the synthesis and/or secretion in both of the zymogen-secreting cells and/or secretion of the fluid and electrolytes in the acinar cells. The secretion of gastric and pancreatic digestive enzymes is highly regulated and significant amounts of the enzymes are released only upon stimulation of the zymogenic cells, as occurs during feeding (reviewed in Hersey 1994 and in Jensen, 1994). In addition, the major mechanism for regulation of enzyme secretion is generally held to be stimulation by secretagogues. Secretagogue receptors for a number of peptide hormones have been described on these cells, including the secretin/vasoactive intestinal peptide and the cholecystokin families (plus Gastrin-releasing peptides, tachykinins for acinar cells). The demonstration of pentapeptide binding sites within these exocrine cells supports the hypothesis of a regulatory role of SMR1-derived peptides in the systemic control of early digestive processes. Chromatography characteristics of circulating and tissue bound pentapeptide revealed that the transport and the uptake of the peptide involves a complex molecular species including a cation mineral element. For a general agreement, SMG-derived pentapeptide, as all the major hormones, may be anchored to plasma binding molecules as circulating reservoir to prevent degradation and/or to facilitate transport then association to cell receptor sites.

In conclusion, the data presented in the instant specification led the inventors to the discovery that the circulating SMR1-derived pentapeptide is primarily involved in the hormonal control of mineral balance between at least four systems: the bone, the kidney, the tooth and the circulation. Mineral imbalance can occur in response to acute or chronic stress circumstances including intraspecies fighting and feelings of pain, thirst, starvation and harmful temperatures. The circulating androgen-dependent pentapeptide may be a component of a feedback loop that regulates, in adult male rats, the cascade response to environmental stress within which mineral intake or excretion are modified, thereby controlling mineral homeostasis.

Example 5

The Cellular Receptor Complex that Binds In Vivo the SMR1-pentapeptide has been Isolated and Biochemically Characterized Experimental procedure: First purification steps of the receptor site of the outer medulla of kidney.

The procedure presented herebelow represents the final result of the studies relative to the optimization of the conditions appropriated to the specific isolation of the molecular SMR1 receptor-pentapeptide complex, whose subcellular localization and molecular characteristics were previously unknown.

The selection of the molecular population that is sought is realized by systemically detecting the radioactivity (3H) borne by the ligand (SMR1-pentapeptide) which is itself covalently cross-linked to its cellular receptor-site.

Since binding and cross-linking are performed in vivo, the physiological relevance of that interaction is ensured.

The target-tissular receptor sites are radiolabelled in vivo by means of the tritiated SMR1-pentapetide (method used for the cellular localizations, Rougeot et al., Am. J. of Physiol., 1997).

45 minutes after injection of the radiolabelled ligand (300 ng), the subject (rat) is infused (KREBS; +4° C.) in order to remove the free peptide and the peptide with a low uptake by the target organs (non specific).

The covalent cross-linking of the radiolabelled ligand at the target sites is obtained after an infusion with conjugating agents for primary amines, epsilon lysine, or guanidium arginine (paraformaldehyde+glutaraldehyde: 0,5% in presence of glucose: 2.5%, calcium chloride: 1.2 mM and DMSO: 0.5%)

Kidneys, pancreas, femor bones, incisors and glandular gastric mucosa are quickly removed, cleaned and incubated at +4° C. in presence of formaldehyde 0.25%+ glucose 2.5% for 3 to 17 hours.

Organs are washed with PBS 25 mM pH7.4 and incubated in the presence of glycine 0.2 M at +4° C. for ensuring saturation of the remaining free aldehyde groups Organs are dissected: outer medulla of kidney; mineral and organic contents of incisors and femur bones Tissues cut in pieces are washed at +4° C. with 20 vol of PBS (in two steps of 10 vol each) in presence of protease inhibitors (see cocktails in Am. J. Physiol., Rougeot et al., 1994)

Tissues are ground at +4° C. (Potter homogenizer) in 2×10 vol. of ammonium acetate ($AcNH_4$) 5 mM pH 8.8 in the presence of inhibitors. The homogenate is sonicated at +4° C. and afterwards centrifugated at 1000 g at +4° C. for 15 minutes.

Supernatants (=total extracts) typically contain 60-85% of the initial radioactivity contained within the crude extract.

The soluble fraction (cytosol proteins) is separated from the insoluble components (membraneous) after a centrifugation at 100 000 g for 30-60 minutes at +4° C.

Depending on the tissues, the cytosol supernatants gather 30-50% of the radioactivity contained in the crude extract. The cytosol radioactivity is supposed to represent the internalization and/or intracellular degradation components of the radioactive ligand/receptor complex. Their major isoelectric points are of 5.23-5.85 and their apparent molecular weights are ≧6 kDa (FIGS. 21-24).

The 100 000 g pellets are extracted by solubilizing the membrane components (Rabillard et al., Biofutur 126: 1-12, 1993; Bretscher Sci. Amer. 253:100-109, 1985)

The different assays conducted with the membrane preparations of the outer medulla of kidney and various types of detergents:
an amphoteric or zwitterionic detergent, such as Chaps®
a non ionic detergent such as NP40 or Hecameg®
an anionic detergent such as SDS all used at critical micellar concentrations (CMC) reveal that only SDS provides an almost complete solubilization of the radioactive complex starting from the membrane preparations (table 1, FIG. 9). Although SDS has an excellent solubilizing potency, interactions with proteins are such that on one hand, it is denaturating and on the other hand it is difficult to remove and furthermore interferes with the chromatographic separation systems, thus making impossible any resolutive separation of the various molecular populations. Therefore, the inventors have been led to use a amphoteric type solubilization agent, the sulfobetaines SB14 and SB201 having a low denaturating effect but remarkably efficient relative to proteins associated with the membrane lipidic bi-layer through several transmembrane domains (Vuillard et al., Biochem. J. 305, 337-343, 1995).

Moreover, SBs make possible the subsequent use of various systems of separation such as preparative liquid-flow isoelectrofocusing (IEF) allowing the separation of the molecular population based on their isoelectric point (pHi).

Depending on the tissular membrane preparations, 40 to 90% of the radioactive membrane complex is solubilized, in the presence of that solubilizing agent.

The subsequent steps consist of isolating the radioactive complex starting from the solubilized membrane preparations of the outer medulla of kidney by means of various separating systems, and concurrently of delimitating some of its molecular characteristics which are common or different for the various target tissues. Here again the proposed method is the one which is the final result of various tests for optimizing the appropriate conditions for the specific isolation of the SMR1 receptor-pentapeptide molecular receptor.

the preparative liquid flow isoelectrofocusing (IEF) (ampholyte gradient in Rotofor, Biorad) has been selected as the first step for purifying the solubilized membrane proteins containing the receptor site/SMR1-pentapeptide complex (Marchase et al., Arch. Biochem. and Biophys. 280:122-129, 1990; Rich et al. Technique 1:196-203, 1989; Veser anal. Biochem. 182:217-221, 1989 and Petrash et al. electrophoresis 12:84-90, 1991). The extracts solubilized in SB14/SB20 are directly applied and submitted to a continuous electrical field (500-1000 volts) during 3 hours through a linear gradient of isoelectric point ranging from 3 to 11.

As represented in FIG. 10, for the membrane proteins solubilized from the outer medulla of kidney, this separation procedure based on the isoelectric point is highly resolutive. The radioactive peak coincides with a low amount of proteins (maxima specific activity/cpm/mg of protein).

Proteins with an alkaline pH that are predominant are thus removed.

As far as the outer medulla of kidney is concerned, the radioactive molecular population(s) has(have) a pH of 5.89.

Despite a relatively low purification yield (20-40%) the purification procedure has been used for isolating the ligand-renal receptor site complex.

Furthermore, an analytical step of size exclusion chromatography allowing the separation of species with a molecular weight ranging from 6 to 500 kDa (®Superdex 200, Pharmacia) shows that the fractions resulting from the isoelectrofocusing of the membrane preparations of outer medulla of kidney represent a predominant radioactive population with a molecular weight of 130 kDa (FIG. 13) ascertained by means of a representative calibration (logPM* Ve/Vm FIG. 13).

a liquid chromatography (FPLC) using a stationary reverse $C_{18}$ phase (Rep RPC Pharmacia) represents the second purification step. Since the transmembrane domains of membrane proteins are highly hydrophobic domains, it was reasonable to assume that the receptor site for the SMR1-pentapeptide equally possessed that characteristic.

After dialysis and lyophilization of the radioactive IEF fractions, the lyophilisate is dissolved in ammonium acetate 5 mM pH 8.8 applied to the column at the head thereof and submitted to a linear gradient of acetonitrile (ACN) from 1-100% during 30 minutes at a flow rate of 0.75 ml/min (FIGS. 14 and 15). As represented in FIG. 15, this step is also highly resolutive. Both radioactive populations coincide with a low amount of proteins that are detected at 280 nm.

At this stage, an analytical step is necessary for controlling the purity of the isolated radioactive fractions, namely those eluted by 40% acetonitrile.

This analytical step is performed after an electrophoretic migration step on acrylamide gels in denaturing conditions (SDS-PAGE) of the fractions resulting from the chromatography procedure, followed by a step of revealing the fractions by staining with silver nitrate. Preliminary results indicate that the molecular population represented by peak-1 of radioactivity (retention time of 6 minutes) resulting from $C_{18}$-RP (retention time of 6 minutes) corresponds to two bands with a molecular weight (MW) between 100 and 200 kDa. Peak-2 of radioactivity (retention time of 20-22 minutes in FPLC $C_{18}$-RP) corresponds to a detectable band (with a MW between 100 and 200 kDa).

Biochemical Characteristics of the Different Tissular Receptor Sites

In the course of the various procedures carried out for the adjustment of the purification steps of the receptor site of the medulla of kidney (tissue that predominantly takes up the SMR1-pentapeptide along with pancreas) we have also determined some of the biochemical characteristics that are common or distinct for the various target tissues.

The successive isoelectrofocusing procedures reveal that the radioactive molecular ligand-receptor populations have an isoelectric point of:

5.64±0.30, n=10 determinations for the outer medulla of the kidney (FIG. 16);

5.58±0.30, n=3 determinations for the pancreatic lobes (FIG. 17);

6.62±0.35, n=3 determinations for the glandular gastric mucosa (FIG. 18);

between 4.2 and 4.9 for the predominant population and of 5.6 for the second population of the bone trabecular matrix (FIG. 19, n=1); and 5.74-6.08, n=1 for the dental dentinal matrix (FIG. 20).

Taken together, these results suggest that at least 2 molecular populations of receptor sites for the SMR1-pentapeptide are present: one with a pHi of 5.58/5.64±0.30, mainly represented in the medulla of kidney, pancreas and in a lesser extend in bone trabecular- and dental dentinal-matrix, and the other with a pHi of 6.62±0.35, mainly represented in the glandular gastric mucosa. The third population with a pHi of 4.5±0.4 that is present in the bone trabecular matrix needs further confirmation, for the presence of high amounts of mineral components in that matrix may introduce some modifications in the parameters of IEF separation.

The successive size-exclusion chromatographs have been used as analytical steps rather than preparative (poor resolutive method) or as a step of removal of the solubilization agents (which actually did not occur).

Chromatograms (FIGS. 21-24) representative of each tissue reveal that the radioactive molecular populations have an apparent molecular weight between 200 and 400 kDa. These populations with a high molecular weight found in all target tissues actually correspond to the "protein-detergent" micelles under the analytical circumstances, the molecular weight of the receptor protein being thus somewhat overestimated.

TABLE 1

| Kidney : outer medulla | Cpm (SMR1-bound pentapeptide) | Yield | Specific activity |
|---|---|---|---|
| Crude homogenate | 130 000 | | 43 200 cpm/mg of proteins |
| Whole extract (1000 g) | 105 600 | 81% | |
| Soluble fraction cytosol 100000 g | 26 000 | 27% | 21 533 cpm/mg of proteins |
| Insoluble fraction membrane 100000 g | 40 560 | 61% | |
| Solubilized membrane fractions : chaps 0.5% | 2 520 | 6% | |
| Solubilized membrane fractions : NP40 1% | 3 200 | 8% | |
| Solubilized membrane fractions : hecameg 0.35% | 1 520 | 4% | |
| Solubilized membrane fractions : SDS 0.2% | 35 140 | 87% | 139 900 cpm/mg of proteins |
| Solubilized membrane fractions : SB14 1% + SB201 IM | 28 040 | 69% | 46 733 cpm/mg of proteins |

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

What is claimed is:

1. A method for screening a candidate ligand molecule, comprising:
   a) preparing a biological material comprising a cell sample, cell homogenate, or a tissue sample;
   b) incubating the biological material of a) in the presence of (i) $10^{-10}$-$10^{-5}$ M of a candidate ligand molecule under conditions suitable for activation of adenylate cyclase and in the presence of a submaximal concentration of QHNPR (SEQ ID NO: 1) peptide; and
   c) measuring adenylate cyclase activity present in the biological material of a), respectively, in the presence or in the absence of the candidate ligand molecule and in the presence or in the absence of a submaximal concentration of the peptide QHNPR (SEQ ID NO: 1), and
   d) selecting a ligand molecule which increases or decreases adenylate cyclase activity induced in the biological material of a) by the peptide QHNPR (SEQ ID NO: 1).

2. The method of claim 1, wherein the biological material in a) is a confluent target cell culture monolayer.

3. The method of claim 1, wherein the biological material in a) is a target organ specimen.

4. The method of claim 1, wherein the biological material in a) is a tissue cryosection.

5. The method of claim 1, wherein the biological material in a) is a tissue slice.

6. The method of claim 1, wherein the biological material in a) is a cell homogenate.

7. The method of claim 1, wherein the biological material in a) is a primary cell culture.

8. The method of claim 1, wherein the biological material in a) is an established cell line.

9. A method for screening a candidate ligand molecule, comprising:
   incubating a eukaryotic cell capable of synthesizing collagen in beta-glycerophosphate in the presence of $10^{-10}$-$10^{-5}$ M of a candidate ligand molecule and in the presence of a submaximal concentration of QHNPR (SEQ ID NO: 1) peptide;
   measuring production of a specific metabolite in the presence or in the absence of the candidate ligand molecule and in the presence of in the absence of a submaximal concentration of QHNPR (SEQ ID NO: 1), and
   selecting a ligand molecule which increases or decreases the production of a specific metabolite induced by the QHNPR (SEQ ID NO: 1) peptide.

10. The method of claim 9, wherein said eukaryotic cell is a mammalian cell that naturally synthesizes collagen.

11. The method of claim 9, wherein said eukaryotic cell is a cell that has been transfected or transformed with a nucleic acid encoding collagen.

12. The method of claim 9, wherein the specific metabolite is calcium.

13. The method of claim 9, wherein the specific metabolite is alkaline phosphatase.

14. The method of claim 9, wherein the specific metabolite is DNA.

15. The method of claim 9, comprising selecting a candidate ligand molecule which increases the production of a specific metabolite induced by the QHNPR (SEQ ID NO: 1) peptide.

16. The method of claim 9, comprising selecting a candidate ligand molecule which decreases the production of a specific metabolite induced by the QHNPR (SEQ ID NO: 1) peptide.

17. A method for screening a candidate ligand molecule comprising:
   incubating a biological material comprising a cell sample, cell homogenate, or a tissue sample in the presence of $10^{-10}$-$10^{-5}$ M of a candidate ligand molecule and in the presence of a submaximal concentration of QHNPR (SEQ ID NO: 1);
   measuring a metabolic change, respectively, in the presence or in the absence of the candidate ligand molecule and in the presence or in the absence of a submaximal concentration of the peptide QHNPR (SEQ ID NO: 1),
   selecting a ligand molecule which increases or decreases the metabolic change induced by the peptide QHNPR (SEQ ID NO: 1).

18. The method of claim 17, wherein the biological material is a target organ specimen.

19. The method of claim 17, wherein the biological material is a tissue cryosection.

20. The method of claim 17, wherein the biological material is a tissue slice.

21. The method of claim 17, wherein the biological material is a cell homogenate.

22. The method of claim 17, wherein the biological material is a primary cell culture.

23. The method of claim 17, wherein the biological material is an established cell line.

24. The method of claim 17, wherein the metabolic change is measured by an enzyme assay.

25. The method of claim 17, wherein the metabolic change is measured by an ion transport assay.

26. The method of claim 17, wherein the metabolic change is measured by a signal transduction assay.

27. The method of claim 17, comprising selecting a candidate molecule which increases the metabolic change induced by QHNPR (SEQ ID NO: 1) alone.

28. The method of claim 17, comprising selecting a candidate molecule which decreases the metabolic change induced by QHNPR (SEQ ID NO: 1) alone.

* * * * *